US010913734B2

(12) United States Patent
Du et al.

(10) Patent No.: US 10,913,734 B2
(45) Date of Patent: Feb. 9, 2021

(54) SUBSTITUTED AMINOTHIAZOLES

(71) Applicant: BARUCH S. BLUMBERG INSTITUTE, Doylestown, PA (US)

(72) Inventors: Yanming Du, Cheshire, CT (US); Huagang Lu, Doylestown, PA (US); John Rogowsky, Doylestown, PA (US); William A. Kinney, Doylestown, PA (US); Andrea Cuconati, Doylestown, PA (US)

(73) Assignee: BARUCH S. BLUMBERG INSTITUTE

( * ) Notice: Subject to any disclaimer, the term of this patent is extended or adjusted under 35 U.S.C. 154(b) by 0 days.

(21) Appl. No.: 16/317,191

(22) PCT Filed: Jul. 11, 2017

(86) PCT No.: PCT/US2017/041443

§ 371 (c)(1),
(2) Date: Jan. 11, 2019

(87) PCT Pub. No.: WO2018/013508

PCT Pub. Date: Jan. 18, 2018

(65) Prior Publication Data

US 2019/0241552 A1 Aug. 8, 2019

Related U.S. Application Data

(60) Provisional application No. 62/360,638, filed on Jul. 11, 2016.

(51) Int. Cl.

| | |
|---|---|
| ***C07D 417/14*** | (2006.01) |
| ***C07D 401/14*** | (2006.01) |
| ***A61P 35/00*** | (2006.01) |
| ***A61P 31/12*** | (2006.01) |
| ***A61P 31/14*** | (2006.01) |
| ***A61P 31/20*** | (2006.01) |
| ***C07F 9/6558*** | (2006.01) |

(52) U.S. Cl.

CPC ............ *C07D 417/14* (2013.01); *A61P 31/12* (2018.01); *A61P 31/14* (2018.01); *A61P 31/20* (2018.01); *A61P 35/00* (2018.01); *C07D 401/14* (2013.01); *C07F 9/65583* (2013.01)

(58) Field of Classification Search

CPC .......... A61P 31/12; A61P 31/14; A61P 31/20; A61P 35/00; C07D 401/14; C07D 417/14; C07F 9/65583

See application file for complete search history.

(56) References Cited

U.S. PATENT DOCUMENTS

| | | | | |
|---|---|---|---|---|
| 5,530,000 | A | 6/1996 | Sanfilippo et al. | |
| 2003/0187040 | A1 | 10/2003 | Pevarello et al. | |
| 2005/0227989 | A1 * | 10/2005 | Wang .................. | C07D 417/14 514/252.05 |
| 2008/0108600 | A1 * | 5/2008 | Wang .................. | C07D 213/61 514/218 |
| 2011/0257179 | A1 | 10/2011 | Bolea | |
| 2013/0210809 | A1 | 8/2013 | Bolea et al. | |
| 2014/0249154 | A1 * | 9/2014 | Cuconati ............. | A61K 31/425 514/249 |

OTHER PUBLICATIONS

European Search Report from corresponding EP Application No. 17828262.0-1116/3481810 dated Apr. 29, 2019, pp. 1-10.

Corresponding Search Report for International Application No. PCT/US17/41443, dated Nov. 9, 2017. WO.

* cited by examiner

*Primary Examiner* — Erich A Leeser

(74) *Attorney, Agent, or Firm* — The Belles Group, P.C.

(57) ABSTRACT

Described herein are substituted aminothiazoles, compositions comprising same; and methods of making and using same.

18 Claims, No Drawings

SUBSTITUTED AMINOTHIAZOLES

CROSS-REFERENCE TO RELATED APPLICATION

This application claims the benefit of priority from U.S. Provisional Application No. 62/360,638, filed Jul. 11, 2016, entitled: "Novel Substituted Aminothiazoles as Inhibitors of Cancers, Including Hepatocellular Carcinoma, and as Inhibitors of Hepatitis Virus Replication", the contents of which are hereby incorporated by reference herein in their entirety.

FIELD OF THE DISCLOSURE

The present invention describes compounds and methods useful for the treatment of cancer, including primary liver cancer, hepatocellular carcinoma, hepatoblastoma, and cholangiocarcinoma, and the treatment of viral hepatitis infection, including but not limited to hepatitis A virus infection, hepatitis B virus infection, hepatitis C virus infection, hepatitis D virus infection, and hepatitis E virus infection, as well as other viral species that infect the liver.

BACKGROUND

Primary liver cancer is currently the fifth most common cause of cancer deaths among men, and ninth among women in the US, with the numbers increasing yearly. The most recent data indicate that in 2008 there were an estimated 21,370 new cases of liver and bile duct cancer of which the majority are hepatocellular carcinomas (HCCs), with 18,410 deaths (Institute, N.C., SEER Cancer Statistics Review, 1975-2005, Ries L A G, et al., Editors. 2008.). Worldwide, it is the fourth most common cancer, with approximately 663,00 fatal cases reported in 2008; based on current trends and baseline models, the incidence is expected to rise to 756,000 in 2015, and 955,000 in 2030 (Mathers, C. D. and D. Loncar, Projections of global mortality and burden of disease from 2002 to 2030. PLoS Med, 2006. 3, 11, p. e442.). Although it is comparatively uncommon in the US, its incidence has been rising over the last 20 years partially as a result of burgeoning numbers of cases of chronic hepatitis C (Caldwell, S. and S. H. Park, The epidemiology of hepatocellular cancer: from the perspectives of public health problem to tumor biology. J Gastroenterol, 2009. 44 Suppl 19: p. 96-101. El-Serag, H. B., et al., The continuing increase in the incidence of hepatocellular carcinoma in the United States: an update. Ann Intern Med, 2003. 139(10): p. 817-23) one of the principal causes along with hepatitis B and aflatoxin exposure.

There is a long felt need for new drugs that are both disease-modifying and effective in treating patients with primary liver cancer, including but not limited to hepatocellular carcinoma, hepatoblastoma, and cholangiocarcinoma. There is also a clear and present need for new therapeutic agents that are both disease modifying and effective in treating patients that are infected with a hepatitis virus. The present invention addresses the need for new drugs that are both disease-modifying and effective in treating patients suffering from primary liver cancer and hepatocellular carcinoma. Because the present invention targets the cell types that have been demonstrated to support viral infection in the liver, the present invention addresses also the need for new antiviral drugs that are both disease-modifying and effective in treating patients that are infected with hepatitis A virus, hepatitis B virus, hepatitis C virus, hepatitis D virus, and hepatitis E virus., as well as other viral species that infect the liver.

SUMMARY

The present invention is directed toward novel compounds of formula (I), (I)

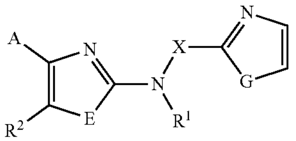

including enantiomers, diastereomers, hydrates, solvates, pharmaceutically acceptable salts, prodrugs and complexes thereof, wherein:

A is selected from the group consisting of

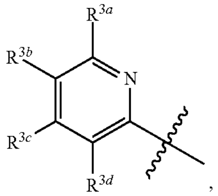
,
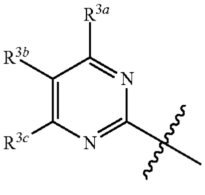
,
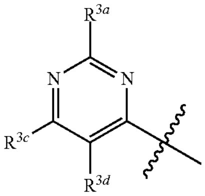
and
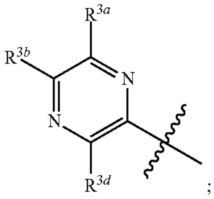
;

E is selected from the group consisting of $CR^4{=}CR^5$ and S;

G is selected from the group consisting of $N{=}CR^6$, NH, and S;

X is selected from a group consisting of $(CH_2)_m$ and CONH—;

m=0, 1, 2, 3, or 4.

$R^1$ is selected from the group consisting of hydrogen,

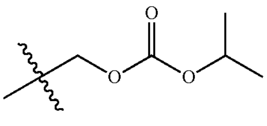
,
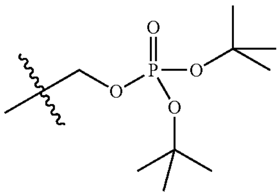
,
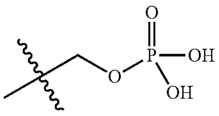
,
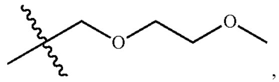
,

-continued

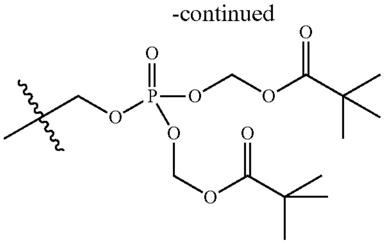

, and

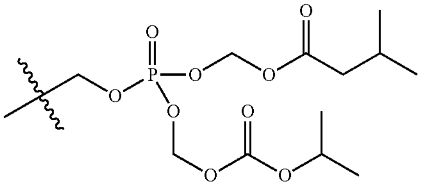

;

$R^2$ is selected from the group consisting of hydrogen,

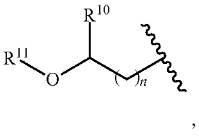

,

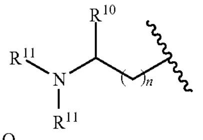

and

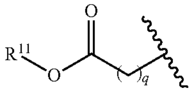

;

$R^{3a}$, $R^{3b}$, and $R^{3c}$ are at each occurrence independently selected from the group consisting of hydrogen, halogen, optionally substituted $C_{1-6}$ alkyl, and optionally substituted $C_{1-6}$ haloalkyl;

$R^{3d}$ is selected from the group consisting of hydrogen, halogen, optionally substituted $C_{1-6}$ alkyl, optionally substituted $C_{1-6}$ haloalkyl, optionally substituted $C_{1-6}$ alkenyl, $CO_2R^7$, $CONHR^8$, and $OR^9$;

n=0 or 1;

q=0, 1 or 2;

$R^4$ is at each occurrence independently selected from the group consisting of hydrogen, halogen, optionally substituted $C_{1-6}$ alkyl, optionally substituted $C_{1-6}$ haloalkyl, optionally substituted $C_{1-6}$ alkenyl, $CO_2R^7$, $CONHR^8$, and $OR^9$;

$R^5$ is at each occurrence independently selected from the group consisting of hydrogen, halogen, optionally substituted $C_{1-6}$ alkyl, optionally substituted $C_{1-6}$ haloalkyl, optionally substituted $C_{1-6}$ alkenyl, $CO_2R^7$, $CONHR^8$, and $OR^9$;

$R^6$ is at each occurrence independently selected from the group consisting of hydrogen, halogen, optionally substituted $C_{1-6}$ alkyl, optionally substituted $C_{1-6}$ haloalkyl, optionally substituted $C_{1-6}$ alkenyl, $CO_2R^7$, $CONHR^8$, and $OR^9$;

$R^7$ is at each occurrence independently selected from the group consisting of hydrogen and optionally substituted $C_{1-6}$ alkyl;

$R^8$ is at each occurrence independently selected from the group consisting of hydrogen and optionally substituted $C_{1-6}$ alkyl;

$R^9$ is at each occurrence independently selected from the group consisting of hydrogen, halogen, and optionally substituted $C_{1-6}$ alkyl;

$R^{10}$ is at each occurrence independently selected from the group consisting of hydrogen, cyclopropyl,

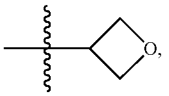 [SMILES: *C1COC1]

$CF_3$, and $CHF_2$;

$R^{11}$ is at each occurrence independently selected from the group consisting of hydrogen and optionally substituted $C_{1-6}$ alkyl.

The present invention further relates to compositions comprising an effective amount of one or more compounds according to the present invention and an excipient.

The present invention also relates to a method for treating or preventing diseases that involve unregulated cell growth, including, for example, primary liver cancer, hepatocellular carcinoma, hepatoblastoma, cholangiocarcinoma breast cancer, ovarian cancer, lung cancer, leukemia, and metastatic disease, said method comprising administering to a subject an effective amount of a compound or composition according to the present invention.

The present invention yet further relates to a method for treating or preventing diseases that involve unregulated cell growth, including, for example, primary liver cancer, hepatocellular carcinoma, hepatoblastoma, and cholangiocarcinoma, breast cancer, ovarian cancer, lung cancer, leukemia, and metastatic disease, wherein said method comprises administering to a subject a composition comprising an effective amount of one or more compounds according to the present invention and an excipient.

The present invention also relates to a method for treating or preventing disease or conditions associated with primary liver cancer, hepatocellular carcinoma, hepatoblastoma, and cholangiocarcinoma, breast cancer, ovarian cancer, lung cancer, leukemia, and metastatic disease, and diseases that involve unregulated cell growth. Said methods comprise administering to a subject an effective amount of a compound or composition according to the present invention.

The present invention yet further relates to a method for treating or preventing disease or conditions associated with primary liver cancer, hepatocellular carcinoma, hepatoblastoma, and cholangiocarcinoma, breast cancer, ovarian cancer, lung cancer, leukemia, and metastatic disease, and diseases that involve unregulated cell growth, wherein said method comprises administering to a subject a composition comprising an effective amount of one or more compounds according to the present invention and an excipient.

The present invention also relates to a method for treating or preventing disease or conditions associated with unregulated cell growth. Said methods comprise administering to a subject an effective amount of a compound or composition according to the present invention.

The present invention yet further relates to a method for treating or preventing disease or conditions associated with unregulated cell growth, wherein said method comprises administering to a subject a composition comprising an effective amount of one or more compounds according to the present invention and an excipient.

The present invention also relates to a method for treating or preventing diseases that involve infection with a hepatits virus, including, for example, hepatitis A virus, hepatitis B virus, hepatitis C virus, hepatitis D virus, and hepatitis E virus, as well as other viral species that infect the liver, said method comprising administering to a subject an effective amount of a compound or composition according to the present invention.

The present invention yet further relates to a method for treating or preventing diseases that involve infection with a hepatitis virus, including, for example, hepatitis A virus, hepatitis B virus, hepatitis C virus, hepatitis D virus, and hepatitis E virus, as well as other viral species that infect the liver, wherein said method comprises administering to a subject a composition comprising an effective amount of one or more compounds according to the present invention and an excipient.

The present invention also relates to a method for treating or preventing disease or conditions associated with hepatitis A virus, hepatitis B virus, hepatitis C virus, hepatitis D virus, and hepatitis E virus, and diseases that involve infection with a hepatits virus as well as other viral species that infect the liver. Said methods comprise administering to a subject an effective amount of a compound or composition according to the present invention.

The present invention yet further relates to a method for treating or preventing disease or conditions associated with hepatitis A virus, hepatitis B virus, hepatitis C virus, hepatitis D virus, and Hepatitis E virus, and diseases that involve infection with a hepatits virus as well as other viral species that infect the liver, wherein said method comprises administering to a subject a composition comprising an effective amount of one or more compounds according to the present invention and an excipient.

The present invention also relates to a method for treating or preventing disease or conditions associated with infection with a hepatits virus, as well as other viral species that infect the liver. Said methods comprise administering to a subject an effective amount of a compound or composition according to the present invention.

The present invention yet further relates to a method for treating or preventing disease or conditions associated with infection with a hepatits virus, as well as other viral species that infect the liver, wherein said method comprises administering to a subject a composition comprising an effective amount of one or more compounds according to the present invention and an excipient.

The present invention further relates to a process for preparing the compounds of the present invention.

These and other objects, features, and advantages will become apparent to those of ordinary skill in the art from a reading of the following detailed description and the appended claims. All percentages, ratios and proportions herein are by weight, unless otherwise specified. All temperatures are in degrees Celsius (° C.) unless otherwise specified. All documents cited are in relevant part, incorporated herein by reference; the citation of any document is not to be construed as an admission that it is prior art with respect to the present invention.

DETAILED DESCRIPTION

The substituted aminothiazoles of the present invention are capable of treating and preventing diseases associated with unregulated cell growth, for example primary liver cancer hepatocellular carcinoma, hepatoblastoma, and cholangiocarcinoma, breast cancer, ovarian cancer, lung cancer, leukemia, and metastatic disease. The substituted aminothiazoles of the present invention are also capable of treating and preventing diseases associated with infection with a hepatits virus, for example hepatitis A virus, hepatitis B virus, hepatitis C virus, hepatitis D virus, and hepatitis E virus, as well as other viruses that infect the liver It has been discovered that compounds of the disclosure cause cell cycle arrest and apoptosis in hepatocellular carcinoma (HCC)-derived cells as well as hepatoblastoma, breast cancer cells, and ovarian carcinoma cells. In addition, it has been determined that the effect on sensitive cells, for example HCC-derived cells as well as hepatoblastoma, breast cancer cells, and ovarian carcinoma cells, is non-reversible, and that the compounds of the disclosure act through inhibition of mitotic anti-apoptotic signaling by the regulatory kinases AKT, mTORC1 and mTORC2. Further, the substituted aminothiazoles of the disclosure destroy cells that support infection with a hepatits virus, for example hepatitis A virus, hepatitis B virus, hepatitis C virus, hepatitis D virus, and Hepatitis E virus, such as (cell type to support Hepatitis infection), and can serve as antiviral agents for the treatment and prevention of diseases associated with infection with a hepatits virus, for example hepatitis A virus, hepatitis B virus, hepatitis C virus, hepatitis D virus, and Hepatitis E virus, as well as other viral species that infect the liver.

Without wishing to be limited by theory, it is believed that the substituted aminothiazoles of the disclosure can ameliorate, abate, otherwise cause to be controlled, diseases associated unregulated cell growth. In addition, and also without wishing to be limited by theory, it is believed that the substituted aminothiazoles of the disclosure can ameliorate, abate, otherwise cause to be controlled, diseases associated with infection of the liver with a virus.

Throughout the description, where compositions are described as having, including, or comprising specific components, or where processes are described as having, including, or comprising specific process steps, it is contemplated that compositions of the present teachings also consist essentially of, or consist of, the recited components, and that the processes of the present teachings also consist essentially of, or consist of, the recited processing steps.

In the application, where an element or component is said to be included in and/or selected from a list of recited elements or components, it should be understood that the element or component can be any one of the recited elements or components and can be selected from a group consisting of two or more of the recited elements or components.

The use of the singular herein includes the plural (and vice versa) unless specifically stated otherwise. In addition, where the use of the term "about" is before a quantitative value, the present teachings also include the specific quantitative value itself, unless specifically stated otherwise.

It should be understood that the order of steps or order for performing certain actions is immaterial so long as the present teachings remain operable. Moreover, two or more steps or actions can be conducted simultaneously.

As used herein, the term "halogen" shall mean chlorine, bromine, fluorine and iodine.

As used herein, unless otherwise noted, "alkyl" and/or "aliphatic" whether used alone or as part of a substituent group refers to straight and branched carbon chains having 1 to 20 carbon atoms or any number within this range, for example 1 to 6 carbon atoms or 1 to 4 carbon atoms. Designated numbers of carbon atoms (e.g. $C_{1-6}$) shall refer independently to the number of carbon atoms in an alkyl moiety or to the alkyl portion of a larger alkyl-containing substituent. Non-limiting examples of alkyl groups include methyl, ethyl, n-propyl, iso-propyl, n-butyl, sec-butyl, isobutyl, tert-butyl, and the like. Alkyl groups can be optionally substituted. Non-limiting examples of substituted alkyl groups include hydroxymethyl, chloromethyl, trifluoromethyl, aminomethyl, 1-chloroethyl, 2-hydroxyethyl, 1,2-difluoroethyl, 3-carboxypropyl, and the like. In substituent groups with multiple alkyl groups such as $(C_{1-6}alkyl)_2$amino, the alkyl groups may be the same or different.

As used herein, the terms "alkenyl" and "alkynyl" groups, whether used alone or as part of a substituent group, refer to straight and branched carbon chains having 2 or more carbon atoms, preferably 2 to 20, wherein an alkenyl chain has at least one double bond in the chain and an alkynyl chain has at least one triple bond in the chain. Alkenyl and alkynyl groups can be optionally substituted. Nonlimiting examples of alkenyl groups include ethenyl, 3-propenyl, 1-propenyl (also 2-methylethenyl), isopropenyl (also 2-methylethen-2-yl), buten-4-yl, and the like. Nonlimiting examples of substituted alkenyl groups include 2-chloroethenyl (also 2-chlorovinyl), 4-hydroxybuten-1-yl, 7-hydroxy-7-methyloct-4-en-2-yl, 7-hydroxy-7-methyloct-3,5-dien-2-yl, and the like. Nonlimiting examples of alkynyl groups include ethynyl, prop-2-ynyl (also propargyl), propyn-1-yl, and 2-methyl-hex-4-yn-1-yl. Nonlimiting examples of substituted alkynyl groups include, 5-hydroxy-5-methyl-hex-3-ynyl, 6-hydroxy-6-methylhept-3-yn-2-yl, 5-hydroxy-5-ethylhept-3-ynyl, and the like.

As used herein, "cycloalkyl," whether used alone or as part of another group, refers to a non-aromatic carbon-containing ring including cyclized alkyl, alkenyl, and alkynyl groups, e.g., having from 3 to 14 ring carbon atoms, preferably from 3 to 7 or 3 to 6 ring carbon atoms, or even 3 to 4 ring carbon atoms, and optionally containing one or more (e.g., 1, 2, or 3) double or triple bond. Cycloalkyl groups can be monocyclic (e.g., cyclohexyl) or polycyclic (e.g., containing fused, bridged, and/or spiro ring systems), wherein the carbon atoms are located inside or outside of the ring system. Any suitable ring position of the cycloalkyl group can be covalently linked to the defined chemical structure. Cycloalkyl rings can be optionally substituted. Nonlimiting examples of cycloalkyl groups include: cyclopropyl, 2-methyl-cyclopropyl, cyclopropenyl, cyclobutyl, 2,3-dihydroxycyclobutyl, cyclobutenyl, cyclopentyl, cyclopentenyl, cyclopentadienyl, cyclohexyl, cyclohexenyl, cycloheptyl, cyclooctanyl, decalinyl, 2,5-dimethylcyclopentyl, 3,5-dichlorocyclohexyl, 4-hydroxycyclohexyl, 3,3,5-trimethylcyclohex-1-yl, octahydropentalenyl, octahydro-1H-indenyl, 3a,4,5,6,7,7a-hexahydro-3H-inden-4-yl, decahydroazulenyl; bicyclo[6.2.0]decanyl, decahydronaphthalenyl, and dodecahydro-1H-fluorenyl. The term "cycloalkyl" also includes carbocyclic rings which are bicyclic hydrocarbon rings, non-limiting examples of which include, bicyclo-[2.1.1]hexanyl, bicyclo[2.2.1]heptanyl, bicyclo [3.1.1]heptanyl, 1,3-dimethyl[2.2.1]heptan-2-yl, bicyclo [2.2.2]octanyl, and bicyclo[3.3.3]undecanyl.

"Haloalkyl" is intended to include both branched and straight-chain saturated aliphatic hydrocarbon groups having the specified number of carbon atoms, substituted with 1 or more halogen. Haloalkyl groups include perhaloalkyl groups, wherein all hydrogens of an alkyl group have been replaced with halogens (e.g., $—CF_3$, $—CF_2CF_3$). Haloalkyl groups can optionally be substituted with one or more substituents in addition to halogen. Examples of haloalkyl groups include, but are not limited to, fluoromethyl, dichloroethyl, trifluoromethyl, trichloromethyl, pentafluoroethyl, and pentachloroethyl groups.

The term "alkoxy" refers to the group —O-alkyl, wherein the alkyl group is as defined above. Alkoxy groups optionally may be substituted. The term $C_3$-$C_6$ cyclic alkoxy refers to a ring containing 3 to 6 carbon atoms and at least one oxygen atom (e.g., tetrahydrofuran, tetrahydro-2H-pyran). $C_3$-$C_6$ cyclic alkoxy groups optionally may be substituted.

The term "aryl," wherein used alone or as part of another group, is defined herein as a an unsaturated, aromatic monocyclic ring of 6 carbon members or to an unsaturated, aromatic polycyclic ring of from 10 to 14 carbon members. Aryl rings can be, for example, phenyl or naphthyl ring each optionally substituted with one or more moieties capable of replacing one or more hydrogen atoms. Non-limiting examples of aryl groups include: phenyl, naphthylen-1-yl, naphthylen-2-yl, 4-fluorophenyl, 2-hydroxyphenyl, 3-methylphenyl, 2-amino-4-fluorophenyl, 2-(N,N-diethylamino) phenyl, 2-cyanophenyl, 2,6-di-tert-butylphenyl, 3-methoxyphenyl, 8-hydroxynaphthylen-2-yl 4,5-dimethoxynaphthylen-1-yl, and 6-cyano-naphthylen-1-yl. Aryl groups also include, for example, phenyl or naphthyl rings fused with one or more saturated or partially saturated carbon rings (e.g., bicyclo[4.2.0]octa-1,3,5-trienyl, indanyl), which can be substituted at one or more carbon atoms of the aromatic and/or saturated or partially saturated rings.

The term "arylalkyl" or "aralkyl" refers to the group -alkyl-aryl, where the alkyl and aryl groups are as defined herein. Aralkyl groups of the present invention are optionally substituted. Examples of arylalkyl groups include, for example, benzyl, 1-phenylethyl, 2-phenylethyl, 3-phenylpropyl, 2-phenylpropyl, fluorenylmethyl and the like.

The terms "heterocyclic" and/or "heterocycle" and/or "heterocylyl," whether used alone or as part of another group, are defined herein as one or more ring having from 3 to 20 atoms wherein at least one atom in at least one ring is a heteroatom selected from nitrogen (N), oxygen (O), or sulfur (S), and wherein further the ring that includes the heteroatom is non-aromatic. In heterocycle groups that include 2 or more fused rings, the non-heteroatom bearing ring may be aryl (e.g., indolinyl, tetrahydroquinolinyl, chromanyl). Exemplary heterocycle groups have from 3 to 14 ring atoms of which from 1 to 5 are heteroatoms independently selected from nitrogen (N), oxygen (O), or sulfur (S). One or more N or S atoms in a heterocycle group can be oxidized. Heterocycle groups can be optionally substituted.

Non-limiting examples of heterocyclic units having a single ring include: diazirinyl, aziridinyl, urazolyl, azetidinyl, pyrazolidinyl, imidazolidinyl, oxazolidinyl, isoxazolinyl, isoxazolyl, thiazolidinyl, isothiazolyl, isothiazolinyl oxathiazolidinonyl, oxazolidinonyl, hydantoinyl, tetrahydrofuranyl, pyrrolidinyl, morpholinyl, piperazinyl, piperidinyl, dihydropyranyl, tetrahydropyranyl, piperidin-2-onyl (valerolactam), 2,3,4,5-tetrahydro-1H-azepinyl, 2,3-dihydro-1H-indole, and 1,2,3,4-tetrahydro-quinoline. Non-limiting examples of heterocyclic units having 2 or more rings include: hexahydro-1H-pyrrolizinyl, 3a,4,5,6,7,7a-hexahydro-1H-benzo[d]imidazolyl, 3a,4,5,6,7,7a-hexahydro-1H-indolyl, 1,2,3,4-tetrahydroquinolinyl, chromanyl, isochromanyl, indolinyl, isoindolinyl, and decahydro-1H-cycloocta[b]pyrrolyl.

The term "heteroaryl," whether used alone or as part of another group, is defined herein as one or more rings having from 5 to 20 atoms wherein at least one atom in at least one ring is a heteroatom chosen from nitrogen (N), oxygen (O), or sulfur (S), and wherein further at least one of the rings that includes a heteroatom is aromatic. In heteroaryl groups that include 2 or more fused rings, the non-heteroatom bearing ring may be a carbocycle (e.g., 6,7-Dihydro-5H-cyclopentapyrimidine) or aryl (e.g., benzofuranyl, benzothiophenyl, indolyl). Exemplary heteroaryl groups have from 5 to 14 ring atoms and contain from 1 to 5 ring heteroatoms independently selected from nitrogen (N), oxygen (O), or sulfur (S). One or more N or S atoms in a heteroaryl group can be oxidized. Heteroaryl groups can be substituted. Non-limiting examples of heteroaryl rings containing a single ring include: 1,2,3,4-tetrazolyl, [1,2,3]triazolyl, [1,2,4]triazolyl, triazinyl, thiazolyl, 1H-imidazolyl, oxazolyl, furanyl, thiopheneyl, pyrimidinyl, 2-phenylpyrimidinyl, pyridinyl, 3-methylpyridinyl, and 4-dimethylaminopyridinyl. Non-limiting examples of heteroaryl rings containing 2 or more fused rings include: benzofuranyl, benzothiophenyl, benzoxazolyl, benzthiazolyl, benztriazolyl, cinnolinyl, naphthyridinyl, phenanthridinyl, 7H-purinyl, 9H-purinyl, 6-amino-9H-purinyl, 5H-pyrrolo[3,2-d]pyrimidinyl, 7H-pyrrolo[2,3-d]pyrimidinyl, pyrido[2,3-d]pyrimidinyl, 2-phenylbenzo[d]thiazolyl, 1H-indolyl, 4,5,6,7-tetrahydro-1-H-indolyl, quinoxalinyl, 5-methylquinoxalinyl, quinazolinyl, quinolinyl, 8-hydroxy-quinolinyl, and isoquinolinyl.

One non-limiting example of a heteroaryl group as described above is $C_1$-$C_5$ heteroaryl, which has 1 to 5 carbon ring atoms and at least one additional ring atom that is a heteroatom (preferably 1 to 4 additional ring atoms that are heteroatoms) independently selected from nitrogen (N), oxygen (O), or sulfur (S). Examples of $C_1$-$C_5$ heteroaryl include, but are not limited to, triazinyl, thiazol-2-yl, thiazol-4-yl, imidazol-1-yl, 1H-imidazol-2-yl, 1H-imidazol-4-yl, isoxazolin-5-yl, furan-2-yl, furan-3-yl, thiophen-2-yl, thiophen-4-yl, pyrimidin-2-yl, pyrimidin-4-yl, pyrimidin-5-yl, pyridin-2-yl, pyridin-3-yl, and pyridin-4-yl.

Unless otherwise noted, when two substituents are taken together to form a ring having a specified number of ring atoms (e.g., $R^2$ and $R^3$ taken together with the nitrogen (N) to which they are attached to form a ring having from 3 to 7 ring members), the ring can have carbon atoms and optionally one or more (e.g., 1 to 3) additional heteroatoms independently selected from nitrogen (N), oxygen (O), or sulfur (S). The ring can be saturated or partially saturated and can be optionally substituted.

For the purposed of the present invention fused ring units, as well as spirocyclic rings, bicyclic rings and the like, which comprise a single heteroatom will be considered to belong to the cyclic family corresponding to the heteroatom containing ring. For example, 1,2,3,4-tetrahydroquinoline having the formula:

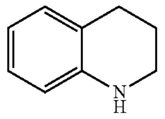

is, for the purposes of the present invention, considered a heterocyclic unit. 6,7-Dihydro-5H-cyclopentapyrimidine having the formula:

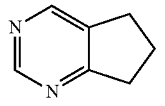

is, for the purposes of the present invention, considered a heteroaryl unit. When a fused ring unit contains heteroatoms in both a saturated and an aryl ring, the aryl ring will predominate and determine the type of category to which the ring is assigned. For example, 1,2,3,4-tetrahydro-[1,8]naphthyridine having the formula:

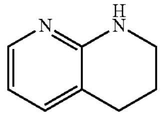

is, for the purposes of the present invention, considered a heteroaryl unit.

Whenever a term or either of their prefix roots appear in a name of a substituent the name is to be interpreted as including those limitations provided herein. For example, whenever the term "alkyl" or "aryl" or either of their prefix roots appear in a name of a substituent (e.g., arylalkyl, alkylamino) the name is to be interpreted as including those limitations given above for "alkyl" and "aryl."

The term "substituted" is used throughout the specification. The term "substituted" is defined herein as a moiety, whether acyclic or cyclic, which has one or more hydrogen atoms replaced by a substituent or several (e.g., 1 to 10) substituents as defined herein below. The substituents are capable of replacing one or two hydrogen atoms of a single moiety at a time. In addition, these substituents can replace two hydrogen atoms on two adjacent carbons to form said substituent, new moiety or unit. For example, a substituted unit that requires a single hydrogen atom replacement includes halogen, hydroxyl, and the like. A two hydrogen atom replacement includes carbonyl, oximino, and the like. A two hydrogen atom replacement from adjacent carbon atoms includes epoxy, and the like. The term "substituted" is used throughout the present specification to indicate that a moiety can have one or more of the hydrogen atoms replaced by a substituent. When a moiety is described as "substituted" any number of the hydrogen atoms may be replaced. For example, difluoromethyl is a substituted $C_1$ alkyl; trifluoromethyl is a substituted $C_1$ alkyl; 4-hydroxyphenyl is a substituted aromatic ring; (N,N-dimethyl-5-amino)octanyl is a substituted $C_8$ alkyl; 3-guanidinopropyl is a substituted $C_3$ alkyl; and 2-carboxypyridinyl is a substituted heteroaryl.

The variable groups defined herein, e.g., alkyl, alkenyl, alkynyl, cycloalkyl, alkoxy, aryloxy, aryl, heterocycle and heteroaryl groups defined herein, whether used alone or as part of another group, can be optionally substituted. Optionally substituted groups will be so indicated.

The following are non-limiting examples of substituents which can substitute for hydrogen atoms on a moiety: halogen (chlorine (Cl), bromine (Br), fluorine (F) and iodine (I)), —CN, —$NO_2$, oxo (=O), —$OR^{12}$, —$SR^{12}$, —$N(R^{12})_2$, —$NR^{12}C(O)R^{12}$, —$SO_2R^{12}$, —$SO_2OR^{12}$, —$SO_2N(R^{12})_2$, —$C(O)R^{12}$, —$C(O)OR^{12}$, —$C(O)N(R^{12})_2$, $C_{1-6}$ alkyl, $C_{1-6}$ haloalkyl, $C_{1-6}$ alkoxy, $C_{2-8}$ alkenyl, $C_{2-8}$ alkynyl, $C_{3-14}$ cycloalkyl, aryl, heterocycle, or heteroaryl, wherein each of the alkyl, haloalkyl, alkenyl, alkynyl, alkoxy, cycloalkyl, aryl, heterocycle, and heteroaryl groups is optionally substituted with 1-10 (e.g., 1-6 or 1-4) groups selected independently from halogen, —CN, —$NO_2$, oxo, and $R^{12}$; wherein $R^{12}$, at each occurrence, independently is hydrogen, —$OR^{13}$, —$SR^{13}$, —$C(O)R^{13}$, —$C(O)OR^{13}$, —$C(O)N(R^{13})_2$, —$SO_2R^{13}$, —$S(O)_2OR_{13}$, —$N(R^{13})_2$, —$NR_{13}C(O)R_{13}$, $C_{1-6}$ alkyl, $C_{1-6}$ haloalkyl, $C_{2-8}$ alkenyl, $C_{2-8}$ alkynyl, cycloalkyl (e.g., $C_{3-6}$ cycloalkyl), aryl, heterocycle, or heteroaryl, or two $R^{12}$ units taken together with the atom(s) to which they are bound form an optionally substituted carbocycle or heterocycle wherein said carbocycle or heterocycle has 3 to 7 ring atoms; wherein $R^{13}$, at each occurrence, independently is hydrogen, $C_{1-6}$ alkyl, $C_{1-6}$ haloalkyl, $C_{2-8}$ alkenyl, $C_{2-8}$ alkynyl, cycloalkyl (e.g., $C_{3-6}$ cycloalkyl), aryl, heterocycle, or heteroaryl, or two $R^{13}$ units taken together with the atom(s) to which they are bound form an optionally substituted carbocycle or heterocycle wherein said carbocycle or heterocycle preferably has 3 to 7 ring atoms.

In some embodiments, the substituents are selected from i) $—OR^{14}$; for example, —OH, $—OCH_3$, $—OCH_2CH_3$, $—OCH_2CH_2CH_3$;

ii) $—C(O)R^{14}$; for example, $—COCH_3$, $—COCH_2CH_3$, $—COCH_2CH_2CH_3$;

iii) $—C(O)OR^{14}$; for example, $—CO_2CH_3$, $—CO_2CH_2CH_3$, $—CO_2CH_2CH_2CH_3$;

iv) $—C(O)N(R^{14})_2$; for example, $—CONH_2$, $—CONHCH_3$, $—CON(CH_3)_2$;

v) $—N(R^{14})_2$; for example, $—NH_2$, $—NHCH_3$, $—N(CH_3)_2$, $—NH(CH_2CH_3)$;

vi) halogen: —F, —Cl, —Br, and —I;

vii) $—CH_eX_g$; wherein X is halogen, m is from 0 to 2, e+g=3; for example, $—CH_2F$, $—CHF_2$, $—CF_3$, $—CCl_3$, or $—CBr_3$;

viii) $—SO_2R^{14}$; for example, $—SO_2H$; $—SO_2CH_3$; $—SO_2C_6H_5$;

ix) $C_1$-$C_6$ linear, branched, or cyclic alkyl;

x) Cyano xi) Nitro;

xii) $N(R^{14})C(O)R^{14}$;

xiii) Oxo (=O);

xiv) Heterocycle; and xv) Heteroaryl.

wherein each $R^H$ is independently hydrogen, optionally substituted $C_1$-$C_6$ linear or branched alkyl (e.g., optionally substituted $C_1$-$C_4$ linear or branched alkyl), or optionally substituted $C_3$-$C_6$ cycloalkyl (e.g optionally substituted $C_3$-$C_4$ cycloalkyl); or two $R^{14}$ units can be taken together to form a ring comprising 3-7 ring atoms. In certain aspects, each $R^{14}$ is independently hydrogen, $C_1$-$C_6$ linear or branched alkyl optionally substituted with halogen or $C_3$-$C_6$ cycloalkyl or $C_3$-$C_6$ cycloalkyl.

At various places in the present specification, substituents of compounds are disclosed in groups or in ranges. It is specifically intended that the description include each and every individual subcombination of the members of such groups and ranges. For example, the term "$C_{1-6}$ alkyl" is specifically intended to individually disclose $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$, alkyl.

For the purposes of the present invention the terms "compound," "analog," and "composition of matter" stand equally well for the substituted aminothiazoles described herein, including all enantiomeric forms, diastereomeric forms, salts, and the like, and the terms "compound," "analog," and "composition of matter" are used interchangeably throughout the present specification.

Compounds described herein can contain an asymmetric atom (also referred as a chiral center), and some of the compounds can contain one or more asymmetric atoms or centers, which can thus give rise to optical isomers (enantiomers) and diastereomers. The present teachings and compounds disclosed herein include such enantiomers and diastereomers, as well as the racemic and resolved, enantiomerically pure R and S stereoisomers, as well as other mixtures of the R and S stereoisomers and pharmaceutically acceptable salts thereof. Optical isomers can be obtained in pure form by standard procedures known to those skilled in the art, which include, but are not limited to, diastereomeric salt formation, kinetic resolution, and asymmetric synthesis. The present teachings also encompass cis and trans isomers of compounds containing alkenyl moieties (e.g., alkenes and imines). It is also understood that the present teachings encompass all possible regioisomers, and mixtures thereof, which can be obtained in pure form by standard separation procedures known to those skilled in the art, and include, but are not limited to, column chromatography, thin-layer chromatography, and high-performance liquid chromatography.

Pharmaceutically acceptable salts of compounds of the present teachings, which can have an acidic moiety, can be formed using organic and inorganic bases. Both mono and polyanionic salts are contemplated, depending on the number of acidic hydrogens available for deprotonation. Suitable salts formed with bases include metal salts, such as alkali metal or alkaline earth metal salts, for example sodium, potassium, or magnesium salts; ammonia salts and organic amine salts, such as those formed with morpholine, thiomorpholine, piperidine, pyrrolidine, a mono-, di- or tri-lower alkylamine (e.g., ethyl-tert-butyl-, diethyl-, diisopropyl-, triethyl-, tributyl- or dimethylpropylamine), or a mono-, di-, or trihydroxy lower alkylamine (e.g., mono-, di- or triethanolamine). Specific non-limiting examples of inorganic bases include $NaHCO_3$, $Na_2CO_3$, $KHCO_3$, $K_2CO_3$, $Cs_2CO_3$, LiOH, NaOH, KOH, $NaH_2PO_4$, $Na_2HPO_4$, and $Na_3PO_4$. Internal salts also can be formed. Similarly, when a compound disclosed herein contains a basic moiety, salts can be formed using organic and inorganic acids. For example, salts can be formed from the following acids: acetic, propionic, lactic, benzenesulfonic, benzoic, camphorsulfonic, citric, tartaric, succinic, dichloroacetic, ethenesulfonic, formic, fumaric, gluconic, glutamic, hippuric, hydrobromic, hydrochloric, isethionic, lactic, maleic, malic, malonic, mandelic, methanesulfonic, mucic, napthalenesulfonic, nitric, oxalic, pamoic, pantothenic, phosphoric, phthalic, propionic, succinic, sulfuric, tartaric, toluenesulfonic, and camphorsulfonic as well as other known pharmaceutically acceptable acids.

When any variable occurs more than one time in any constituent or in any formula, its definition in each occurrence is independent of its definition at every other occurrence (e.g., in $N(R^4)_2$, each $R^4$ may be the same or different than the other). Combinations of substituents and/or variables are permissible only if such combinations result in stable compounds.

The terms "treat" and "treating" and "treatment" as used herein, refer to partially or completely alleviating, inhibiting, ameliorating and/or relieving a condition from which a patient is suspected to suffer.

As used herein, "therapeutically effective" and "effective dose" refer to a substance or an amount that elicits a desirable biological activity or effect.

Except when noted, the terms "subject" or "patient" are used interchangeably and refer to mammals such as human patients and non-human primates, as well as experimental animals such as rabbits, rats, and mice, and other animals. Accordingly, the term "subject" or "patient" as used herein means any mammalian patient or subject to which the compounds of the invention can be administered. In an exemplary embodiment of the present invention, to identify subject patients for treatment according to the methods of the invention, accepted screening methods are employed to determine risk factors associated with a targeted or suspected disease or condition or to determine the status of an existing disease or condition in a subject. These screening methods include, for example, conventional work-ups to determine risk factors that may be associated with the targeted or suspected disease or condition. These and other routine methods allow the clinician to select patients in need of therapy using the methods and compounds of the present invention.

The compounds of the present invention are substituted aminothiazoles, and include all enantiomeric and diastereomeric forms and pharmaceutically accepted salts thereof having the formula:

(I)

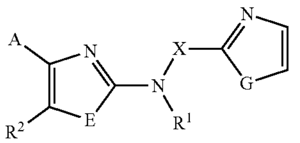

including hydrates, solvates, pharmaceutically acceptable salts, prodrugs and complexes thereof, wherein:

A is selected from the group consisting of

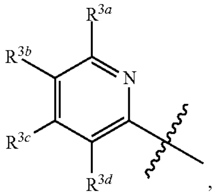,
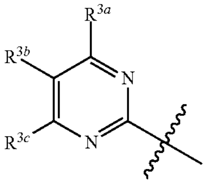,
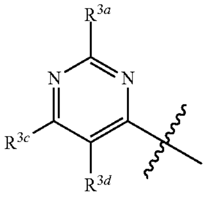 and
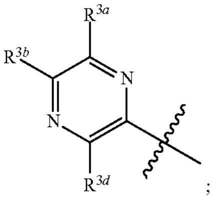;

E is selected from the group consisting of $CR^4$=$CR^5$ and S;

G is selected from the group consisting of N=$CR^6$, NH, and S;

X is selected from a group consisting of $(CH_2)_m$ and CONH—;

m=0, 1, 2, 3, or 4.

$R^1$ is selected from the group consisting of hydrogen,

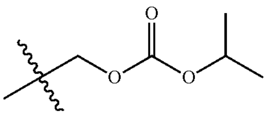,
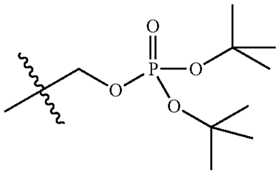,
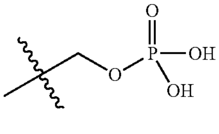,
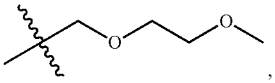,
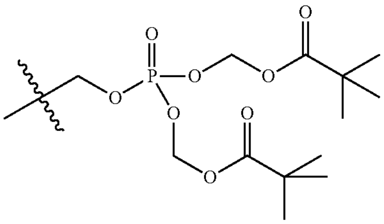, and

-continued

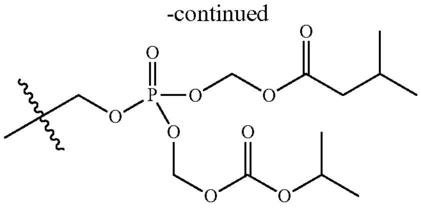;

$R^2$ is selected from the group consisting of hydrogen,

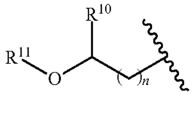,
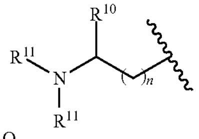 and
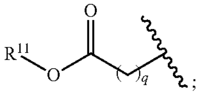;

$R^{3a}$, $R^{3b}$, and $R^{3c}$ are at each occurrence independently selected from the group consisting of hydrogen, halogen, optionally substituted $C_{1-6}$ alkyl, and optionally substituted $C_{1-6}$ haloalkyl;

$R^{3d}$ is selected from the group consisting of hydrogen, halogen, optionally substituted $C_{1-6}$ alkyl, optionally substituted $C_{1-6}$ haloalkyl, optionally substituted $C_{1-6}$ alkenyl, $CO_2R^7$, $CONR^8$, and $OR^9$;

n=0 or 1;

q=0, 1 or 2;

$R^4$ is at each occurrence independently selected from the group consisting of hydrogen, halogen, optionally substituted $C_{1-6}$ alkyl, optionally substituted $C_{1-6}$ haloalkyl, optionally substituted $C_{1-6}$ alkenyl, $CO_2R^7$, $CONHR^8$, and $OR^9$;

$R^5$ is at each occurrence independently selected from the group consisting of hydrogen, halogen, optionally substituted $C_{1-6}$ alkyl, optionally substituted $C_{1-6}$ haloalkyl, optionally substituted $C_{1-6}$ alkenyl, $CO_2R^7$, $CONHR^8$, and $OR^9$;

$R^6$ is at each occurrence independently selected from the group consisting of hydrogen, halogen, optionally substituted $C_{1-6}$ alkyl, optionally substituted $C_{1-6}$ haloalkyl, optionally substituted $C_{1-6}$ alkenyl, $CO_2R^7$, $CONHR^8$, and $OR^9$;

$R^7$ is at each occurrence independently selected from the group consisting of hydrogen and optionally substituted $C_{1-6}$ alkyl;

$R^8$ is at each occurrence independently selected from the group consisting of hydrogen and optionally substituted $C_{1-6}$ alkyl;

$R^9$ is at each occurrence independently selected from the group consisting of hydrogen, halogen, and optionally substituted $C_{1-6}$ alkyl;

$R^{10}$ is at each occurrence independently selected from the group consisting of hydrogen, cyclopropyl,

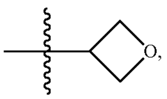, $CF_3$, and $CHF_2$;

$R^{11}$ is at each occurrence independently selected from the group consisting of hydrogen and optionally substituted $C_{1-6}$ alkyl.

The compounds of the present invention include compounds having formula (IA):

(IA)

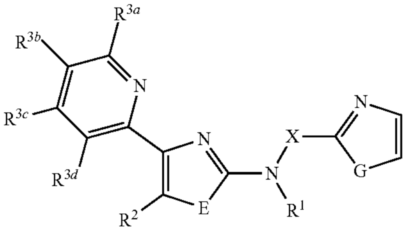

including enantiomers, diastereomers, hydrates, solvates, pharmaceutically acceptable salts, prodrugs and complexes thereof.

The compounds of the present invention include compounds having formula (IB):

(IB)

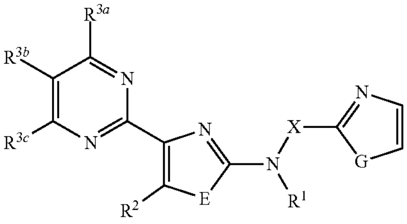

including enantiomers, diastereomers, hydrates, solvates, pharmaceutically acceptable salts, prodrugs and complexes thereof.

The compounds of the present invention include compounds having formula (IC):

(IC)

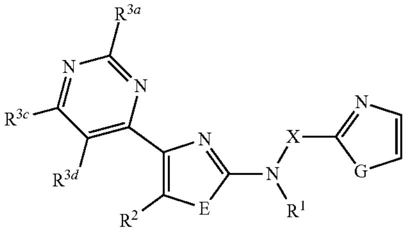

including enantiomers, diastereomers, hydrates, solvates, pharmaceutically acceptable salts, prodrugs and complexes thereof.

The compounds of the present invention include compounds having formula (1D):

(ID)

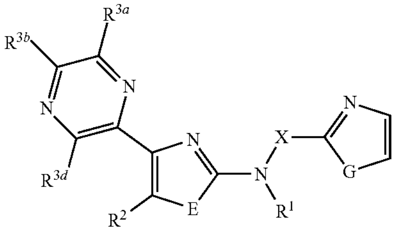

including enantiomers, diastereomers, hydrates, solvates, pharmaceutically acceptable salts, prodrugs and complexes thereof.

The compounds of the present invention include compounds having formula (1E):

(IE)

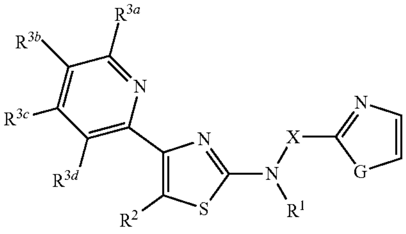

including enantiomers, diastereomers, hydrates, solvates, pharmaceutically acceptable salts, prodrugs and complexes thereof.

The compounds of the present invention include compounds having formula (1F):

(IF)

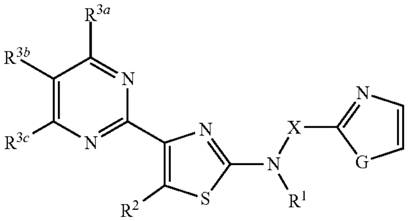

including enantiomers, diastereomers, hydrates, solvates, pharmaceutically acceptable salts, prodrugs and complexes thereof.

The compounds of the present invention include compounds having formula (1G):

(IG)

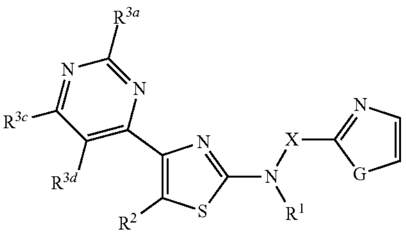

including enantiomers, diastereomers, hydrates, solvates, pharmaceutically acceptable salts, prodrugs and complexes thereof.

The compounds of the present invention include compounds having formula (1H):

(IH)

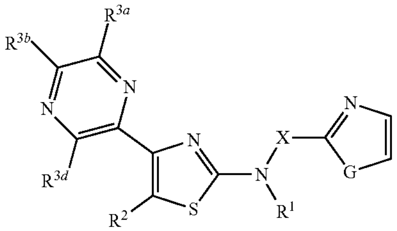

including enantiomers, diastereomers, hydrates, solvates, pharmaceutically acceptable salts, prodrugs and complexes thereof.

The compounds of the present invention include compounds having formula (1J):

(IJ)

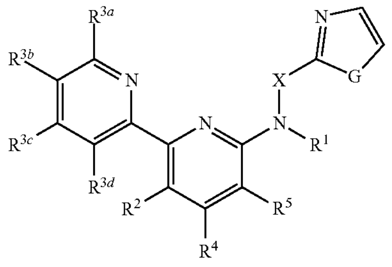

including enantiomers, diastereomers, hydrates, solvates, pharmaceutically acceptable salts, prodrugs and complexes thereof.

The compounds of the present invention include compounds having formula (1K):

(IK)

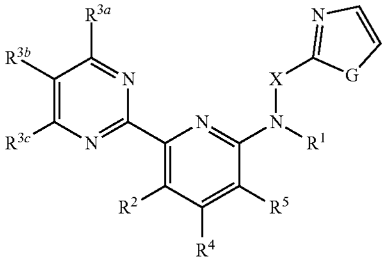

including enantiomers, diastereomers, hydrates, solvates, pharmaceutically acceptable salts, prodrugs and complexes thereof.

The compounds of the present invention include compounds having formula (1L):

(IL)

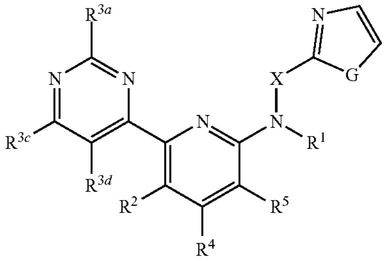

including enantiomers, diastereomers, hydrates, solvates, pharmaceutically acceptable salts, prodrugs and complexes thereof.

The compounds of the present invention include compounds having formula (1M):

(IM)

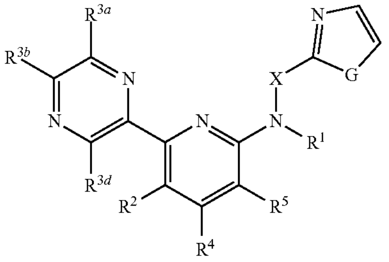

including enantiomers, diastereomers, hydrates, solvates, pharmaceutically acceptable salts, prodrugs and complexes thereof.

The compounds of the present invention include compounds having formula (1N):

(IN)

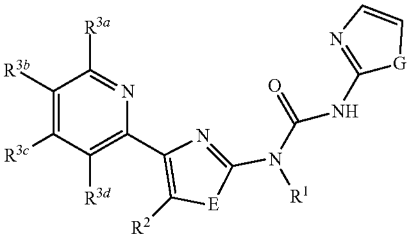

including enantiomers, diastereomers, hydrates, solvates, pharmaceutically acceptable salts, prodrugs and complexes thereof.

The compounds of the present invention include compounds having formula (1O):

(IO)

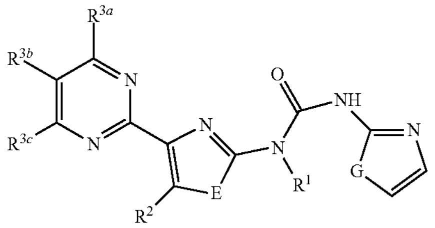

including enantiomers, diastereomers, hydrates, solvates, pharmaceutically acceptable salts, prodrugs and complexes thereof.

The compounds of the present invention include compounds having formula (1P):

(IP)

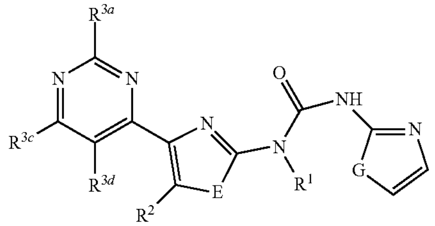

including enantiomers, diastereomers, hydrates, solvates, pharmaceutically acceptable salts, prodrugs and complexes thereof.

The compounds of the present invention include compounds having formula (1Q):

(IQ)

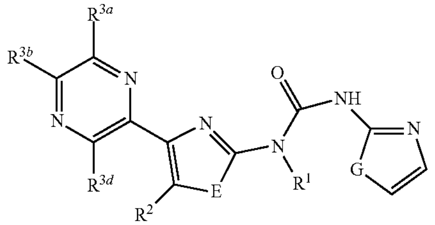

including enantiomers, diastereomers, hydrates, solvates, pharmaceutically acceptable salts, prodrugs and complexes thereof.

The compounds of the present invention include compounds having formula (1R):

(IR)

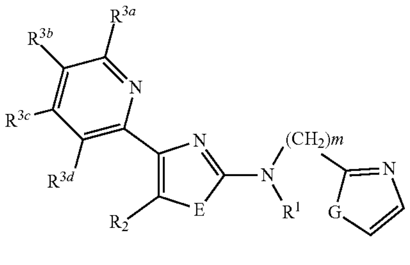

including enantiomers, diastereomers, hydrates, solvates, pharmaceutically acceptable salts, prodrugs and complexes thereof.

The compounds of the present invention include compounds having formula (1S):

(IS)

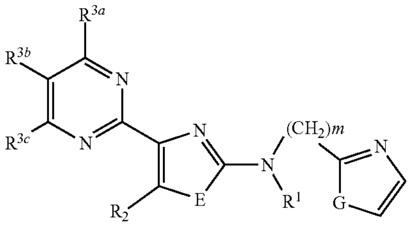

including enantiomers, diastereomers, hydrates, solvates, pharmaceutically acceptable salts, prodrugs and complexes thereof.

The compounds of the present invention include compounds having formula (1T):

(IT)

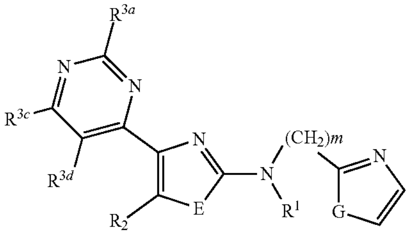

including enantiomers, diastereomers, hydrates, solvates, pharmaceutically acceptable salts, prodrugs and complexes thereof.

The compounds of the present invention include compounds having formula (1U):

(IU)

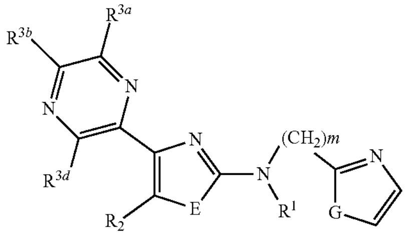

including enantiomers, diastereomers, hydrates, solvates, pharmaceutically acceptable salts, prodrugs and complexes thereof.

The compounds of the present invention include compounds having formula (1W):

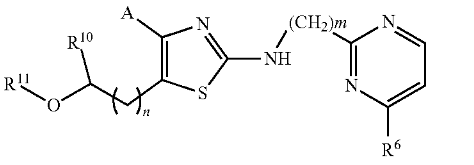

(IW)

including enantiomers, diastereomers, hydrates, solvates, pharmaceutically acceptable salts, prodrugs and complexes thereof.

The compounds of the present invention include compounds having formula (1Y):

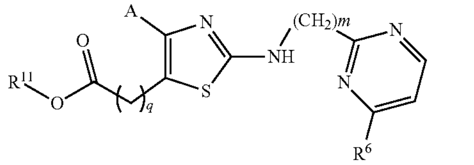

(IY)

including enantiomers, diastereomers, hydrates, solvates, pharmaceutically acceptable salts, prodrugs and complexes thereof.

In some embodiments, A is

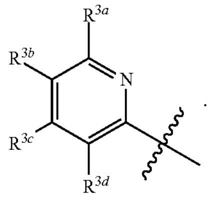

In some embodiments, A is

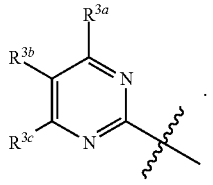

In some embodiments, A is

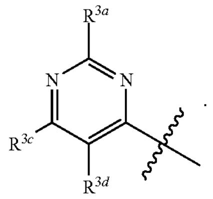

In some embodiments, A is

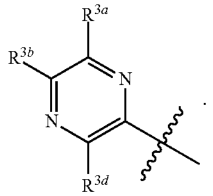

In some embodiments, E is $CR^4{=}CR^5$. In some embodiments, E is sulfur.

In some embodiments, G is $N{=}CR^6$. In some embodiments, G is NH. In some embodiments, G is sulfur.

In some embodiments, X is $(CH_2)_m$. In some embodiments, X is CONH—.

In some embodiments, m is 0. In some embodiments, m is 1. In some embodiments, m is 2. In some embodiments, m is 3. In some embodiments, m is 4.

In some embodiments, $R^1$ is hydrogen. In some embodiments, $R^1$ is

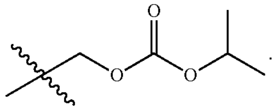 [SMILES: *COC(=O)OC(C)C]

In some embodiments, $R^1$ is

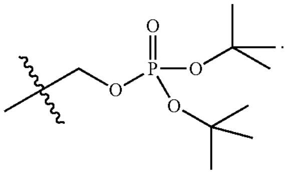 [SMILES: *COP(=O)(OC(C)(C)C)OC(C)(C)C]

In some embodiments, $R^1$ is

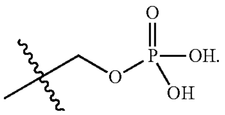 [SMILES: *COP(=O)(O)O]

In some embodiments, $R^1$ is

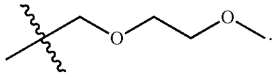 [SMILES: *COCCOC]

In some embodiments, $R^1$ is

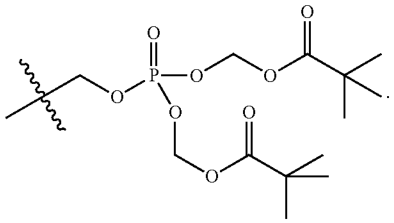 [SMILES: *COP(=O)(OCOC(=O)C(C)(C)C)OCOC(=O)C(C)(C)C]

In some embodiments, $R^1$ is

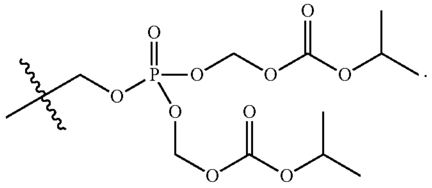 [SMILES: *COP(=O)(OCOC(=O)OC(C)C)OCOC(=O)OC(C)C]

In some embodiments, $R^2$ is hydrogen. In some embodiments, $R^2$ is

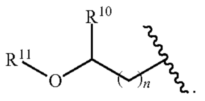

In some embodiments, $R^2$ is

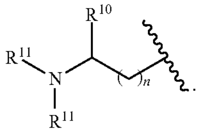

In some embodiments, $R^2$ is

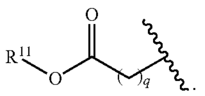

In some embodiments, n is 0. In some embodiments, n is 1.

In some embodiments, q is 0. In some embodiments, q is 1. In some embodiments, q is 2.

In some embodiments, $R^{3a}$ is hydrogen. In some embodiments, $R^{3a}$ is halogen. In some embodiments, $R^{3a}$ is optionally substituted $C_{1-6}$ alkyl. In some embodiments, $R^{3a}$ is optionally substituted $C_{1-6}$ haloalkyl.

In some embodiments, $R^{3b}$ is hydrogen. In some embodiments, $R^{3b}$ is halogen. In some embodiments, $R^{3b}$ is optionally substituted $C_{1-6}$ alkyl. In some embodiments, $R^{3b}$ is optionally substituted $C_{1-6}$ haloalkyl.

In some embodiments, $R^{3c}$ is hydrogen. In some embodiments, $R^{3c}$ is halogen. In some embodiments, $R^{3b}$ is optionally substituted $C_{1-6}$ alkyl. In some embodiments, $R^{3b}$ is optionally substituted $C_{1-6}$ haloalkyl.

In some embodiments, $R^{3d}$ is hydrogen. In some embodiments, $R^{3d}$ is halogen. In some embodiments, $R^{3d}$ is optionally substituted $C_{1-6}$ alkyl. In some embodiments, $R^{3d}$ is optionally substituted $C_{1-6}$ haloalkyl. In some embodiments, $R^{3d}$ is optionally substituted $C_{1-6}$ alkenyl. In some embodiments, $R^{3d}$ is $CO_2R^7$. In some embodiments, $R^{3d}$ is $CONHR^8$. In some embodiments, $R^{3d}$ is $OR^9$.

In some embodiments, $R^4$ is hydrogen. In some embodiments, $R^4$ is halogen. In some embodiments, $R^4$ is optionally substituted $C_{1-6}$ alkyl. In some embodiments, $R^4$ is optionally substituted $C_{1-6}$ haloalkyl. In some embodiments, $R^4$ is optionally substituted $C_{1-6}$ alkenyl. In some embodiments, $R^4$ is $CO_2R^7$. In some embodiments, $R^4$ is $CONHR^8$. In some embodiments, $R^4$ is $OR^9$.

In some embodiments, $R^5$ is hydrogen. In some embodiments, $R^5$ is halogen. In some embodiments, $R^5$ is optionally substituted $C_{1-6}$ alkyl. In some embodiments, $R^5$ is optionally substituted $C_{1-6}$ haloalkyl. In some embodiments, $R^5$ is optionally substituted $C_{1-6}$ alkenyl. In some embodiments, $R^5$ is $CO_2R^7$. In some embodiments, $R^5$ is $CONHR^8$. In some embodiments, $R^5$ is $OR^9$.

In some embodiments, $R^6$ is hydrogen. In some embodiments, $R^6$ is halogen. In some embodiments, $R^6$ is optionally substituted $C_{1-6}$ alkyl.

In some embodiments, $R^6$ is optionally substituted $C_{1-6}$ haloalkyl. In some embodiments, $R^6$ is optionally substituted $C_{1-6}$ alkenyl. In some embodiments, $R^6$ is $CO_2R^7$. In some embodiments, $R^6$ is $CONHR^8$. In some embodiments, $R^6$ is $OR^9$.

In some embodiments, $R^7$ is hydrogen. In some embodiments, $R^7$ is optionally substituted $C_{1-6}$ alkyl.

In some embodiments, $R^8$ is hydrogen. In some embodiments, $R^8$ is optionally substituted $C_{1-6}$ alkyl.

In some embodiments, $R^9$ is hydrogen. In some embodiments, $R^9$ is halogen. In some embodiments, $R^9$ is optionally substituted $C_{1-6}$ alkyl.

In some embodiments, $R^{10}$ is hydrogen. In some embodiments, $R^{10}$ is cyclopropyl. In some embodiments, $R^{10}$ is

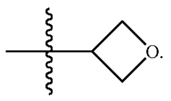 [SMILES: *C1COC1]

In some embodiments, $R^{10}$ is $CF_3$. In some embodiments, $R^{10}$ is $CHF_2$.

In some embodiments, $R^{11}$ is hydrogen. In some embodiments, is optionally substituted $C_{1-6}$ alkyl.

Exemplary embodiments include compounds having the formula (II) or a pharmaceutically acceptable salt form thereof:

(II)

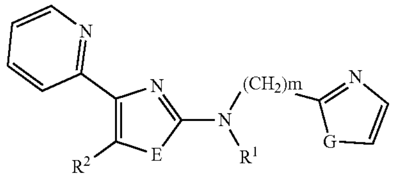

wherein non-limiting examples of $R^1$, $R^2$, $Ar^1$ and $Ar^2$ are defined herein below in Table 1.

TABLE 1

| Exemplary embodiments of compounds of the formula (II): | | | | | | |
|---|---|---|---|---|---|---|
| Entry | E | G | $R^1$ | $R^2$ | m | Structure |
| 1 | CH═CH | N═CH | H | H | 0 | 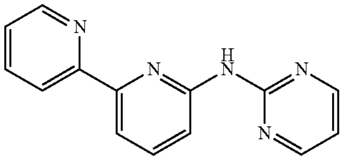 |
| 2 | S | N═CH | H | H | 1 | 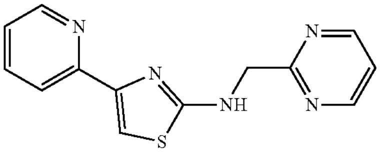 |

Exemplary embodiments include compounds having the formula (III) or a pharmaceutically acceptable salt form thereof:

(III)

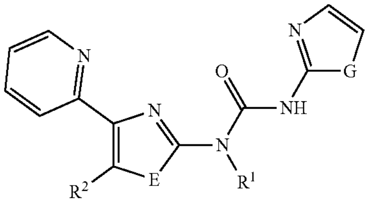

wherein non-limiting examples of $R^1$, $R^2$, E and G are defined herein below in Table 2.

TABLE 2

| Exemplary embodiments of compounds of the formula (III): | | | | | |
|---|---|---|---|---|---|
| Entry | E | G | $R^1$ | $R^2$ | Structure |
| 1 | S | N═CH | H | H | 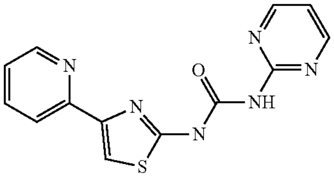 |

Exemplary embodiments include compounds having the formula (IV) or a pharmaceutically acceptable salt form thereof:

(IV)

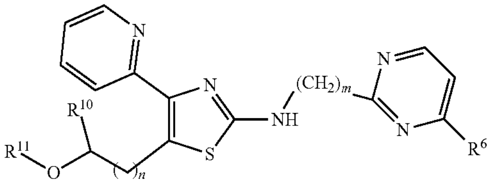

wherein non-limiting examples of $R^1$, $R^2$, E and G are defined herein below in Table 3.

TABLE 3

| Exemplary embodiments of compounds of the formula (IV): | | | | | | |
|---|---|---|---|---|---|---|
| Entry | $R^{10}$ | $R^{11}$ | $R^6$ | n | m | Structure |
| 1 | H | Et | H | 1 | 0 | 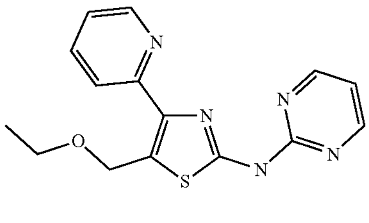 |

TABLE 3-continued

| Exemplary embodiments of compounds of the formula (IV): | | | | | | |
|---|---|---|---|---|---|---|
| Entry | $R^{10}$ | $R^{11}$ | $R^6$ | n | m | Structure |
| 2 | H | Et | Me | 1 | 0 | 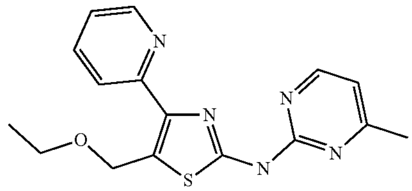 |
| 3 | H | Et | H | 1 | 1 | 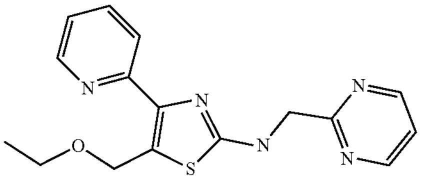 |

Exemplary embodiments include compounds having the formula (V) or a pharmaceutically acceptable salt form thereof:

(V)

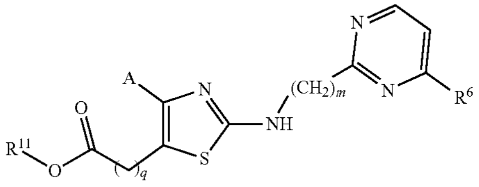

wherein non-limiting examples of $R^1$, $R^2$, E and G are defined herein below in Table 4.

TABLE 4

| Exemplary embodiments of compounds of the formula (V): | | | | | | |
|---|---|---|---|---|---|---|
| Entry | A | $R^6$ | $R^{11}$ | q | m | Structure |
| 1 | 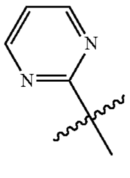 [SMILES: *c1ncccn1] | H | 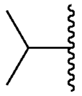 | 0 | 0 | 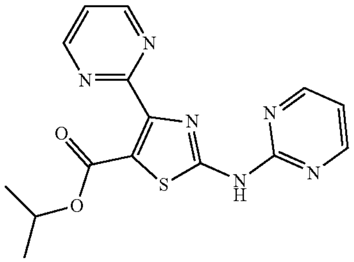 [SMILES: CC(C)OC(=O)c1sc(Nc2ncccn2)nc1-c1ncccn1] |
| 2 | 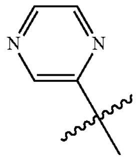 [SMILES: *c1cnccn1] | H | Et | 0 | 0 | 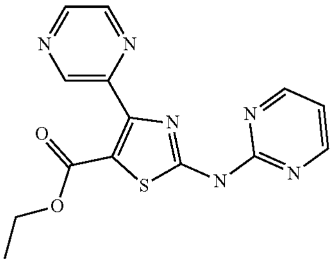 |

TABLE 4-continued
| Exemplary embodiments of compounds of the formula (V): | | | | | | |
|---|---|---|---|---|---|---|
| Entry | A | $R^6$ | $R^{11}$ | q | m | Structure |
| 3 | 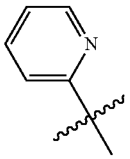 | H | 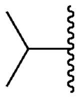 | 0 | 0 | 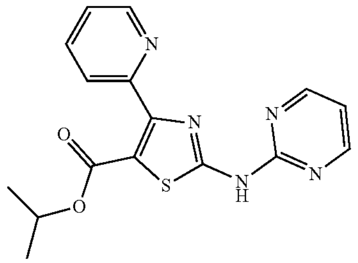 |
| 4 | 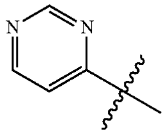 [SMILES: *c1ccncn1] | H | 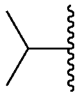 | 0 | 0 | 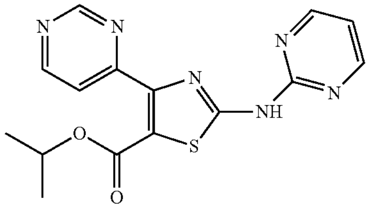 [SMILES: CC(C)OC(=O)c1sc(Nc2ncccn2)nc1-c1ccncn1] |
| 5 | 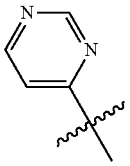 [SMILES: *c1ccncn1] | H | Et | 0 | 0 | 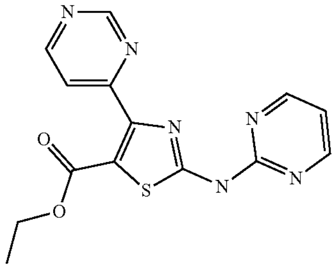 |
| 6 | 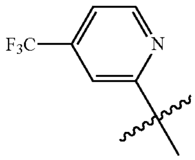 [SMILES: *c1cc(C(F)(F)F)ccn1] | H | Et | 0 | 0 | 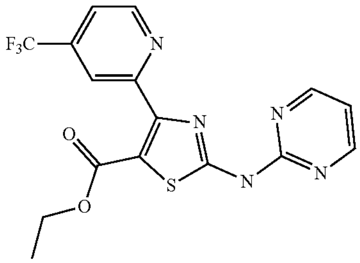 |
| 7 | 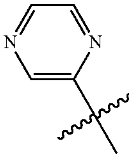 [SMILES: *c1cnccn1] | H | 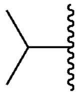 | 0 | 0 | 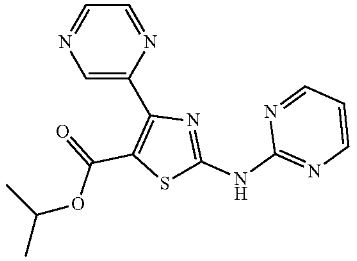 [SMILES: CC(C)OC(=O)c1sc(Nc2ncccn2)nc1-c1cnccn1] |

TABLE 4-continued
Exemplary embodiments of compounds of the formula (V):
| Entry | A | $R^6$ | $R^{11}$ | q | m | Structure |
|---|---|---|---|---|---|---|
| 8 | 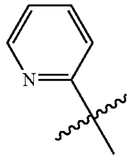 [SMILES: *c1ccccn1] | H | Et | 2 | 0 | 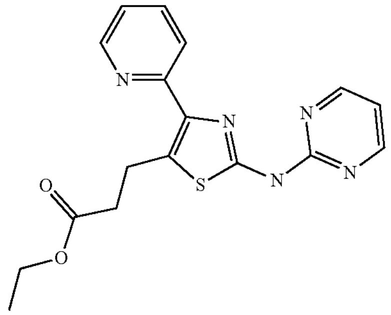 |
| 9 | 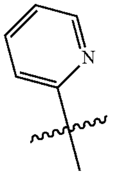 [SMILES: *c1ccccn1] | H | Et | 2 | 1 | 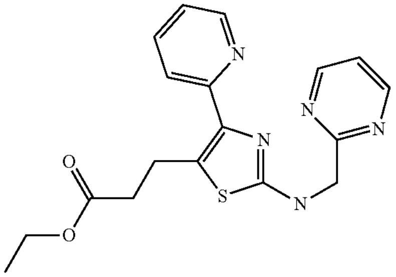 |
| 10 | 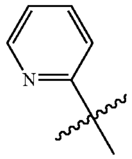 [SMILES: *c1ccccn1] | H | H | 2 | 0 | 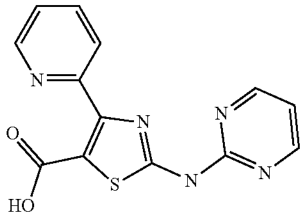 |
| 11 | 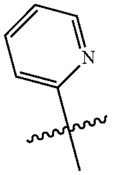 [SMILES: *c1ccccn1] | H | H | 2 | 1 | 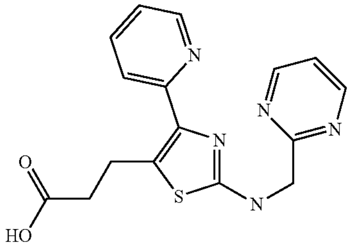 |
| 12 | 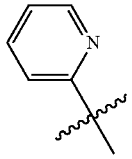 | H | Et | 1 | 0 | 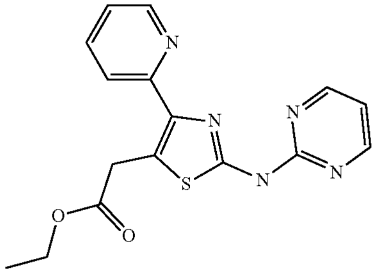 |

TABLE 4-continued
Exemplary embodiments of compounds of the formula (V):
| Entry | A | $R^6$ | $R^{11}$ | q | m | Structure |
|---|---|---|---|---|---|---|
| 13 | 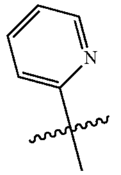 [SMILES: *c1ccccn1] | H | Et | 1 | 1 | 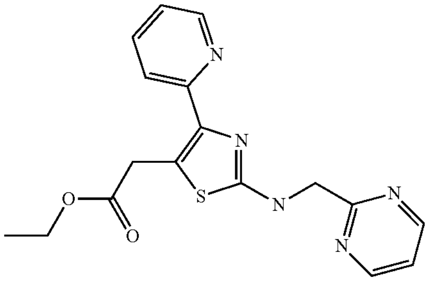 |
| 14 | 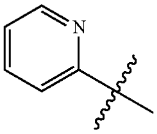 [SMILES: *c1ccccn1] | H | Et | 0 | 1 | 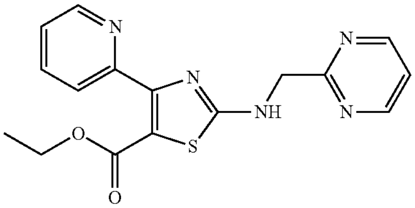 |
| 15 | 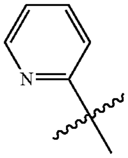 [SMILES: *c1ccccn1] | Me | Et | 1 | 0 | 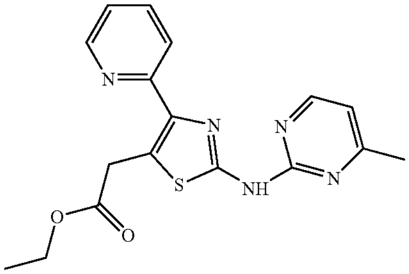 |
| 16 | 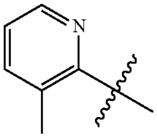 [SMILES: *c1ncccc1C] | Me | Et | 0 | 0 | 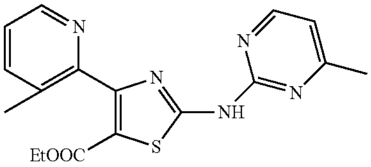 |
| 17 | 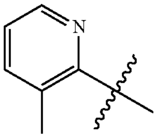 [SMILES: *c1ncccc1C] | H | Et | 0 | 1 | 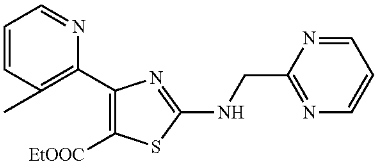 |
Exemplary embodiments include compounds having the formula (VI) or a pharmaceutically acceptable salt form thereof:
(VI)
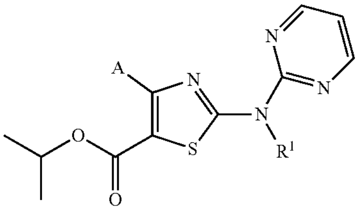
wherein non-limiting examples of $R^1$, $R^2$, E and G are defined herein below in Table 5.

TABLE 5
| Exemplary embodiments of compounds of the formula (VI): | | | |
|---|---|---|---|
| Entry | A | $R^1$ | Structure |
| 1 | 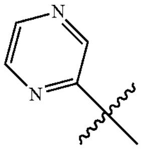 [SMILES: *c1cnccn1] | 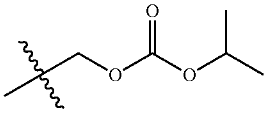 [SMILES: *COC(=O)OC(C)C] | 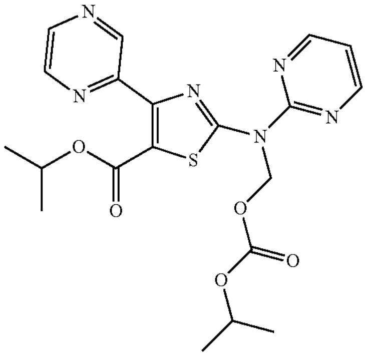 [SMILES: CC(C)OC(=O)OCN(c1ncccn1)c1nc(-c2cnccn2)c(C(=O)OC(C)C)s1] |
| 2 | 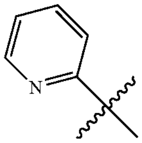 [SMILES: *c1ccccn1] | 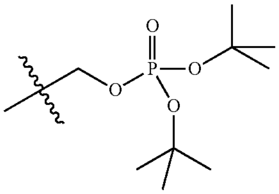 [SMILES: *COP(=O)(OC(C)(C)C)OC(C)(C)C] | 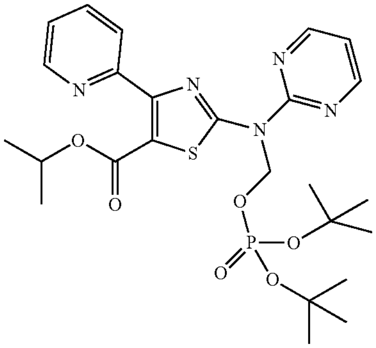 [SMILES: CC(C)OC(=O)c1sc(N(COP(=O)(OC(C)(C)C)OC(C)(C)C)c2ncccn2)nc1-c1ccccn1] |
| 3 | 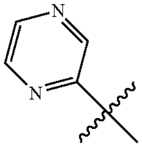 [SMILES: *c1cnccn1] | 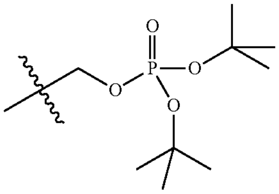 [SMILES: *COP(=O)(OC(C)(C)C)OC(C)(C)C] | 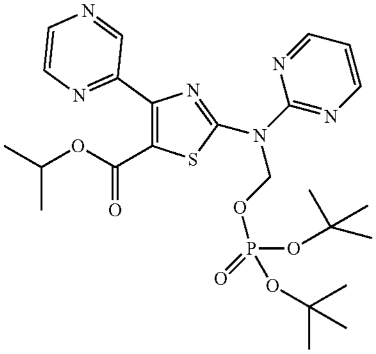 [SMILES: CC(C)OC(=O)c1sc(N(COP(=O)(OC(C)(C)C)OC(C)(C)C)c2ncccn2)nc1-c1cnccn1] |
| 4 | 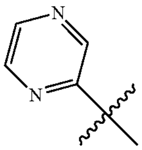 [SMILES: *c1cnccn1] | 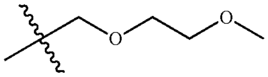 [SMILES: *COCCOC] | 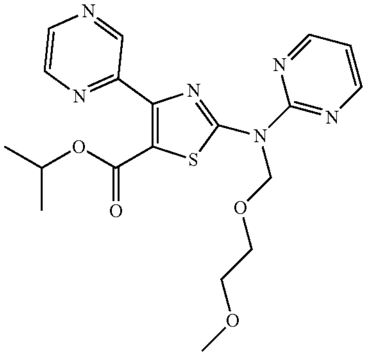 [SMILES: COCCOCN(c1ncccn1)c1nc(-c2cnccn2)c(C(=O)OC(C)C)s1] |

TABLE 5-continued

Exemplary embodiments of compounds of the formula (VI):

| Entry | A | $R^1$ | Structure |
| --- | --- | --- | --- |
| 5 | 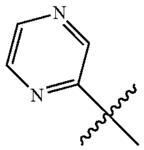 [SMILES: *c1cnccn1] | 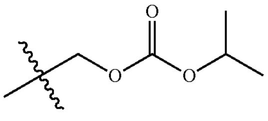 [SMILES: *COC(=O)OC(C)C] | 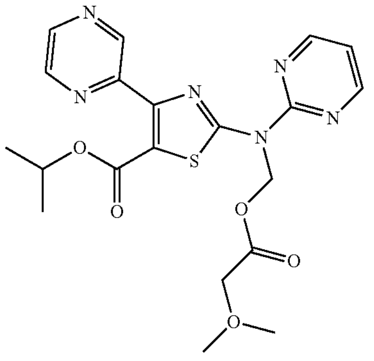 |

For the purposes of demonstrating the manner in which the compounds of the present invention are named and referred to herein, the compound having the formula:

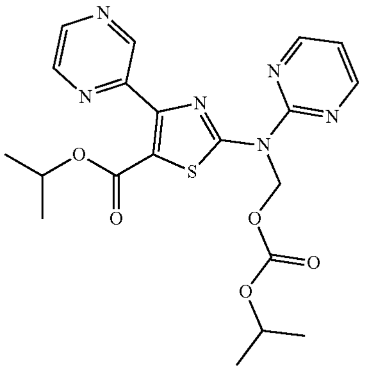 [SMILES: CC(C)OC(=O)OCN(c1ncccn1)c1nc(-c2cnccn2)c(C(=O)OC(C)C)s1]

has the chemical name Isopropyl 2-((((isopropoxycarbonyl)oxy)methyl)(pyrimidin-2-yl)amino)-4-(pyrazin-2-yl)thiazole-5-carboxylate.

For the purposes of demonstrating the manner in which the compounds of the present invention are named and referred to herein, the compound having the formula:

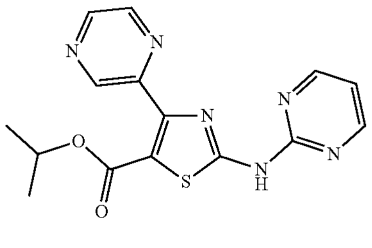 [SMILES: CC(C)OC(=O)c1sc(Nc2ncccn2)nc1-c1cnccn1]

has the chemical name Isopropyl 4-(pyrazin-2-yl)-2-(pyrimidin-2-ylamino)thiazole-5-carboxylate.

For the purposes of the present invention, a compound depicted by the racemic formula, will stand equally well for either of the two enantiomers or mixtures thereof, or in the case where a second chiral center is present, all diastereomers.

In all of the embodiments provided herein, examples of suitable optional substituents are not intended to limit the scope of the claimed invention. The compounds of the invention may contain any of the substituents, or combinations of substituents, provided herein.

Process

The present invention further relates to a process for preparing the compounds of the present invention. Compounds of the present teachings can be prepared in accordance with the procedures outlined herein, from commercially available starting materials, compounds known in the literature, or readily prepared intermediates, by employing standard synthetic methods and procedures known to those skilled in the art of organic chemistry. Standard synthetic methods and procedures for the preparation of organic molecules and functional group transformations and manipulations can be readily obtained from the relevant scientific literature or from standard textbooks in the field. It will be appreciated that where typical or preferred process conditions (i.e., reaction temperatures, times, mole ratios of reactants, solvents, pressures, etc.) are given, other process conditions can also be used unless otherwise stated. Optimum reaction conditions can vary with the particular reactants or solvent used, but such conditions can be determined by one skilled in the art by routine optimization procedures. Those skilled in the art of organic synthesis will recognize that the nature and order of the synthetic steps presented can be varied for the purpose of optimizing the formation of the compounds described herein.

The processes described herein can be monitored according to any suitable method known in the art. For example, product formation can be monitored by spectroscopic means, such as nuclear magnetic resonance spectroscopy (e.g., $^1H$ or $^{13}C$), infrared spectroscopy, spectrophotometry (e.g., UV-visible), mass spectrometry, or by chromatography such as high pressure liquid chromatography (HPLC), gas chromatography (GC), gel-permeation chromatography (GPC), or thin layer chromatography (TLC).

Preparation of the compounds can involve protection and deprotection of various chemical groups. The need for protection and deprotection and the selection of appropriate protecting groups can be readily determined by one skilled in the art. The chemistry of protecting groups can be found, for example, in Greene et al., *Protective Groups in Organic Synthesis,* 2d. Ed. (Wiley & Sons, 1991), the entire disclosure of which is incorporated by reference herein for all purposes.

The reactions or the processes described herein can be carried out in suitable solvents which can be readily selected by one skilled in the art of organic synthesis. Suitable solvents typically are substantially nonreactive with the reactants, intermediates, and/or products at the temperatures at which the reactions are carried out, i.e., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected.

The compounds of these teachings can be prepared by methods known in the art of organic chemistry. The reagents used in the preparation of the compounds of these teachings can be either commercially obtained or can be prepared by standard procedures described in the literature. For example, compounds of the present invention can be prepared according to the method illustrated in the General Synthetic Schemes.

General Synthetic Schemes

The reagents used in the preparation of the compounds of this invention can be either commercially obtained or can be prepared by standard procedures described in the literature. In accordance with this invention, compounds in the genus may be produced by one of the following reaction schemes.

Compounds of formula (I) may be prepared according to the process outlined in Scheme 1. The first aspect of the process of the present invention relates to a process for preparing compounds of the disclosure. Compounds of formula (1I) may be prepared according to the process outlined in the following schemes.

Accordingly, a suitably substituted compound of the formula (1), a known compound or compound prepared by known methods, is reacted with Fmoc-isothiocyanatidate, optionally in the presence an organic solvent such as methylene chloride, dichloroethane, tetrahydronfuran, 1,4-dioxane, N,N-dimethyl formamide, and the like, optionally with heatinhg, optionally with microwave irradiation, to provide a compound of the formula (2). A compound of the formula (2) is reacted with piperidine in a solvent such as methylene chloride, dichloroethane, tetrahydronfuran, 1,4-dioxane, N,N-dimethyl formamide, and the like, optionally with heating, optionally with microwave irradiation, to provide a compound of the formula (3). A compound of the formula (4) is reacted with either phenyltrimethylammonium tribromide (PTAT) in a solvent such as tetrahydrofuran, 1,4-dioxane, N,N-dimethyl formamide, methylene chloride, dichloroethane, and the like, optionally with heating, optionally with microwave irradiation to provide a compound of the formula (5). Alternatively, a compound of the formula (4) is reacted with bromine in a solvent such as tetrahydrofuran, 1,4-dioxane, N,N-dimethyl formamide, methylene chloride, 1,2-dichloroethane, and the like, optionally with heating, optionally with microwave irradiation to provide a compound of the formula (5). A compound of the formula (5) is then reacted with a compound of the formula (3) in a solvent such as methanol, ethanol, isopropanol, ethylene chloride, 1,2-dichloroethane, tetrahydrofuran, 1,4-dioxane, N,N-dimethyl formamide, and the like to provide a compound of the formula (6).

Scheme 1

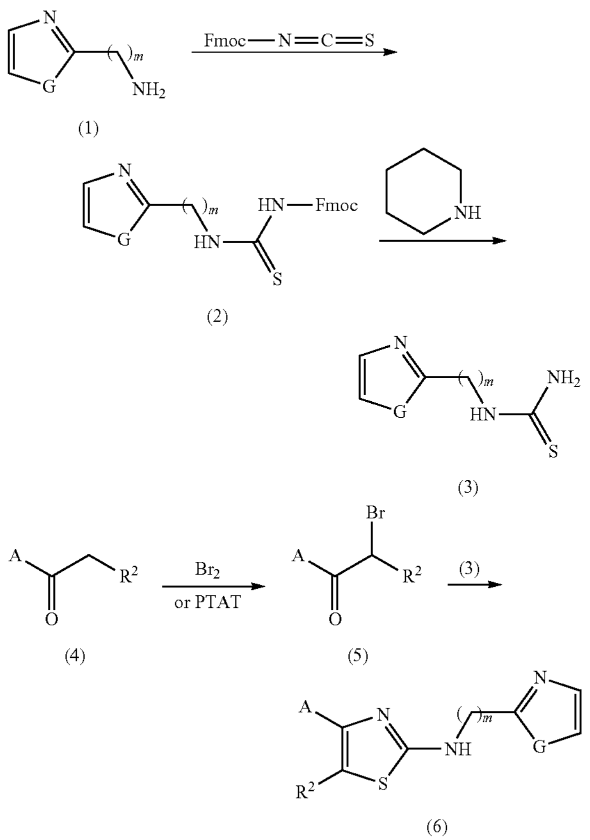

(1) (2) (3) (4) (5) (6)

Scheme 2

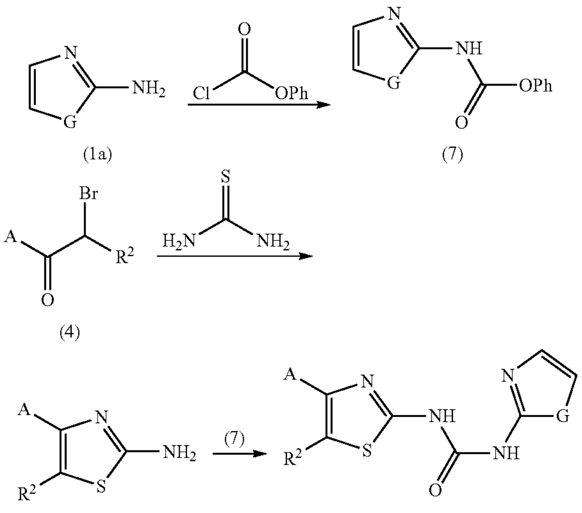

(1a) (7) (4) (8) (9)

A suitably substituted compound of the formula (1a), a known compound or compound prepared by known methods, is reacted with phenyl chloroformate in the presence of a base such as lithium carbonate, sodium carbonate, potassium carbonate, cesium carbonate, triethylamine, diisopropylethylamine, pyridine, 2,6-lutidine, and the like, in an organic solvent such as tetrahydronfuran, 1,4-dioxane, N,N-dimethylformamide, methylene chloride, 1,2-dichloroethane, and the like, optionally with heating, optionally with microwave irradiation, to provide a compound of the formula (7). A compound of the formula (4) is reacted with thiourea in an organic solvent such as ethanol, methanol, isopropanol, methylene chloride, 1,2-dichloroethane, tetrahydrofuran, 1,4-dioxane, N,N-dimethyl formamide, and the like, optionally with heating, optionally with microwave irradiation, to provide a compound of the formula (8). A compound of the formula (8) is reacted with a compound of the formula (7) in an organic solvent such as tetrahydronfuran, 1,4-dioxane, N,N-dimethylformamide, methylene chloride, 1,2-dichloroethane, and the like, to generate a compound of formula (9).

Scheme 3

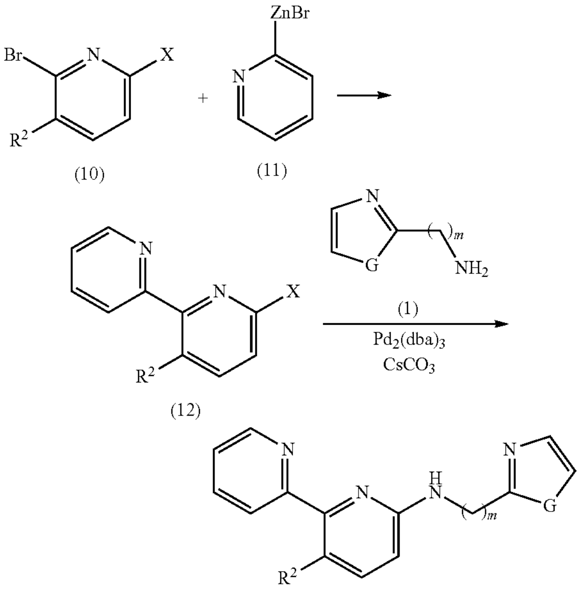

(10) (11) (12) (13)

A compound of the formula (10), a known compound or compound prepared by known methods wherein X is a halogen atom, is reacted with a compound of the formula (11) in the presence of a palladium catalyst such as palladium (II) acetate, tetrakis(triphenylphosphine)palladium(0), dichlorobis (triphenylphosphine)palladium(II), palladium on carbon, bis(acetonitrile)dichloropalladium(II), Tris (dibenzylideneacetone)dipalladium(0) and the like, optionally in the presence of a phosphine ligand such as 4,5-Bis (diphenylphosphino)-9,9-dimethylxanthene (Xantphos), 4,4'-Bi-1,3-benzodioxole-5,5'-diylbis(diphenylphosphane) (SEGPHOS), (2S,3S)-(−)-Bis(diphenylphosphino)butane, (2R,3R)-(+)-Bis(diphenylphosphino)butane, and the like, in an organic solvent such as N,N-dimethyl formamide, N,N-dimethyl acetamide, methanol, ethanol, methylene chloride, 1,2-dichloroethane, tetrahydrofuran, 1,4-dioxane, and the like, optionally with heating, optionally with microwave irradiation, to provide a compound of the formula (12), which is further coupled with compound (1) in the presence of a palladium catalyst such as palladium (II) acetate, tetrakis(triphenylphosphine)palladium(0), dichlorobis (triphenylphosphine)palladium(II), palladium on carbon, bis (acetonitrile)dichloropalladium(II), Tris(dibenzylideneacetone)dipalladium(0) and the like, in the presence of a base such as lithium carbonate, sodium carbonate, potassium carbonate, cesium carbonate, triethylamine, diisopropylethylamine, pyridine, 2,6-lutidine, and the like, in an organic solvent such as N,N-dimethyl formamide, N,N-dimethyl acetamide, methanol, ethanol, methylene chloride, 1,2-dichloroethane, tetrahydrofuran, 1,4-dioxane, and the like, optionally with heating, optionally with microwave irradiation, to provide a compound of the formula (13).

Scheme 4

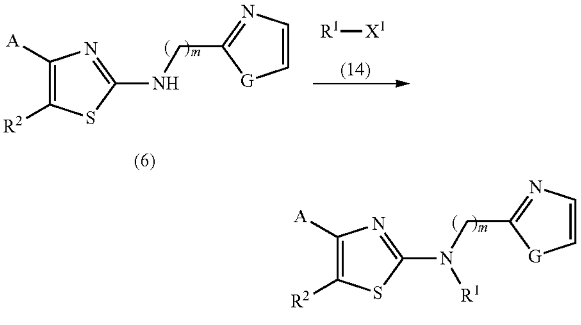

(6) (15)

A compound of the formula (6), is reacted with a compound of the formula (14), a known compound or a compound prepared using known methods wherein $X^1$ is selected from the group consisting of chlorine, bromine, iodine, mesylate, and tosylate, in the presence of a base such as sodium hydride, lithium diisopropylamide, lithium bistrimethylsilylazide, lithium carbonate, sodium carbonate, potassium carbonate, cesium carbonate, triethylamine, diisopropylethylamine, pyridine, 2,6-lutidine, and the like, in an organic solvent such as N,N-dimethyl formamide, N,N-dimethyl acetamide, methylene chloride, 1,2-dichloroethane, tetrahydrofuran, 1,4-dioxane, and the like, optionally with heating, optionally with microwave irradiation, to provide a compound of the formula (15).

Scheme 5

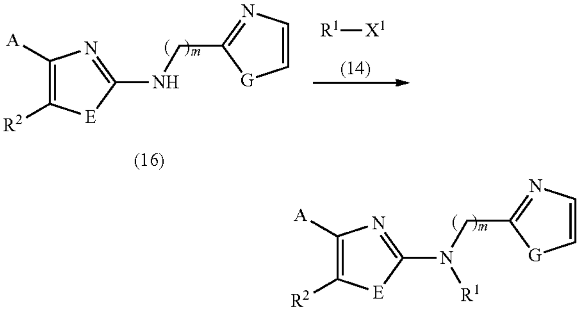

(16) (17)

A compound of the formula (16), is reacted with a compound of the formula (14), a known compound or a compound prepared using known methods wherein $X^1$ is selected from the group consisting of chlorine, bromine, iodine, mesylate, and tosylate, in the presence of a base such as sodium hydride, lithium diisopropylamide, lithium bistrimethylsilylazide, lithium carbonate, sodium carbonate, potassium carbonate, cesium carbonate, triethylamine, diisopropylethylamine, pyridine, 2,6-lutidine, and the like, in an organic solvent such as N,N-dimethyl formamide, N,N-dimethyl acetamide, methylene chloride, 1,2-dichloroethane, tetrahydrofuran, 1,4-dioxane, and the like, optionally with heating, optionally with microwave irradiation, to provide a compound of the formula (17).

EXAMPLES

The Examples provided below provide representative methods for preparing exemplary compounds of the present invention. The skilled practitioner will know how to substitute the appropriate reagents, starting materials and purification methods known to those skilled in the art, in order to prepare the compounds of the present invention.

$^1$H NMR spectra were recorded on a 300 MHz INOVA VARIAN spectrometer. Chemical shifts values are given in ppm and referred as the internal standard to TMS (tetramethylsilane). The peak patterns are indicated as follows: s, singlet; d, doublet; t, triplet; q, quadruplet; m, multiplet and dd, doublet of doublets. The coupling constants (J) are reported in Hertz (Hz). Mass Spectra were obtained on a 1200 Aligent LC-MS spectrometer (ES-API, Positive). Silica gel column chromatography was performed over silica gel 100-200 mesh using the solvent systems described herein.

The examples provides methods for preparing representative compounds of formula (I). The skilled practitioner will know how to substitute the appropriate reagents, starting materials and purification methods known to those skilled in the art, in order to prepare additional compounds of the present invention

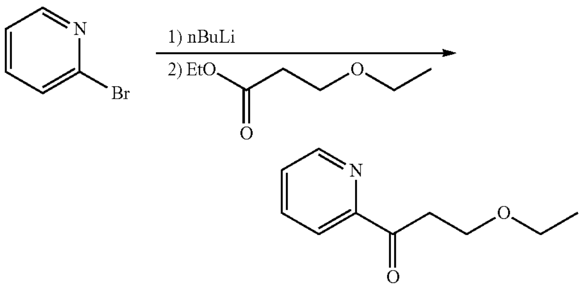

3-Ethoxy-1-(pyridin-2-yl)propan-1-one

2-Bromopyridine (1.0 mL, 10.49 mmol, 1.05 eq) in diethylether (5 ml) was added to n-Butyl Lithium (2.5 M in hexanes, 4.0 ml, 10 mmol, 1 eq) in diethylether at −78° C. The light yellow mixture was stirred at this temperature for 30 minutes before it was transferred into ethyl 3-ethoxypropanoate (20 ml, 129.8 mmol, 13 eq), which was precooled to −78° C., via cannula. The mixture was stirred at this temperature for 1 hour and quenched by addition of saturated ammonium chloride. Ethyl acetate was added and the organic phase was separated and concentrated. The residue was purified on silica gel (120 g) with an eluent of ethyl acetate:hexanes from 1:9 to 1:1 to give a light yellow oil, which solidified on standing (960 mg, 54%). $^1$H NMR (300 MHz, $CDCl_3$): δ 8.73-8.64 (m, 1H), 8.08-8.00 (m, 1H), 7.83 (td, J=7.6, 1.8 Hz, 1H), 7.47 (ddd, J=7.6, 4.7, 1.2 Hz, 1H), 3.89 (t, J=6.4 Hz, 2H), 3.60-3.44 (m, 4H), 1.18 (t, J=7.0 Hz, 3H); Calculated for C10H13NO2, 179.09; MS (ESI) (m/z) observed 180.2 $(M+1)^+$.

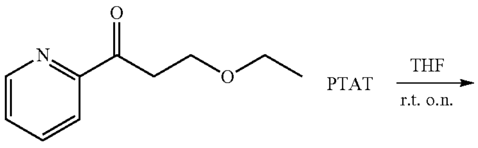

-continued

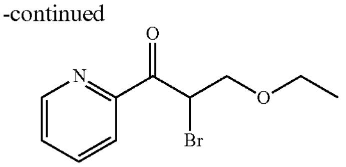

2-bromo-3-ethoxy-1-(pyridin-2-yl)propan-1-one

To a solution of 3-ethoxy-1-(pyridin-2-yl)propan-1-one (100 mg, 0.56 mmol) in tetrahydrofuran (4 ml) was added phenyltrimethylammonium tribromide (PTAT, 215 mg, 0.57 mmol) under argon. The mixture was stirred at 25° C. overnight, and diluted with 30 ml ethyl acetate, washed it with saturated $NaHCO_3$, brine, dried over sodium sulfate, filtered, and stripped of solvent under vacuum. The crude was purified by ISCO (10-20% Ethyl acetate in hexanes) to afford product as a colorless oil (120 mg, 84-96%). $^1$H NMR (300 MHz, $CDCl_3$): 8.72 (d, J=4.7 Hz, 1H), 8.11 (d, J=5.9 Hz, 1H), 7.87 (t, J=5.9 Hz, 1H), 7.51 (t, J=3.5 Hz, 1H), 6.06 (dd, J=5.7 Hz, 2.4 Hz, 1H), 4.17 (dd, J=8.2 Hz, 2.5 Hz, 1H), 3.94 (q, J=5.6 Hz, 1H), 3.59 (q, 7.0 Hz, 2H), 1.16 (t, J=5.0 Hz, 3H); Calculated for C10H12BrNO2, 257/259; MS (ESI) (m/z) observed 258/260 $(M+1)^+$.

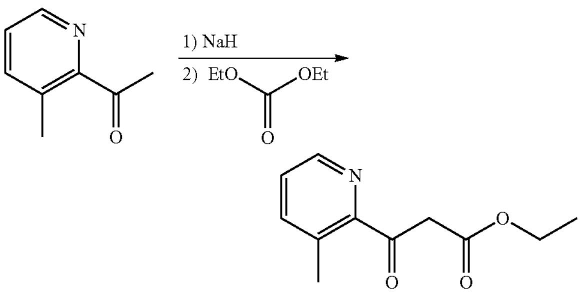

Ethyl 3-(3-methylpyridin-2-yl)-3-oxopropanoate

To a stirred solution of 1-(3-methylpyridin-2-yl)ethanone (500 mg, 3.70 mmol, 1 eq) in diethyl carbonate (30 ml) was added NaH (60% in oil, 887.6 mg, 22.2 mmol, 6 eq) protionwise at 25° C. The grey suspension was then stirred at 90° C. for 4 hours. Acetic acid (2.1 ml) in diethyl ether (21 ml) was added dropwise to quench the reaction. The resulting mixture was filtered through a pad of celite. The filtrate was concentrated and purified on silica gel (80 g) with a gradient of ethyl acetate in hexances from 0:1 to 3:7 to give a dark brown oil (650 mg, 85%). $^1$H NMR (300 MHz, $CDCl_3$): δ 8.52-8.46 (m, 1H), 7.63-7.59 (m, 1H), 7.35 (dd, J=7.9, 4.5 Hz, 1H), 4.24-4.10 (m, 4H), 2.63 (s, 3H), 1.23 (t, J=7.0 Hz, 3H); Calculated for C11H13NO3, 207.09; MS (ESI) (m/z) observed 208.2 $(M+1)^+$.

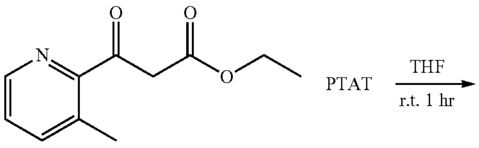

-continued

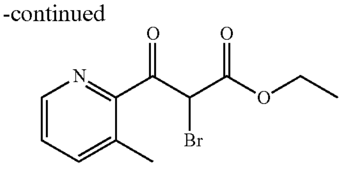

Ethyl 2-bromo-3-(3-methylpyridin-2-yl)-3-oxopropanoate

The title compound was prepared according to the procedure of 2-bromo-3-ethoxy-1-(pyridin-2-yl)propan-1-one. (100%). Calculated for C11H12BrNO3, 285/287; MS (ESI) (m/z) observed 286/288 $(M+1)^+$. NMR (300 MHz, $CDCl_3$, ppm): δ8.41 (d, J=4.4 Hz, 1H), 7.58 (d, J=7.3 Hz, 1H), 7.32 (t, J=4.7 Hz, 1H), 6.15 (s, 1H), 4.15 (q, J=7.0 Hz, 2H), 2.57 (s, 3H), 1.15 (t, 7.3 Hz, 3H).

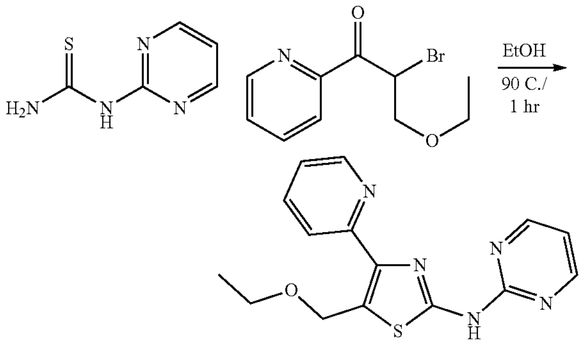

5-(ethoxymethyl)-4-(pyridin-2-yl)-N-(pyrimidin-2-yl)thiazol-2-amine

A suspension of 1-(pyrimidin-2-yl)thiourea (40 mg, 0.26 mmol) and 2-bromo-3-ethoxy-1-(pyridin-2-yl)propan-1-one (80 mg, 0.31 mmol) in ethanol (2 ml) was heated in a 20 ml vial at 90° C. for 1 hour. The reaction was cooled, filtered and washed with ethyl acetate, dichloromethane and methanol (2 ml each), and dried to afford product as white powder (60 mg, 74%). Calculated for C15H15N5OS, 313.38; MS (ESI) (m/z) observed 314.2 $(M+1)^+$. $^1$H NMR (300 MHz, DMSO, ppm): δ 11.72 (s, 1H), 8.66 (d, J=4.7 Hz, 3H), 8.02 (d, J=8.2 Hz, 1H), 7.89 (t, J=5.9 Hz, 1H), 7.31 (t, J=5.9 Hz, 1H), 7.05 (t, J=4.7 Hz, 1H), 5.15 (s, 2H), 3.59 (q, J=6.8 Hz, 2H), 1.18 (t, J=7.0 Hz, 3H).

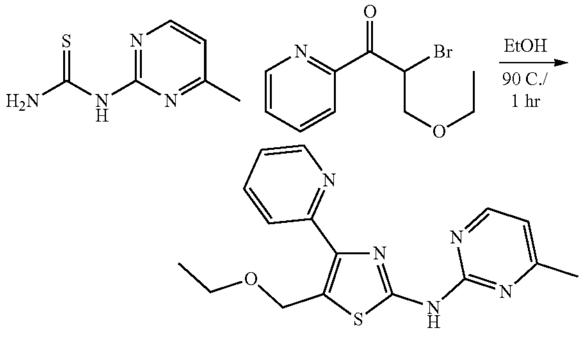

5-(ethoxymethyl)-N-(4-methylpyrimidin-2-yl)-4-(pyridin-2-yl)thiazol-2-amine

The title compound was prepared according to the procedure of 5-(ethoxymethyl)-4-(pyridin-2-yl)-N-(pyrimidin-2-yl)thiazol-2-amine to afford product as white powder (40%). Calculated for C16H17N5OS, 327.40; MS (ESI) (m/z) observed 328.2 $(M+1)^+$. $^1$H NMR (300 MHz, DMSO, ppm): δ11.61 (s, 1H), 8.62 (s, 1H), 8.50 (s, 1H), 8.00 (s, 1H), 7.89 (s, 1H), 7.30 (s, 1H), 6.93 (s, 1H), 5.15 (s, 2H), 3.58 (d, J=5.6 HZ, 2H), 2.45 (s, 3H), 1.18 (s, 3H).

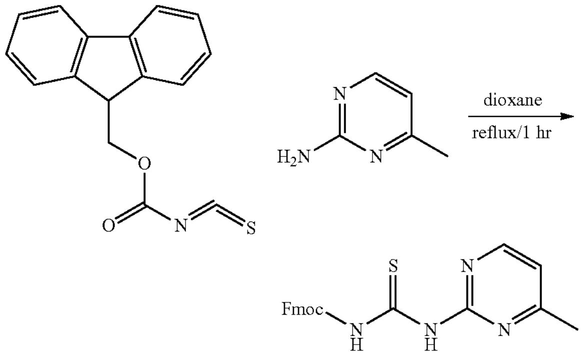

1-Fmoc-3-(4-methylpyrimidin-2-yl)thiourea

A solution of Fmoc-isothiocyanate (2.87 g, 10.0 mmol) and 2-amino-4-methylpyrimidine (1.09 g, 10 mmol) in 50 ml 1,4-dioxane was refluxed under argon. A lot of white solid was generated in minutes. The reaction was stopped at 1 hour. The reaction was cooled, the mixture was filtered, and the solid was washed with cold methanol (40 ml) and dried to afford product (3.30 g, 85%). Calculated for C21H18N4O2S, 390.46; MS (ESI) (m/z) observed 391 $(M+1)^+$.

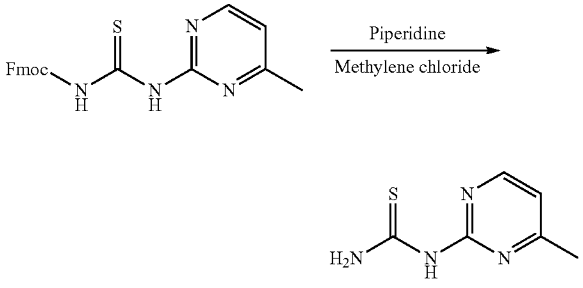

1-(4-methylpyrimidin-2-yl)thiourea

To a suspension of 1-Fmoc-3-(4-methylpyrimidin-2-yl) thiourea (3.30 g, 8.46 mmol) in 60 ml dichloromethane was added piperidine (12 ml). The mixture was stirred at 25° C. for 2 hours and filtered, washed with dichloromethane (10 ml) and water (10 ml), and air-dried to afford white powder product (1.32 g, 93%). Calculated for C6H8N4S, 168.22; MS (ESI) (m/z) observed 169 $(M+1)^+$.

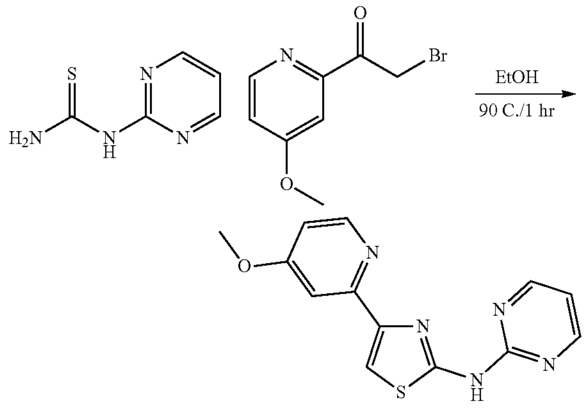

4-(4-methoxypyridin-2-yl)-N-(pyrimidin-2-yl)thiazol-2-amine

A suspension of 1-(pyrimidin-2-yl)thiourea (46 mg, 0.30 mmol) and 2-bromo-1-(4-methoxypyridin-2-yl)ethanone (76 mg, 0.33 mmol) in ethanol (2 ml) was heated in a 20 ml vial at 90° C. for 1 hour. The reaction was cooled, and filtered. The filtrate was washed with ethyl acetate, dichloromethane and methanol (2 ml each), and dried to afford the title compound as pale gray powder (56 mg, 66%). Calculated for C13H11N5OS, 285.32; MS (ESI) (m/z) observed 286 $(M+1)^+$. $^1$H NMR (300 MHz, DMSO, ppm): δ11.86 (s, 1H), 8.66 (d, J=5.0 Hz, 2H), 8.41 (d, J=5.6 Hz, 1H), 7.74 (s, 1H), 7.54 (d, J=2.6 Hz, 1H), 7.06 (t, J=4.9 Hz, 1H), 6.91 (q, J=3.6 Hz, 1H), 3.88 (s, 3H).

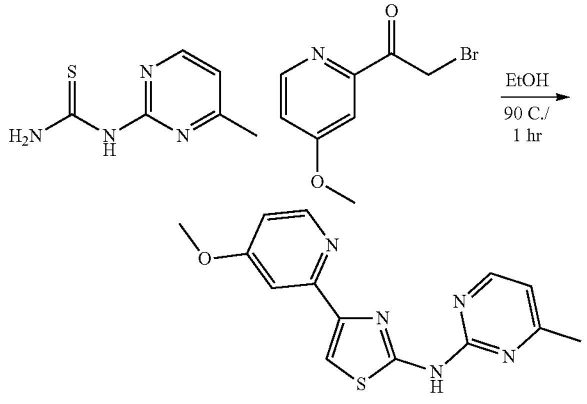

4-(4-methoxypyridin-2-yl)-N-(4-methylpyrimidin-2-yl)thiazol-2-amine

The title compound was prepared according to the procedure of 4-(4-methoxypyridin-2-yl)-N-(pyrimidin-2-yl)thiazol-2-amine to afford off-white product in 70% yield. Calculated for C14H13N5OS, 299.35; MS (ESI) (m/z) observed 300 $(M+1)^+$. $^1$H NMR (300 MHz, DMSO, ppm): δ11.74 (s, 1H), 8.50 (d, J=5.0 Hz, 1H), 8.41 (d, J=5.5 Hz, 1H), 7.72 (s, 1H), 7.54 (d, J=2.4 Hz, 1H), 6.91 (m, 2H), 3.88 (s, 3H), 2.45 (s, 3H).

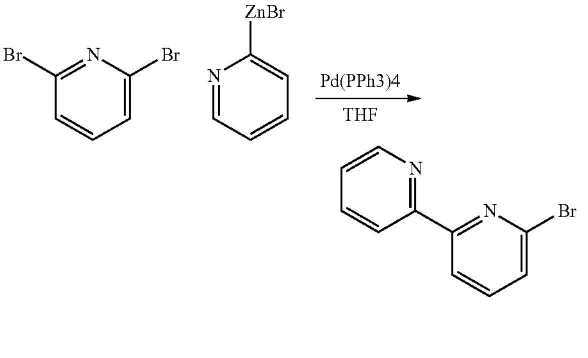

6-bromo-2,2'-bipyridine

To a solution of 2,6-dibromopyridine (474 mg, 2 mmol) in tetrahydrofuran (5 ml) was added $Pd(PPh_3)_4$ (23 mg, 0.02 mmol) under argon, and then a solution of pyridin-2-ylzinc (II) bromide (0.5M in tetrahydrofuran, 4.4 ml, 2.2 mmol). The mixture was stirred at 25° C. over a weekend, and then diluted with 150 ml ethyl acetate. The solution was washed with saturated ammonium chloride (20 ml×5) and brine. The organic phase was dried over $Na_2SO_4$, filtered, and the solvents were removed under vacuum. The product was purified by ISCO chromatography (10-30% Ethyl acetate in hexanes) to afford the title compound as a white solid (154 mg, 33%). Calculated for C10H7BrN2, 233.98/235.98; MS (ESI) (m/z) observed 235/237 $(M+1)^+$. $^1$H NMR (300 MHz, $CDCl_3$, ppm): δ8.67 (d, J=5.9 Hz, 1H), 8.40 (t, J=7.9 Hz, 2H), 7.82 (t, J=7.6 HZ, 1H), 7.67 (t, J=8.0 Hz, 1H), 7.50 (d, J=7.9 Hz, 1H), 7.33 (t, J=5.0 Hz 1H).

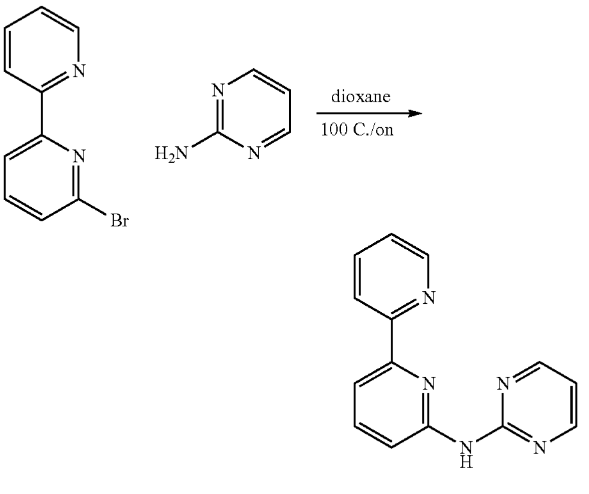

N-(pyrimidin-2-yl)-[2,2'-bipyridin]-6-amine

A mixture of 6-bromo-2,2'-bipyridine (30 mg, 0.13 mmol), 2-aminopyrimidine (15 mg, 0.15 mmol), Cesium carbonate (104 mg, 0.32 mmol), Xant-phos (7.5 mg, 0.013 mmol), and Tris(dibenzylideneacetone)dipalladium(0) (6 mg, 0.0064 mmol) in 1,4-dioxane (5 ml) was heated at 100° C. under argon overnight. After cooling, the mixture was directly loaded on a 12 g silica gel column and eluted with 5-10% methanol in dichloromethane to afford 30 mg white solid, which was slurried with 5 ml acetonitrile and filtered to obtain the title compound (20 mg, 63%). Calculated for C14H11N5, 249.27; MS (ESI) (m/z) observed 250.2 $(M+1)^+$. $^1$H NMR (300 MHz, $CDCl_3$, ppm): δ8.69 (d, J=5.9 Hz, 1H), 8.53 (d, J=5.0 Hz, 2H), 8.45 (d, J=8.5 Hz, 1H), 8.33 (d, J=7.9 Hz, 1H), 8.25 (sb, 1H), 8.03 (d, J=6.7 Hz, 1H), 7.82 (q, J=8.2 Hz, 2H), 7.30 (t, J=4.7 Hz, 1H), 6.82 (t, J=4.98 Hz, 1H).

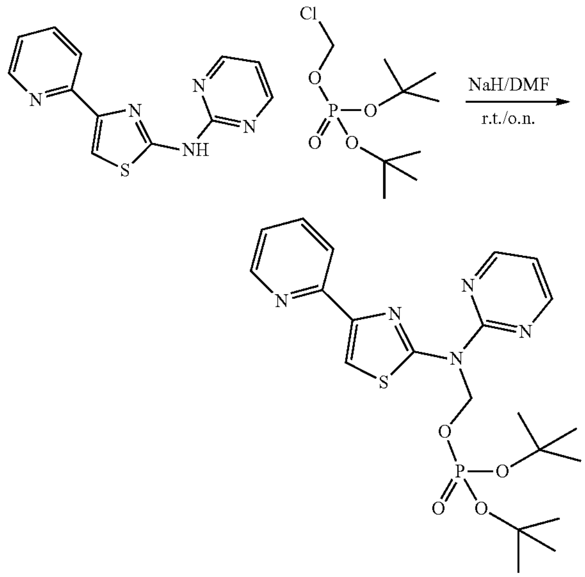

di-tert-butyl(((4-(pyridin-2-yl)thiazol-2-yl)(pyrimidin-2-yl)amino)methyl) phosphate (Method 1) To a solution of 4-(pyridin-2-yl)-N-(pyrimidin-2-yl)thiazol-2-amine (40 mg, 0.16 mmol) in 2 ml N,N-dimethyl formamide was added 60% sodium hydride in mineral oil (16 mg, 0.4 mmol) under argon. After 30 minutes, a solution of di-tert-butyl (chloromethyl) phosphate (62 mg, 0.24 mmol) in N,N-dimethyl formamide (1 ml) was added dropwise. The mixture was stirred under argon at 25° C. over night. The reaction was quenched with 30 ml water and extracted with ethyl acetate (30 ml×3). Combined organic phases was washed with brine, dried over $Na_2SO_4$, filtered, and stripped of solvent under vacuum. The product was obtained by silica gel chromatography (0-20% ethyl acetate in hexanes) as light yellow oil (60 mg, 79%). Calculated for C21H28N5O4PS, 477.52; MS (ESI) (m/z) observed 478.3 $(M+1)^+$. $^1$H NMR (300 MHz, $CDCl_3$, ppm): δ 8.66 (d, J=4.7 Hz, 2H), 8.59 (d, J=4.7 Hz, 1H), 8.27 (d, J=8.0 Hz, 1H), 7.76 (m, 2H), 7.19 (t, J=1.8 Hz, 1H), 7.00 (t, J=4.7 Hz, 1H), 6.70 (d, J=5.6 Hz, 2H), 1.50 (s, 9H), 1.46 (s, 9H).

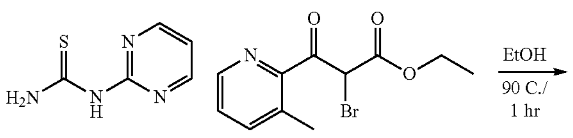

-continued

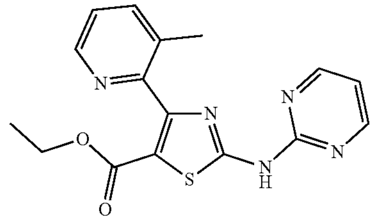

Ethyl 4-(3-methylpyridin-2-yl)-2-(pyrimidin-2-ylamino)thiazole-5-carboxylate

The title compound was prepared according to the procedure of 4-(4-methoxypyridin-2-yl)-N-(pyrimidin-2-yl)thiazol-2-amine (39%). Calculated for C16H15N5O2S, 341.39; MS (ESI) (m/z) observed 342.2 $(M+1)^+$. $^1$H NMR (300 MHz, CDCl3, ppm): δ 9.61 (s,b, 1NH), 8.67 (d, J=5.0 Hz, 2H), 8.53 (d, J=3.8 Hz, 1H), 7.59 (d, J=7.0 Hz, 1H), 7.26 (t, J=5.0 Hz, 1H), 6.98 (t, J=5.0 Hz, 1H), 4.18 (q, J=7.3 Hz, 2H), 2.24 (s, 3H), 1.17 (t, J=7.0 Hz, 3H).

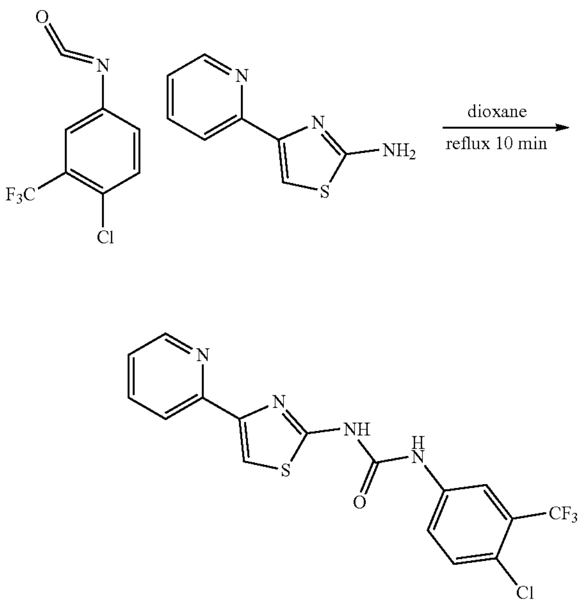

1-(4-chloro-3-(trifluoromethyl)phenyl)-3-(4-(pyridin-2-yl)thiazol-2-yl)urea

A mixture of 4-(pyridin-2-yl)thiazol-2-amine (50 mg, 0.28 mmol) and 1-chloro-4-isocyanato-2-(trifluoromethyl) benzene (63 mg, 0.28 mmol) in 5 ml 1,4-dioxane was refluxed for 10 minutes. The mixture was concentrated to half volume and diluted with ether (10 ml). The reaction was filtered and the filtrate was washed the white solid with ether and dried to afford the title compound (70 mg, 63%). Calculated for C16H10ClF3N4OS, 398.02; MS (ESI) (m/z) observed 399.1 $(M+1)^+$. $^1$H NMR (300 MHz, DMSO, ppm): δ 11.03 (s,b, 1NH), 9.38 (s,b, 1NH), 8.61 (d, J=4.4 Hz, 1H), 8.10 (s, 1H), 7.85-7.96 (m, 2H), 7.65-7.78 (m, 3H), 7.34 (t, J=5.9 Hz, 1H).

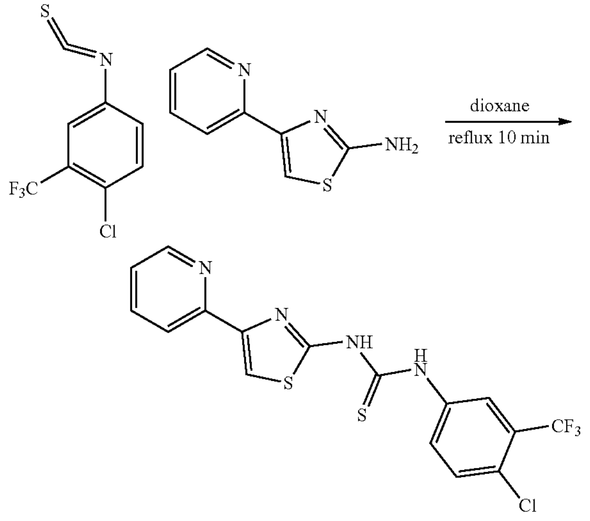

1-(4-chloro-3-(trifluoromethyl)phenyl)-3-(4-(pyridin-2-yl)thiazol-2-yl)thiourea

A solution of 4-(pyridin-2-yl)thiazol-2-amine (50 mg, 0.28 mmol) and 1-chloro-4-isothiocyanato-2-(trifluoromethyl)benzene (67 mg, 0.28 mmol) in 5 ml 1,4-dioxane was refluxed for 10 minutes. The reaction was stripped of solvent and the resulting material was purified by ISCO chromatography, eluted with 0-10% methanol in dichloromethane to provide 70 mg light yellow solid, which was treated with 2 ml MeOH and filtered to afford white solid product (23 mg, 20%). Calculated for C16H10ClF3N4S2, 414.00; MS (ESI) (m/z) observed 415.1 $(M+1)^+$. $^1H$ NMR (300 MHz, DMSO, ppm): δ8.65 (s, 1H), 8.16 (s, 1H), 7.90-8.03 (m, 3H), 7.65-7.78 (m, 2H), 7.39 (s, 1H).

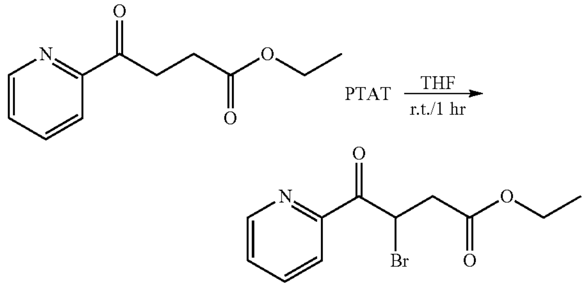

ethyl 3-bromo-4-oxo-4-(pyridin-2-yl)butanoate

The title compound was prepared according to the procedure of 2-bromo-3-ethoxy-1-(pyridin-2-yl)propan-1-one (100%). Calculated for C11H12BrNO3, 285/287; MS (ESI) (m/z) observed 286/288 $(M+1)^+$. $^1H$ NMR (300 MHz, CDCl3, ppm): δ 8.75 (d, J=3.8 Hz, 1H), 8.13 (d, J=7.9 Hz, 1H), 7.91 (t, J=7.6 Hz, 1H), 7.51 (t, J=6.8 Hz, 1H), 6.25 (dd, J=5.8 Hz/3.8 Hz, 1H), 4.13 (q, J=7.3 Hz, 2H), 3.49 (dd, J=9.4 Hz/7.6 Hz, 1H), 3.15 (dd, J=5.8 Hz/11.5 Hz, 1H), 1.21 (t, J=7.3 Hz, 3H).

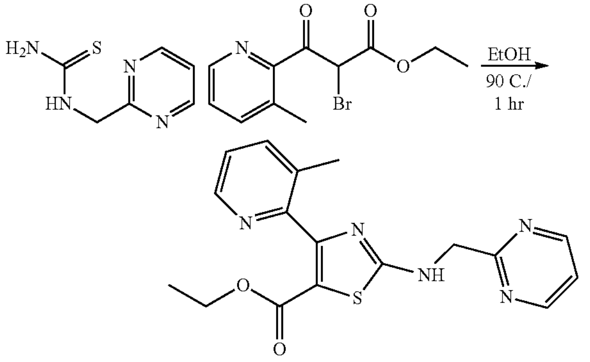

Ethyl 4-(3-methylpyridin-2-yl)-2-((pyrimidin-2-ylmethyl)amino)thiazole-5-carboxylate The title compound was prepared according to the procedure of 4-(4-methoxypyridin-2-yl)-N-(pyrimidin-2-yl)thiazol-2-amine. (62%). Calculated for C17H17N5O2S, 355.11; MS (ESI) (m/z) observed 356.2 $(M+1)^+$. $^1H$ NMR (300 MHz, CDCl3, ppm): δ 8.75 (d, J=5.0 Hz, 2H), 8.50 (d, J=3.8 Hz, 1H), 7.56 (d, J=7.0 Hz, 1H), 7.23 (m, 1H), 7.08 (sb, 1H), 4.76 (s, 2H), 4.10 (q, J=7.1 Hz, 2H), 2.25 (s, 3H), 1.10 (t, J=7.1 Hz, 3H).

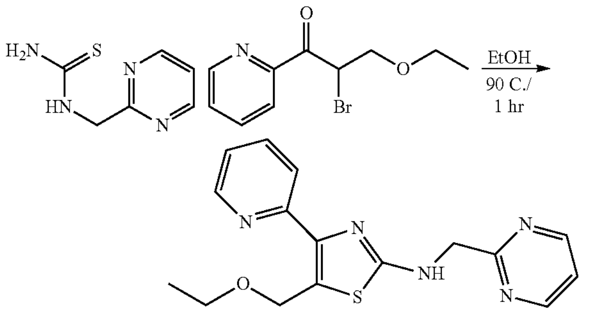

5-(ethoxymethyl)-4-(pyridin-2-yl)-N-(pyrimidin-2-ylmethyl)thiazol-2-amine

The title compound was prepared according to the procedure of 4-(4-methoxypyridin-2-yl)-N-(pyrimidin-2-yl)thiazol-2-amine (69%). Calculated for C16H17N5OS, 327.12; MS (ESI) (m/z) observed 328.2 $(M+1)^+$. $^1H$ NMR (300 MHz, CDCl3, ppm): δ 8.75 (d, J=4.7 Hz, 2H), 8.59 (d, J=4.7 Hz, 1H), 7.98 (d, J=7.9 Hz, 1H), 7.72 (t, J=7.6 Hz, 1H), 7.25 (t, 6.8 Hz, 1H), 7.12 (t, J=7.3 Hz, 1H), 6.33 (sb, 1NH), 5.12 (s, 2H), 4.81 (d, J=5.0 Hz, 2H), 3.61 (q, J=7.1 Hz, 2H), 1.24 (t, J=7.0 Hz, 3H).

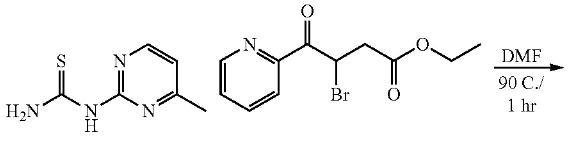

-continued

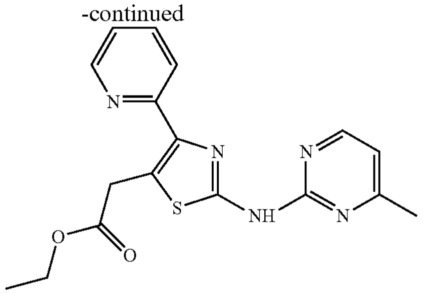

Ethyl 2-(2-((4-methylpyrimidin-2-yl)amino)-4-(pyridin-2-yl)thiazol-5-yl)acetate

A solution of 1-(4-methylpyrimidin-2-yl)thiourea (45 mg, 0.27 mmol) and ethyl 3-bromo-4-oxo-4-(pyridin-2-yl)butanoate (87 mg, 0.30 mmol) in 4 ml N,N-dimethyl formamide was heated at 90° C. for 1 hour. After cooling, ethyl acetate (50 ml) was added. The solution was washed with water, saturated sodium bicarbonate and brine, then dried over sodium sulfate, filtered, and stripped of solvent. The crude material was purified by ISCO chromatography, eluted with 60-100% ethyl acetate in hexanes to afford light yellow solid product (64 mg, 67%). Calculated for C17H17N5O2S, 355.11; MS (ESI) (m/z) observed 356.2 $(M+1)^+$. $^1$H NMR (300 MHz, DMSO, ppm): δ 11.65 (s, 1H), 8.54 (d, J=3.8 Hz, 1H), 8.48 (d, J=5.0 Hz, 1H), 8.03 (d, J=7.9 Hz, 1H), 7.88 (td, J=7.6 Hz/1.8 Hz, 1H), 7.28 (t, J=6.1 Hz, 1H), 6.93 (d, J=5.0 Hz, 1H), 4.38 (s, 2H), 4.08 (q, J=7.0 Hz, 2H), 2.47 (s, 3H), 1.17 (t, J=7.0 Hz, 3H).

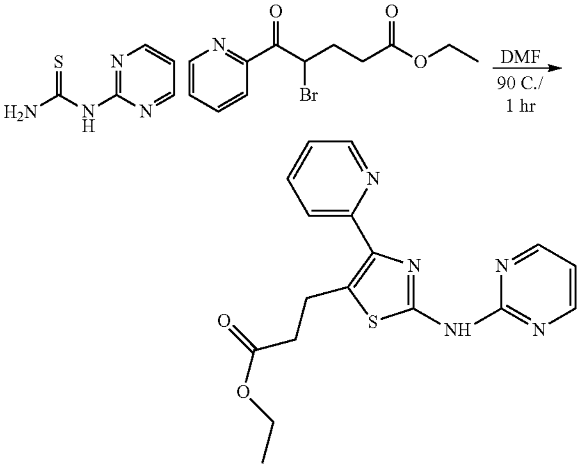

Ethyl 3-(4-(pyridin-2-yl)-2-(pyrimidin-2-ylamino)thiazol-5-yl)propanoate

Prepared by the same method as above. Calculated for C17H17N5O2S, 355.11; MS (ESI) (m/z) observed 356.2 $(M+1)^+$. $^1$H NMR (300 MHz, d6-DMSO, ppm): δ8.74 (d, J=5.0 Hz, 1H), 8.72 (d, J=4.7 Hz, 2H), 8.20 (t, J=7.3 Hz, 1H), 8.14 (d, J=7.6 Hz, 1H), 7.59 (t, J=6.2 Hz, 1H), 7.08 (t, J=5.0 Hz, 1H), 4.04 (q, J=7.3 Hz, 2H), 3.42 (t, J=7.3 Hz, 2H), 2.74 (t, J=7.4 Hz, 2H), 1.15 (t, J=7.1 Hz, 3H).

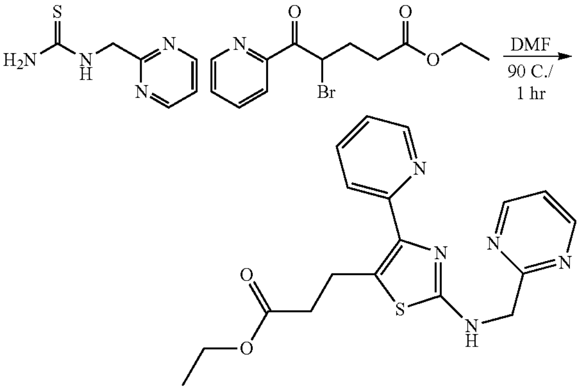

Ethyl 3-(4-(pyridin-2-yl)-2-((pyrimidin-2-ylmethyl)amino)thiazol-5-yl)propanoate The title compound was prepared according to the procedure of Ethyl 2-(2-((4-methylpyrimidin-2-yl)amino)-4-(pyridin-2-yl)thiazol-5-yl)acetate. Calculated for C18H19N5O2S, 369.13; MS (ESI) (m/z) observed 370.2 $(M+1)^+$. $^1$H NMR (300 MHz, CDCl3, ppm): δ 8.75 (d, J=5.0 Hz, 2H), 8.56 (d, J=6.8 Hz, 1H), 7.96 (d, J=9.0 Hz, 1H), 7.69 (t, 9.4 Hz, 1H), 7.24 (t, J=9.7 Hz, 1H), 7.12 (t, 1H), 6.24 (t, J=7.0 Hz, 1H), 4.80 (d, J=5.0 Hz, 2H), 4.13 (q, J=7.1 Hz, 2H), 3.54 (t, J=7.3 Hz, 2H), 2.73 (t, J=7.6 Hz, 2H), 1.24 (t, J=7.1 Hz, 3H).

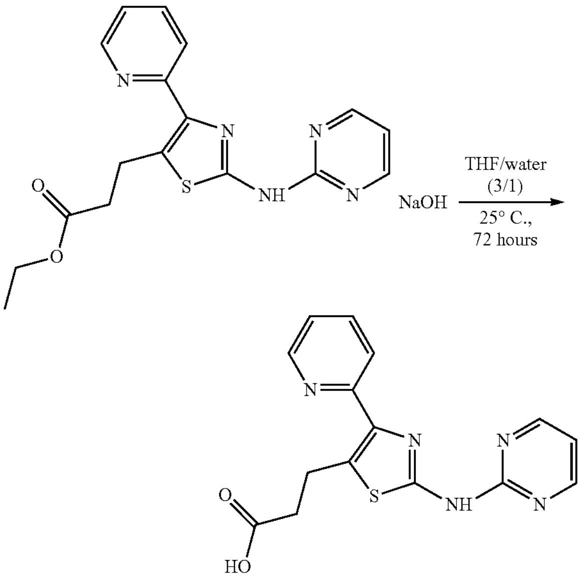

3-(4-(pyridin-2-yl)-2-(pyrimidin-2-ylamino)thiazol-5-yl)propanoic acid

To a solution of ethyl 3-(4-(pyridin-2-yl)-2-(pyrimidin-2-ylamino)thiazol-5-yl)propanoate (50 mg, 0.14 mmol) in tetrahydrofuran (3 ml) and water (1 ml) was added sodium hydroxide (1N, 1.4 ml). The mixture was stirred at 25° C. for 72 hours. The reaction was stripped of solvent under reduced pressure, diluted with water (10 ml) and acidified with 2N HCl (~pH2). The solution was filtered and the filtrate was washed with 0.5 ml methanol to afford a white solid (25 mg, 55%). Calculated for C15H13N5O2S, 327.08; MS (ESI) (m/z) observed 328.2 $(M+1)^+$. $^1H$ NMR (300 MHz, d6-DMSO, ppm): δ12.19 (s,b, 1H), 11.67 (s, 1H), 8.62 (t, J=7.7 Hz, 3H), 8.02 (d, J=7.9 Hz, 1H), 7.87 (t, J=7.6 Hz, 1H), 7.29 (t, J=7.6 Hz, 1H), 7.03 (t, J=4.3 Hz, 1H), 3.46 (t, 7.3 Hz, 2H), 2.65 (t, J=7.3 Hz, 3H).

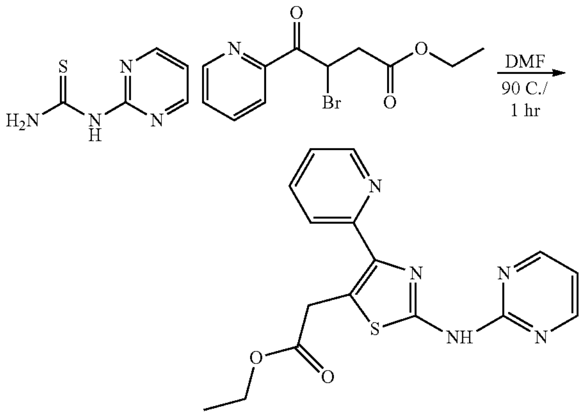

Ethyl 2-(4-(pyridin-2-yl)-2-(pyrimidin-2-ylamino) thiazol-5-yl)acetate

The title compound was prepared according to the procedure of Ethyl 2-((2-((4-methylpyrimidin-2-yl)amino)-4-(pyridin-2-yl)thiazol-5-yl)acetate. Calculated for C16H15N5O2S, 341.09; MS (ESI) (m/z) observed 342.2 $(M+1)^+$. $^1H$ NMR (300 MHz, d6-DMSO, ppm): δ 11.79 (s, 1H), 8.66 (d, J=5.0 Hz, 2H), 8.59 (d, J=5.0 Hz, 1H), 8.07 (d, J=8.2 Hz, 1H), 7.97 (t, J=7.6 Hz, 1H), 7.39 (t, J=6.2 Hz, 1H), 7.06 (t, J=5.0 Hz, 1H), 4.37 (s, 2H), 4.09 (q, J=7.0 Hz, 2H), 1.17 (t, J=7.1 Hz, 3H).

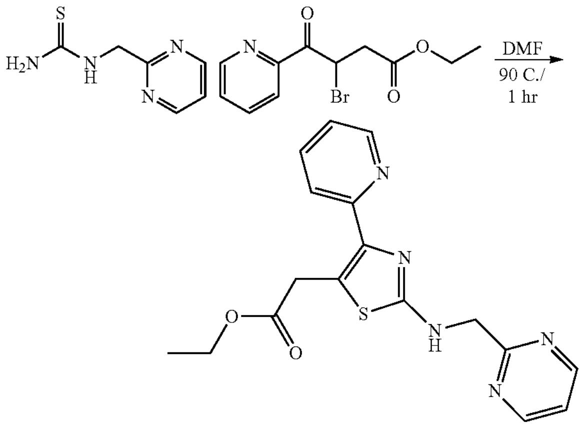

Ethyl 2-(4-(pyridin-2-yl)-2-((pyrimidin-2-ylmethyl) amino)thiazol-5-yl)acetate

The title compound was prepared according to the procedure of Ethyl 2-(2-((4-methylpyrimidin-2-yl)amino)-4-(pyridin-2-yl)thiazol-5-yl)acetate. Calculated for C17H17N5O2S, 355.11; MS (ESI) (m/z) observed 356.2 $(M+1)^+$. $^1H$ NMR (300 MHz, CDCl3, ppm): δ 8.75 (d, J=5.0 Hz, 2H), 8.54 (d, J=5.0 Hz, 1H), 8.01 (d, J=10.0 Hz, 1H), 7.70 (t, J=9.3 Hz, 1H), 7.24 (t, J=5.0 Hz, 1H), 7.12 (t, J=7.3 Hz, 1H), 6.39 (sb, 1H), 4.81 (d, J=3.5 Hz, 2H), 4.38 (s, 2H), 4.16 (q, J=7.3 Hz, 2H), 1.24 (t, J=7.3 Hz, 3H).

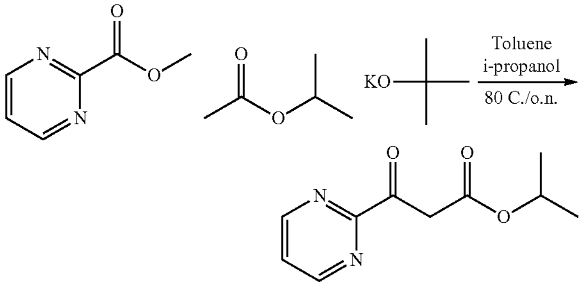

Isopropyl 3-oxo-3-(pyrimidin-2-yl)propanoate

To a solution of isopropyl acetate (4.7 ml, 40 mmol) in toluene (20 ml) and isopropanol (5 ml) was added potassium t-butoxide (2.24 g, 20 mmol). After stirring at room temperature for 30 minutes, methyl 2-pyrimidylcarboxylate (1.38 g, 10 mmol) was added to above solution. The mixture was heated at 80° C. over night. Cooled and quenched by adding water (50 ml). The solution was extracted with ethyl acetate (50 ml×2). The combined organic phase was washed with water (20 ml×3), aqueous $NaHCO_3$ and brine. The solution was dried over $Na_2SO_4$, filtered, and the solvents were removed to provide the crude product. The crude product was purified by ISCO chromatography (30-50% ethyl acetate in hexanes) to afford product as light yellow oil (1.13 g, 55%). Calculated for C10H12N2O3, 208.08; MS (ESI) (m/z) observed 209.2 $(M+1)^+$. $^1H$ NMR (300 MHz, CDCl3, ppm): δ 12.34 (d, J=7.3 Hz, 1/2H), 8.93 (dd, J=5.0 Hz, 22.6 Hz, 2H), 7.41 (dd, J=4.7 Hz, 36.0 Hz, 1H); 6.46 (d, J=7.4 Hz, 1/2H); 5.16 (db, J=34.6 Hz, 1H); 4.15 (m, 1H); 1.32 (d, J=6.2 Hz, 3H); 1.19 (d, J=6.2 Hz, 3H).

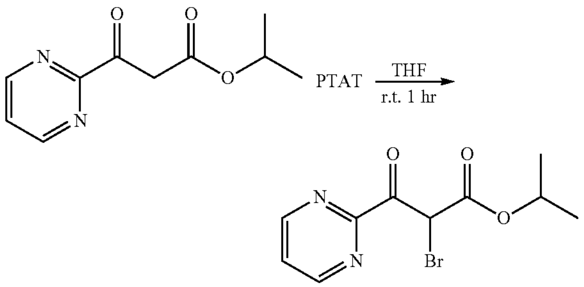

Isopropyl 2-bromo-3-oxo-3-(pyrimidin-2-yl)propanoate

The title compound was prepared according to the procedure of 2-bromo-3-ethoxy-1-(pyridin-2-yl)propan-1-one (yield 73%). Calculated for C10H11BrN2O3, 286/288; MS (ESI) (m/z) observed 287/289 $(M+1)^+$. $^1H$ NMR (300 MHz, CDCl3, ppm): δ 8.97 (d, J=5.0 Hz, 2H), 7.51 (t, J=6.5 Hz, 1H), 6.01 (s, 1H); 5.10 (septet, J=6.5 Hz, 1H); 1.18 (d, J=4.6 Hz, 3H); 1.16 (d, J=3.5 Hz, 3H).

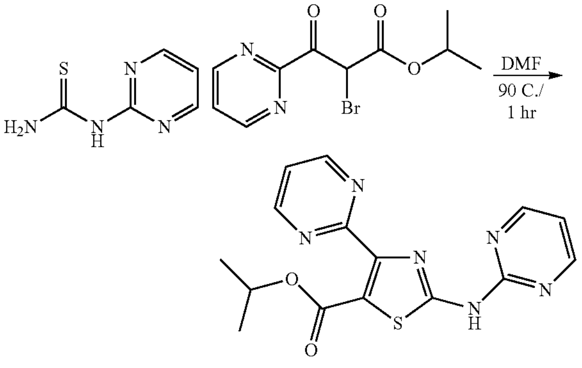

Isopropyl 4-(pyrimidin-2-yl)-2-(pyrimidin-2-ylamino)thiazole-5-carboxylate

The title compound was prepared according to the procedure of Ethyl 2-(2-((4-methylpyrimidin-2-yl)amino)-4-(pyridin-2-yl)thiazol-5-yl)acetate except that after cooling, the reaction was, filtered and the filtrate was washed with methanol to afford product as white solid (yield 42%). Calculated for C15H14N6O2S, 342.09; MS (ESI) (m/z) observed 343.2 $(M+1)^+$. $^1H$ NMR (300 MHz, D6-dmso, ppm): δ 12.41 (s, 1H), 8.89 (d, J=5.0 Hz, 2H), 8.74 (d, J=4.7 Hz, 2H), 7.56 (t, J=4.7 Hz, 1H), 7.15 (t, J=5.0 Hz, 1H), 4.88 (m, J=6.1 Hz, 1H); 1.05 (d, J=6.2 Hz, 6H).

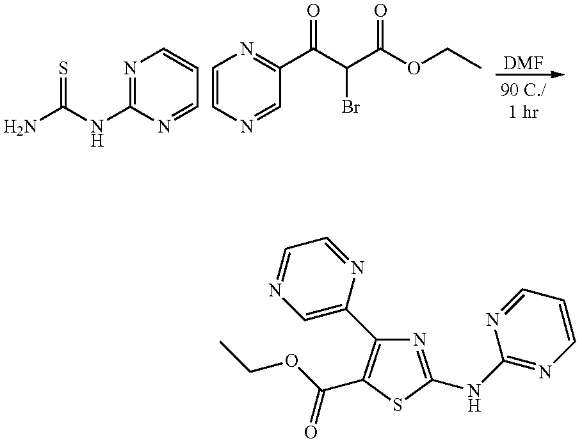

Ethyl 4-(pyrazin-2-yl)-2-(pyrimidin-2-ylamino)thiazole-5-carboxylate

The title compound was prepared according to the procedure of Ethyl 2-(2-((4-methylpyrimidin-2-yl)amino)-4-(pyridin-2-yl)thiazol-5-yl)acetate, except that after cooling, the reaction was, filtered and the filtrate was washed with methanol to afford the product as white solid (yield 77%). Calculated for C14H12N6O2S, 328.07; MS (ESI) (m/z) observed 329.2 $(M+1)^+$. $^1H$ NMR (300 MHz, D6-dmso, ppm): δ 12.50 (s, 1H), 8.93 (s, 1H), 8.73 (m, 4H), 7.18 (t, J=5.0 Hz, 1H), 4.18 (q, J=7.0 Hz, 2H); 1.15 (t, J=7.0 Hz, 3H).

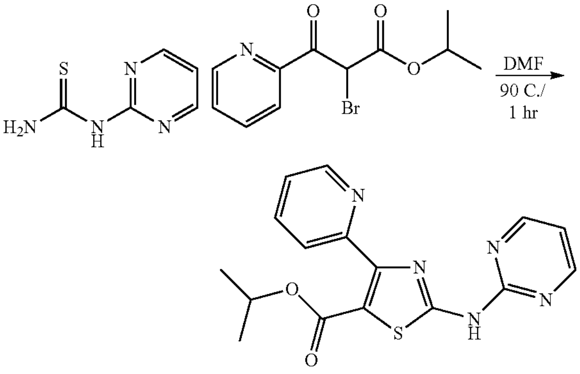

Isopropyl 4-(pyridin-2-yl)-2-(pyrimidin-2-ylamino)thiazole-5-carboxylate

The title compound was prepared according to the procedure of Ethyl 2-(2-((4-methylpyrimidin-2-yl)amino)-4-(pyridin-2-yl)thiazol-5-yl)acetate, except that after cooling, the reaction was, filtered and the filtrate was washed with methanol to afford the product as a white solid (yield 63%). Calculated for C16H15N5O2S, 341.09; MS (ESI) (m/z) observed 342.2 $(M+1)^+$. $^1H$ NMR (300 MHz, D6-dmso, ppm): δ 12.56 (s, 1H), 8.89 (d, J=4.7 Hz, 1H), 8.79 (d, J=4.7 Hz, 2H), 8.40 (t, J=7.9 Hz, 1H), 8.09 (d, J=7.9 Hz, 1H), 7.89 (t, J=5.9 Hz, 1H), 7.20 (t, J=4.7 Hz, 1H), 5.01 (m, J=6.1 Hz, 1H); 1.18 (d, J=6.4 Hz, 6H).

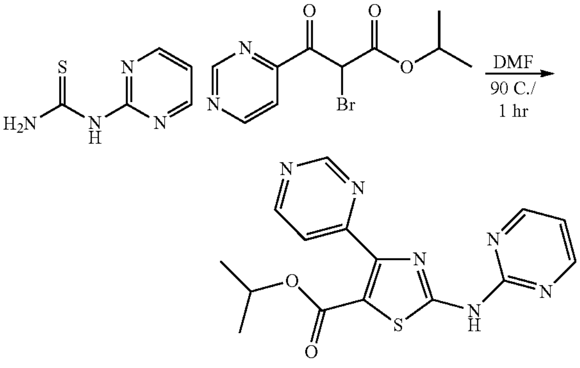

Isopropyl 2-(pyrimidin-2-ylamino)-4-(pyrimidin-4-yl)thiazole-5-carboxylate

The title compound was prepared according to the procedure of Ethyl 2-(2-((4-methylpyrimidin-2-yl)amino)-4-(pyridin-2-yl)thiazol-5-yl)acetate, except that after cooling, the reaction was, filtered and the filtrate was washed with methanol to afford the product as a light pink solid (yield 35%). Calculated for C15H14N6O2S, 342.09; MS (ESI) (m/z) observed 343.2 $(M+1)^+$. $^1H$ NMR (300 MHz, D6-dmso, ppm): δ 12.48 (s, 1H), 9.24 (s, 1H), 8.90 (d, J=5.3 Hz, 1H), 8.74 (d, J=5.0 Hz, 2H), 7.79 (d, J=5.3 Hz, 1H), 7.15 (t, J=4.1 Hz, 1H), 4.97 (m, J=6.1 Hz, 1H); 1.14 (d, J=6.4 Hz, 6H).

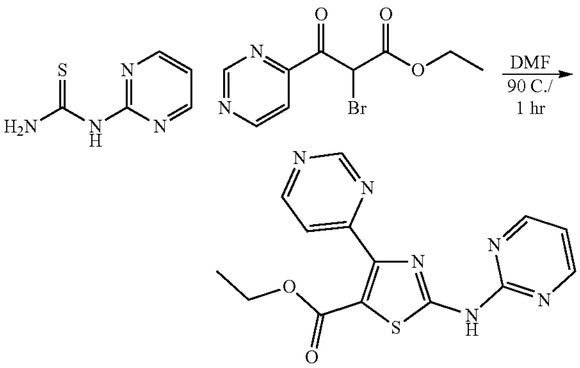

Ethyl 2-(pyrimidin-2-ylamino)-4-(pyrimidin-4-yl) thiazole-5-carboxylate

The title compound was prepared according to the procedure of Ethyl 2-(2-((4-methylpyrimidin-2-yl)amino)-4-(pyridin-2-yl)thiazol-5-yl)acetate, except that after cooling, the reaction was, filtered and the filtrate was washed with methanol to afford the product as a as white solid (yield 81%). Calculated for C14H12N6O2S, 328.07; MS (ESI) (m/z) observed 329.2 $(M+1)^+$. $^1H$ NMR (300 MHz, D6-dmso, ppm): δ 12.48 (s, 1H), 9.24 (s, 1H), 8.92 (d, J=5.3 Hz, 1H), 8.74 (d, J=5.3 Hz, 2H), 7.80 (d, J=6.7 Hz, 1H), 7.16 (t, J=4.4 Hz, 1H), 4.16 (q, J=7.0 Hz, 2H); 1.15 (t, J=7.1 Hz, 3H).

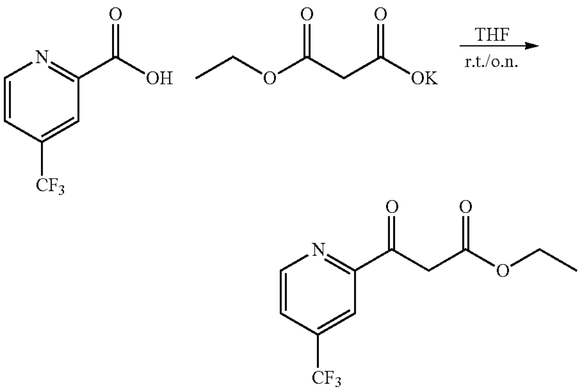

Ethyl 3-oxo-3-(4-(trifluoromethyl)pyridin-2-yl)propanoate

In a 100 ml round-bottomed flask under nitrogen was mixed 4-trifluoromethylpyridinyl-2-carboxylic acid (500 mg, 2.62 mmol), carbonyl diimidazole (510 mg, 3.14 mmol), and tetrahydrofuran (50 ml). The mixture was stirred at 25° C. for 1.5 hours before magnesium chloride (250 mg, 2.62 mmol) and ethyl potassium malonate (446 mg, 2.62 mmol) were added (cloudy after 2 hrs). After stirring at 25° C. overnight, the reaction mixture (some white solid out of the solution) was carefully neutralized with 2 N HCl, The aqueous phase was extracted with ethyl acetate (3×). The organic layer was dried over $Na_2SO_4$, filtered and concentrated under reduced pressure. The crude mixture was purified by ISCO to afford 600 mg colorless oil (88%). Calculated for C11H10F3NO3, 261.06; MS (ESI) (m/z) observed 262.2 $(M+1)^+$.

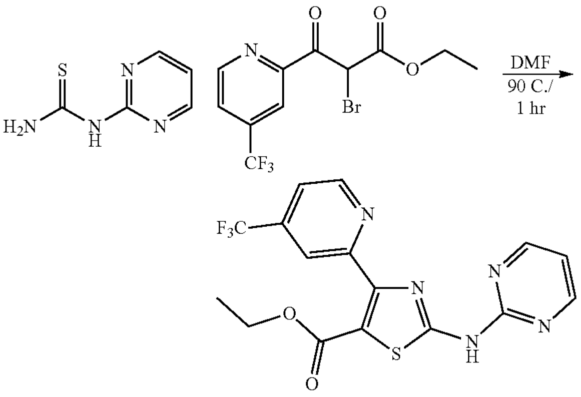

Ethyl 2-(pyrimidin-2-ylamino)-4-(4-(trifluoromethyl)pyridin-2-yl)thiazole-5-carboxylate The title compound was prepared according to the procedure of Ethyl 2-(2-((4-methylpyrimidin-2-yl)amino)-4-(pyridin-2-yl)thiazol-5-yl)acetate, except that after cooling, the reaction was, filtered and the filtrate was washed with methanol to afford the product as white needle crystal (yield 34%). Calculated for C16H12F3N5O2S, 395.07; MS (ESI) (m/z) observed 396.2 $(M+1)^+$. $^1H$ NMR (300 MHz, D6-dmso, ppm): δ 12.43 (s, 1H), 8.91 (d, 1H, J=4.98 Hz), 8.74 (d, 2H, J=4.69 Hz), 8.06 (s, 1H), 7.82 (d, 1H, J=8 Hz), 7.15 (t, 1H, J=3.81 Hz), 4.15 (q, 2H, J=6.74 Hz), 1.12 (t, 3H, J=6.75 Hz).

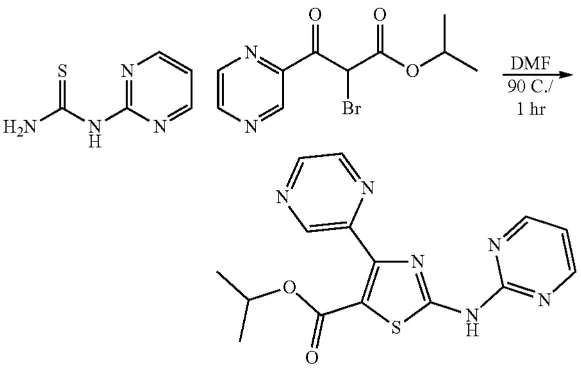

Isopropyl 4-(pyrazin-2-yl)-2-(pyrimidin-2-ylamino) thiazole-5-carboxylate

The title compound was prepared according to the procedure of Ethyl 2-(2-((4-methylpyrimidin-2-yl)amino)-4-(pyridin-2-yl)thiazol-5-yl)acetate, except that after cooling, the reaction was, filtered and the filtrate was washed with methanol to afford the product as a white solid. The white solid was purified by ISCO and eluted with 50-100% ethyl acetate in hexanes (total yield 91%). Calculated for C15H14N6O2S, 342.09; MS (ESI) (m/z) observed 343.2 $(M+1)^+$. $^1H$ NMR (300 MHz, D6-dmso, ppm): δ 12.46 (s, 1H), 8.90 (d, 1H, J=1.46 Hz), 8.74 (m, 4H), 7.16 (t, 1H, J=5.00 Hz), 4.96 (m, 1H, J=6.16 Hz), 1.13 (d, 6H, J=6.16 Hz).

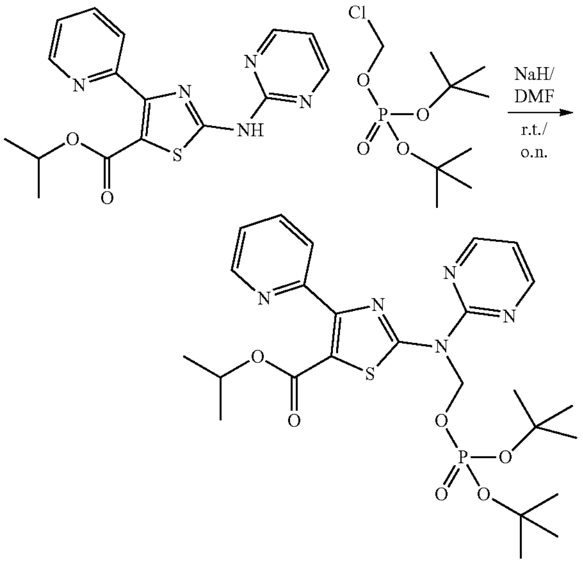

Isopropyl 2-((((di-tert-butoxyphosphoryl)oxy) methyl)(pyrimidin-2-yl)amino)-4-(pyridin-2-yl)thiazole-5-carboxylate The title compound was prepared according to the procedure of di-tert-butyl(((4-(pyridin-2-yl)thiazol-2-yl)(pyrimidin-2-yl)amino)methyl) phosphate. (yield 12%). Calculated for C25H34N5O6PS, 363.20; MS (ESI) (m/z) observed 564.4 $(M+1)^+$. $^{1}$H NMR (300 MHz, CDCl3, ppm): δ 8.70 (m, 3H), 7.76 (m, 2H), 7.31 (m, 1H), 7.07 (t, 1H, J=4.70 Hz), 6.61 (d, 2H, J=4.98 Hz), 5.14 (m, J=6.4 Hz, 1H), 1.39 (s, 18H), 1.27 (d, J=6.2 Hz, 6H).

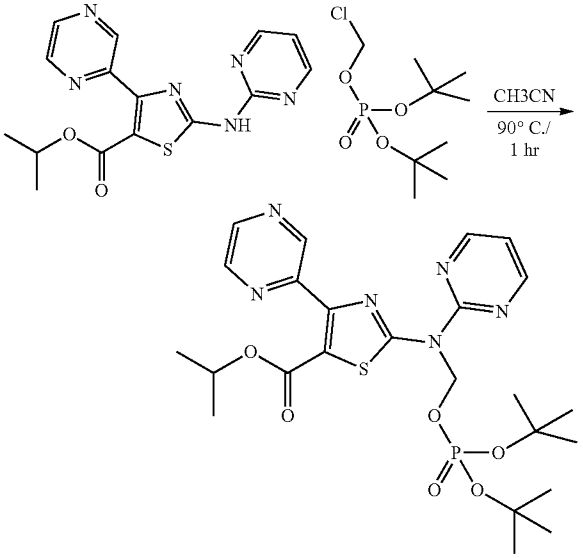

Isopropyl 2-((((di-tert-butoxyphosphoryl)oxy) methyl)(pyrimidin-2-yl)amino)-4-(pyrazin-2-yl)thiazole-5-carboxylate (Method 2) To a solution of isopropyl 4-(pyrazin-2-yl)-2-(pyrimidin-2-ylamino)thiazole-5-carboxylate (20 mg, 0.058 mmol) in 4 ml acetonitrile was added potassium carbonate (33 mg, 0.24 mmol) and di-tert-butyl (chloromethyl) phosphate (31 mg, 0.12 mmol). The mixture was heated under argon at 90° C. for 1 hour. The reaction is cooled to room temperature and diluted with 50 ml ethyl acetate and washed with water (50 ml×4), brine. The crude material was purified by ISCO (50-100% ethyl acetate in hexanes) to afford 15 mg white grease (46%). Calculated for C24H33N6O6PS, 564.19; MS (ESI) (m/z) observed 565.4 $(M+1)^+$. $^{1}$H NMR (300 MHz, CDCl3, ppm): δ 9.00 (s, 1H), 8.73 (d, 2H, J=2.9 Hz), 8.65 (s, 1H), 8.59 (s, 1H), 7.09 (t, 1H, J=5.00 Hz), 6.61 (d, 2H, J=5.28 Hz), 5.16 (m, J=6.4 Hz, 1H), 1.39 (s, 18H), 1.27 (d, J=6.2 Hz, 6H).

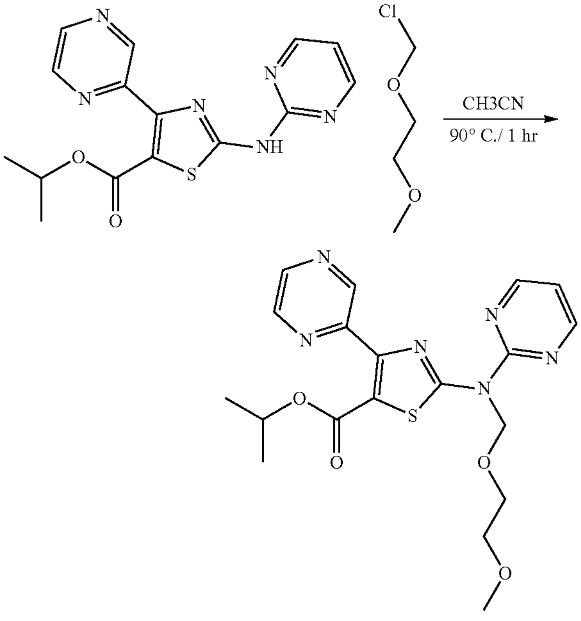

Isopropyl 2-(((2-methoxyethoxy)methyl)(pyrimidin-2-yl)amino)-4-(pyrazin-2-yl)thiazole-5-carboxylate The title compound was prepared according to the procedure of Isopropyl 2-((((di-tert-butoxyphosphoryl)oxy) methyl)(pyrimidin-2-yl)amino)-4-(pyrazin-2-yl)thiazole-5-carboxylate. (yield 50%). Calculated for C19H22N6O4S, 430.14; MS (ESI) (m/z) observed 431.3 $(M+1)^+$. $^{1}$H NMR (300 MHz, CDCl3, ppm): δ 9.00 (s, 1H), 8.74 (d, 2H, J=2.64 Hz), 8.67 (s, 1H), 8.59 (s, 1H), 7.06 (t, 1H, J=5.28 Hz), 6.26 (s, 2H), 5.16 (m, 1H), 3.90 (t, 2H, J=4.98 Hz), 3.53 (t, 2H, J=4.69), 3.31 (s, 3H), 1.26 (d, 6H, J=5.86 Hz).

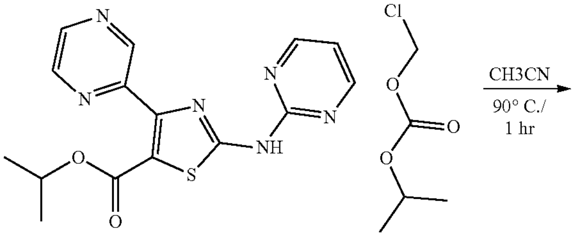

-continued

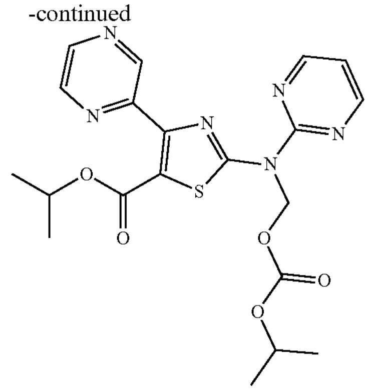

Isopropyl 2-((((isopropoxycarbonyl)oxy)methyl)(pyrimidin-2-yl)amino)-4-(pyrazin-2-yl)thiazole-5-carboxylate The title compound was prepared according to the procedure of Isopropyl 2-((((di-tert-butoxyphosphoryl)oxy)methyl)(pyrimidin-2-yl)amino)-4-(pyrazin-2-yl)thiazole-5-carboxylate. (yield 68%). Calculated for C20H22N6O5S, 458.14; MS (ESI) (m/z) observed 459.3 $(M+1)^+$. $^1$H NMR (300 MHz, CDC13, ppm): δ 9.00 (s, 1H), 8.72 (d, 2H, J=2.9 Hz), 8.65 (s, 1H), 8.58 (s, 1H), 7.09 (t, 1H, J=5.00 Hz), 6.79 (s, 2H), 5.16 (m, 1H), 4.91 (m, 1H), 1.27 (d, 6H, J=4.1 Hz), 1.24 (d, 6H, J=4.11 Hz).

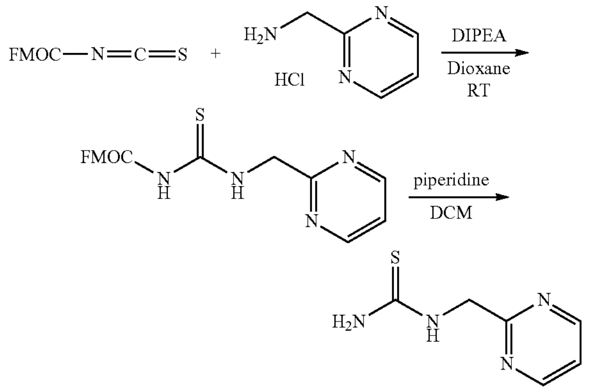

A mixture of methyl amino pyrimidine (250 mg, 1 eq, 1.718 mmol), FMOC-NCS (531 mg, 1.1 eq, 1.9 mmol) and diisopropyl ethyl amine (0.3 ml, 1 eq, 1.718 mmol) was stirred in 1,4-dioxane (10 ml) at 25° C. overnight under argon atmosphere. A solid separated out from mixture was filtered and washed with water and ethyl acetate, and dried under high vacuum. Yield 658 mg, 98%. Solid obtained from the reaction (658 mg, 1 eq, 1.2 mmol) was stirred in piperidine (3 ml) and dichloromethane (15 ml) at 25° C. overnight. A solid precipitate was collected by filtration and washed with dichloromethane and water to give a white solid. Yield 289 mg, 98%. LCMS, 169 (MH+).

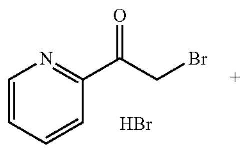

-continued

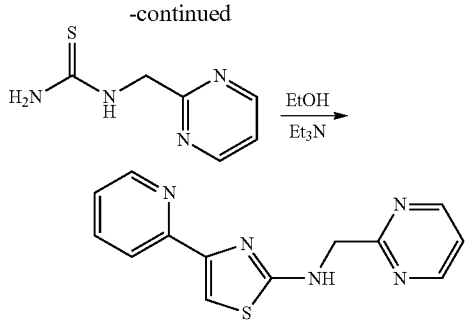

The reaction was performed using (100.32 mg, 1 eq, 0.357 mmol) of 2-bromo-1-(pyridin-2-yl)ethanone hydrobromide, (60 mg, 1 eq, 0.357 mmol) of 1-((pyrimidin-2-yl)methyl)thiourea, (0.173 ml, 3.5 eq, 1.25 mmol) of triethylamine, and 5 ml of ethanol. The mixture was heated at 87° C. for 2 hours. The reaction was quenched with cold water and filtered. Crude compound was purified by Column Chromatography using 5% methanol/ethyl acetate. Yield 0.040 g, 42%. $^1$HNMR (300 mHz, $CDCl_3$) d 8.77 (s, 1H), 8.75 (s, 1H), 8.59 (d, J=3.9 Hz, 1H), 8.01 (d, J=8.4 Hz, 1H), 7.75 (q, J=8.7 Hz, 1H), 7.34 (s, 1H), 7.19 (t, J=5.7 Hz, 1H), 6.49 (s, 1H), 4.85 (s, 2H); LCMS, 270 (MH+).

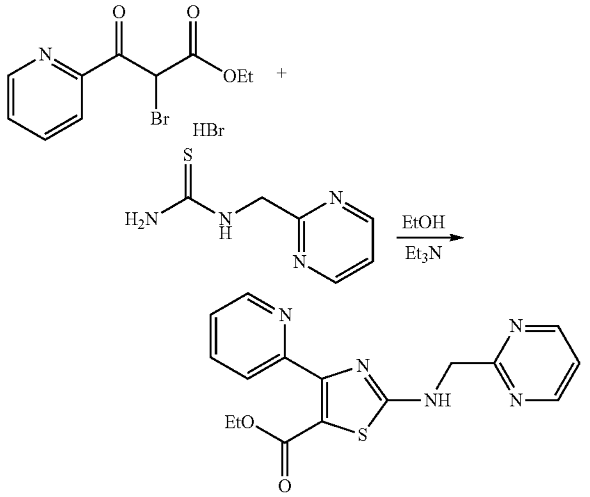

The reaction was performed using (316 mg, 1.5 eq, 0.9 mmol) of ethyl 2-bromo-3-oxo-3-(pyridin-2-yl)propanoate hydrobromide, (100 mg, 1 eq, 0.6 mmol) of 1-((pyrimidin-2-yl)methyl)thiourea, (0.3 ml, 3.5 eq, 2.1 mmol) of triethylamine, and 5 ml of ethanol. The mixture was heated at 87° C. for 2 hours. The reaction was quenched with cold water and filtered Yield 0.025 g, 12.32%. IHNMR (300 mHz, $CDCl_3$) d 8.81 (s, 1H), 8.80-8.74 (m, 2H), 7.90-7.75 (m, 2H), 7.40-7.30 (m, 1H), 7.28 (m, 1H), 4.75 (s, 2H), 4.21 (q, J=6.9 Hz, 2H), 1.29 (bs, 3H); LCMS, 342 (MH+).

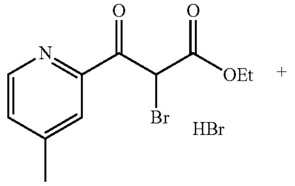

-continued

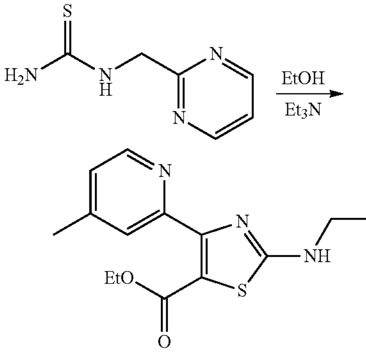

The reaction was performed using (131 mg, 1 eq, 0.357 mmol) of ethyl 2-bromo-3-(4-methylpyridin-2-yl)-3-oxo-propanoate hydrobromide, (40 mg, 1 eq, 0.238 mmol) of 1-((pyrimidin-2-yl)methyl)thiourea, (0.115 ml, 3.5 eq, 0.833 mmol) of triethylamine, and 5 ml of ethanol. The mixture was heated at 87° C. for 2 hours. The reaction was quenched with cold water and filtered Yield 0.020 g, 24%. $^1$HNMR (300 mHz, $CDCl_3$) d 8.76 (s, 1H), 8.74 (s, 1H), 8.45 (m, 1H), 7.58 (d, J=8.4 Hz, 1H), 7.22 (m, 1H), 6.98 (m, 1H), 4.77 (d, J=4.5 Hz, 2H), 4.11 (q, J=7.2 Hz, 2H), 2.26 (s, 3H), 1.12 (t, J=7.2 Hz, 3H); LCMS, 356 (MH+).

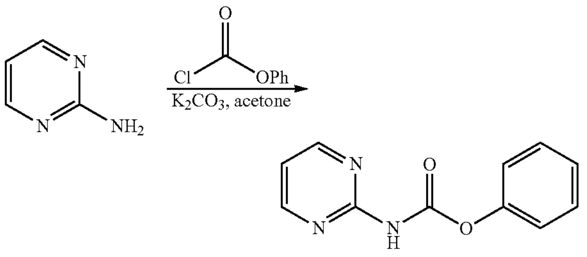

Phenyl Pyrimidin-2-ylcarbamate

To a suspension of pyrimidin-2-amine (243 mg, 2.56 mmol) and potassium carbonate (407 mg, 2.94 mmol) in acetone was added phenyl carbonochloridate (0.35 ml, 2.81 mmol). The mixture was stirred at 25° C. for 4 hours, and then filtered. The filtrate was concentrated and redissolved in methylene chloride, washed with $Na_2CO_3$ (10% in water), HCl (1 N), and brine. The organic solution was concentrated to give a light yellow solid, which was used in the next step without further purification. Calculated for C11H9N3O2, 215.07; MS (ESI) (m/z) observed 216.2 (M+1)$^+$.

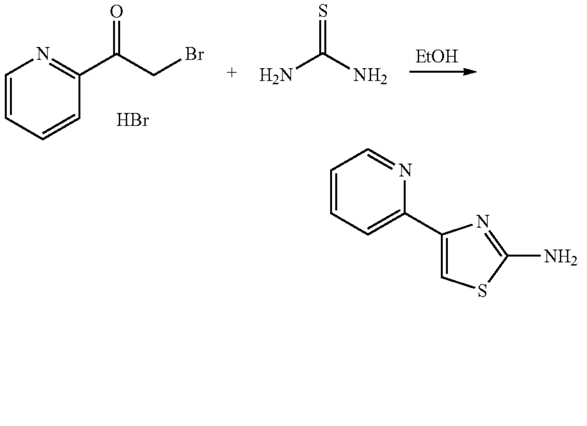

4-(pyridin-2-yl)thiazol-2-amine 2-bromo-1-(pyridin-2-yl)ethanone hydrobromide (500 mg, 1.78 mmol) and thiourea (542 mg, 7.12 mmole, 4 eq) were stirred in ethanol at 90° C. for 3 hours and then cooled and concentrated. The residue was partitioned between ethyl acetate and saturated $NaHCO_3$. The organic phase was washed with water and brine, and then concentrated. The light yellow solid obtained was triturated with methylene chloride and dried (280 mg, 89%). $^1$H NMR (300 MHz, $CDCl_3$): δ 8.59 (d, J=4.4 Hz, 1H), 7.89 (d, J=7.9 Hz, 1H), 7.72 (td, J=7.9, 1.8 Hz, 1H), 7.31 (s, 1H), 7.22-6.94 (m, 1H); Calculated for C8H7N3S, 177.04; MS (ESI) (m/z) observed 178.1 (M+1)$^+$.

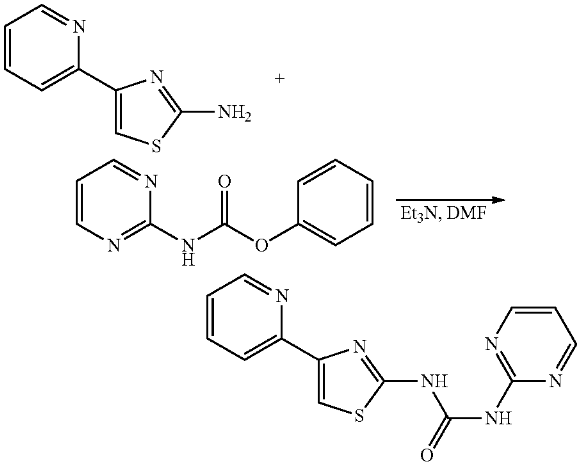

1-(4-(pyridin-2-yl)thiazol-2-yl)-3-(pyrimidin-2-yl) urea

Phenyl pyrimidin-2-ylcarbamate (60 mg, 0.28 mmol), $Et_3N$ (0.08 ml, 0.56 mmol), and 4-(pyridin-2-yl)thiazol-2-amine (50 mg, 0.28 mmol) were dissolved in N,N-dimethyl formamide. The mixture was stirred at 25° C. for 72 hours. The turbid mixture was filtered. The solid was washed with ethyl acetate, ether, and dried (35 mg, 42%). $^1$H NMR (300 MHz, DMSO): δ 12.65 (s, 1H), 10.84 (s, 1H), 8.90-8.40 (m, 4H), 8.10-7.70 (m, 2H), 7.40-7.10 (m, 2H); Calculated for C13H10N6OS, 298.06; MS (ESI) (m/z) observed 299.2 (M+1)$^+$.

Formulations

The present invention also relates to compositions or formulations which comprise the substituted aminothiazoles according to the present invention. In general, the compositions of the present invention comprise an effective amount of one or more substituted aminothiazoles and salts thereof according to the present invention which are effective for providing treatment or preventing diseases that involve unregulated cell growth; and one or more excipients. The compositions of the present invention also comprise an effective amount of one or more substituted aminothiazoles and salts thereof according to the present invention which are effective for treating or preventing diseases that involve infection with a hepatitis virus; and one or more excipients.

For the purposes of the present invention the term “excipient” and “carrier” are used interchangeably throughout the description of the present invention and said terms are defined herein as, "ingredients which are used in the practice of formulating a safe and effective pharmaceutical composition."

The formulator will understand that excipients are used primarily to serve in delivering a safe, stable, and functional pharmaceutical, serving not only as part of the overall vehicle for delivery but also as a means for achieving effective absorption by the recipient of the active ingredient. An excipient may fill a role as simple and direct as being an inert filler, or an excipient as used herein may be part of a pH stabilizing system or coating to insure delivery of the ingredients safely to the stomach. The formulator can also take advantage of the fact the compounds of the present invention have improved cellular potency, pharmacokinetic properties, as well as improved oral bioavailability.

The present teachings also provide pharmaceutical compositions that include at least one compound described herein and one or more pharmaceutically acceptable carriers, excipients, or diluents. Examples of such carriers are well known to those skilled in the art and can be prepared in accordance with acceptable pharmaceutical procedures, such as, for example, those described in *Remington's Pharmaceutical Sciences,* 17th edition, ed. Alfonoso R. Gennaro, Mack Publishing Company, Easton, Pa. (1985), the entire disclosure of which is incorporated by reference herein for all purposes. As used herein, "pharmaceutically acceptable" refers to a substance that is acceptable for use in pharmaceutical applications from a toxicological perspective and does not adversely interact with the active ingredient. Accordingly, pharmaceutically acceptable carriers are those that are compatible with the other ingredients in the formulation and are biologically acceptable. Supplementary active ingredients can also be incorporated into the pharmaceutical compositions.

Compounds of the present teachings can be administered orally or parenterally, neat or in combination with conventional pharmaceutical carriers. Applicable solid carriers can include one or more substances which can also act as flavoring agents, lubricants, solubilizers, suspending agents, fillers, glidants, compression aids, binders or tablet-disintegrating agents, or encapsulating materials. The compounds can be formulated in conventional manner, for example, in a manner similar to that used for known anti-cancer agents. The compounds can also be formulated in conventional manner, for example, in a manner similar to that used for known anti-viral agents. Oral formulations containing a compound disclosed herein can comprise any conventionally used oral form, including tablets, capsules, buccal forms, troches, lozenges and oral liquids, suspensions or solutions. In powders, the carrier can be a finely divided solid, which is an admixture with a finely divided compound. In tablets, a compound disclosed herein can be mixed with a carrier having the necessary compression properties in suitable proportions and compacted in the shape and size desired. The powders and tablets can contain up to 99% of the compound.

Capsules can contain mixtures of one or more compound(s) disclosed herein with inert filler(s) and/or diluent(s) such as pharmaceutically acceptable starches (e.g., corn, potato or tapioca starch), sugars, artificial sweetening agents, powdered celluloses (e.g., crystalline and microcrystalline celluloses), flours, gelatins, gums, and the like.

Useful tablet formulations can be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, sodium lauryl sulfate, talc, sugars, lactose, dextrin, starch, gelatin, cellulose, methyl cellulose, microcrystalline cellulose, sodium carboxymethyl cellulose, carboxymethylcellulose calcium, polyvinylpyrrolidine, alginic acid, acacia gum, xanthan gum, sodium citrate, complex silicates, calcium carbonate, glycine, sucrose, sorbitol, dicalcium phosphate, calcium sulfate, lactose, kaolin, mannitol, sodium chloride, low melting waxes, and ion exchange resins. Surface modifying agents include nonionic and anionic surface modifying agents. Representative examples of surface modifying agents include, but are not limited to, poloxamer 188, benzalkonium chloride, calcium stearate, cetostearl alcohol, cetomacrogol emulsifying wax, sorbitan esters, colloidal silicon dioxide, phosphates, sodium dodecylsulfate, magnesium aluminum silicate, and triethanolamine. Oral formulations herein can utilize standard delay or time-release formulations to alter the absorption of the compound(s). The oral formulation can also consist of administering a compound disclosed herein in water or fruit juice, containing appropriate solubilizers or emulsifiers as needed.

Liquid carriers can be used in preparing solutions, suspensions, emulsions, syrups, elixirs, and for inhaled delivery. A compound of the present teachings can be dissolved or suspended in a pharmaceutically acceptable liquid carrier such as water, an organic solvent, or a mixture of both, or a pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers, and osmo-regulators. Examples of liquid carriers for oral and parenteral administration include, but are not limited to, water (particularly containing additives as described herein, e.g., cellulose derivatives such as a sodium carboxymethyl cellulose solution), alcohols (including monohydric alcohols and polyhydric alcohols, e.g., glycols) and their derivatives, and oils (e.g., fractionated coconut oil and arachis oil). For parenteral administration, the carrier can be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellants.

Liquid pharmaceutical compositions, which are sterile solutions or suspensions, can be utilized by, for example, intramuscular, intraperitoneal or subcutaneous injection. Sterile solutions can also be administered intravenously. Compositions for oral administration can be in either liquid or solid form.

Preferably the pharmaceutical composition is in unit dosage form, for example, as tablets, capsules, powders, solutions, suspensions, emulsions, granules, or suppositories. In such form, the pharmaceutical composition can be sub-divided in unit dose(s) containing appropriate quantities of the compound. The unit dosage forms can be packaged compositions, for example, packeted powders, vials, ampoules, prefilled syringes or sachets containing liquids. Alternatively, the unit dosage form can be a capsule or tablet itself, or it can be the appropriate number of any such compositions in package form. Such unit dosage form can contain from about 1 mg/kg of compound to about 500 mg/kg of compound, and can be given in a single dose or in two or more doses. Such doses can be administered in any manner useful in directing the compound(s) to the recipient's bloodstream, including orally, via implants, parenterally (including intravenous, intraperitoneal and subcutaneous injections), rectally, vaginally, and transdermally.

When administered for the treatment or inhibition of a particular disease state or disorder, it is understood that an effective dosage can vary depending upon the particular compound utilized, the mode of administration, and severity of the condition being treated, as well as the various physical factors related to the individual being treated. In therapeutic applications, a compound of the present teachings can be provided to a patient already suffering from a disease in an amount sufficient to cure or at least partially ameliorate the symptoms of the disease and its complications. The dosage to be used in the treatment of a specific individual typically must be subjectively determined by the attending physician. The variables involved include the specific condition and its state as well as the size, age and response pattern of the patient.

In some cases it may be desirable to administer a compound directly to the airways of the patient, using devices such as, but not limited to, metered dose inhalers, breath-operated inhalers, multidose dry-powder inhalers, pumps, squeeze-actuated nebulized spray dispensers, aerosol dispensers, and aerosol nebulizers. For administration by intranasal or intrabronchial inhalation, the compounds of the present teachings can be formulated into a liquid composition, a solid composition, or an aerosol composition. The liquid composition can include, by way of illustration, one or more compounds of the present teachings dissolved, partially dissolved, or suspended in one or more pharmaceutically acceptable solvents and can be administered by, for example, a pump or a squeeze-actuated nebulized spray dispenser. The solvents can be, for example, isotonic saline or bacteriostatic water. The solid composition can be, by way of illustration, a powder preparation including one or more compounds of the present teachings intermixed with lactose or other inert powders that are acceptable for intrabronchial use, and can be administered by, for example, an aerosol dispenser or a device that breaks or punctures a capsule encasing the solid composition and delivers the solid composition for inhalation. The aerosol composition can include, by way of illustration, one or more compounds of the present teachings, propellants, surfactants, and co-solvents, and can be administered by, for example, a metered device. The propellants can be a chlorofluorocarbon (CFC), a hydrofluoroalkane (HFA), or other propellants that are physiologically and environmentally acceptable.

Compounds described herein can be administered parenterally or intraperitoneally. Solutions or suspensions of these compounds or a pharmaceutically acceptable salts, hydrates, or esters thereof can be prepared in water suitably mixed with a surfactant such as hydroxyl-propylcellulose. Dispersions can also be prepared in glycerol, liquid polyethylene glycols, and mixtures thereof in oils. Under ordinary conditions of storage and use, these preparations typically contain a preservative to inhibit the growth of microorganisms.

The pharmaceutical forms suitable for injection can include sterile aqueous solutions or dispersions and sterile powders for the extemporaneous preparation of sterile injectable solutions or dispersions. In some embodiments, the form can sterile and its viscosity permits it to flow through a syringe. The form preferably is stable under the conditions of manufacture and storage and can be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Compounds described herein can be administered transdermally, i.e., administered across the surface of the body and the inner linings of bodily passages including epithelial and mucosal tissues. Such administration can be carried out using the compounds of the present teachings including pharmaceutically acceptable salts, hydrates, or esters thereof, in lotions, creams, foams, patches, suspensions, solutions, and suppositories (rectal and vaginal).

Transdermal administration can be accomplished through the use of a transdermal patch containing a compound, such as a compound disclosed herein, and a carrier that can be inert to the compound, can be non-toxic to the skin, and can allow delivery of the compound for systemic absorption into the blood stream via the skin. The carrier can take any number of forms such as creams and ointments, pastes, gels, and occlusive devices. The creams and ointments can be viscous liquid or semisolid emulsions of either the oil-in-water or water-in-oil type. Pastes comprised of absorptive powders dispersed in petroleum or hydrophilic petroleum containing the compound can also be suitable. A variety of occlusive devices can be used to release the compound into the blood stream, such as a semi-permeable membrane covering a reservoir containing the compound with or without a carrier, or a matrix containing the compound. Other occlusive devices are known in the literature.

Compounds described herein can be administered rectally or vaginally in the form of a conventional suppository. Suppository formulations can be made from traditional materials, including cocoa butter, with or without the addition of waxes to alter the suppository's melting point, and glycerin. Water-soluble suppository bases, such as polyethylene glycols of various molecular weights, can also be used.

Lipid formulations or nanocapsules can be used to introduce compounds of the present teachings into host cells either in vitro or in vivo. Lipid formulations and nanocapsules can be prepared by methods known in the art.

To increase the effectiveness of compounds of the present teachings, it can be desirable to combine a compound with other agents effective in the treatment of the target disease. For example, other active compounds (i.e., other active ingredients or agents) effective in treating the target disease can be administered with compounds of the present teachings. The other agents can be administered at the same time or at different times than the compounds disclosed herein.

Compounds of the present teachings can be useful for the treatment or inhibition of a pathological condition or disorder in a mammal, for example, a human subject. The present teachings accordingly provide methods of treating or inhibiting a pathological condition or disorder by providing to a mammal a compound of the present teachings including its pharmaceutically acceptable salt) or a pharmaceutical composition that includes one or more compounds of the present teachings in combination or association with pharmaceutically acceptable carriers. Compounds of the present teachings can be administered alone or in combination with other therapeutically effective compounds or therapies for the treatment or inhibition of the pathological condition or disorder.

Non-limiting examples of compositions according to the present invention include from about 0.001 mg to about 1000 mg of one or more according to the present invention and one or more excipients; from about 0.01 mg to about 100 mg of one or more substituted aminothiazoles according to the present invention and one or more excipients; and from about 0.1 mg to about 10 mg of one or more substituted aminothiazoles according to the present invention; and one or more excipients.

Procedures

The following procedures can be utilized in evaluating and selecting compounds as effective for providing treatment or preventing diseases that involve unregulated cell growth. The following procedures can also be utilized in evaluating and selecting compounds as effective for treating or preventing diseases that involve infection with a hepatitis virus.

Cell Cultures and Conditions

Huh-7 cells and derived from hepatocellular carcinoma cells, and were donated by Dr. Xuanyong Lu, (Drexel University College of Medicine, Doylestown, Pa.). THLE-2 were purchased from American Type Culture Collection (Manassas, Va.). PH5CH were donated by Dr. Masayuki Noguchi (University of Tsukuba, Ibaraki, Japan). THLE-2 and PH5CH have been immortalized through stable transfection of the SV40 large T antigen in normal hepatocytes, and are thus cell lines that are representative of normal hepatocytes rather than HCC cells. THLE2 have been confirmed to not form tumors in athymic mice. All cell lines were cultured and maintained in 5% $CO_2$ at 37° C. Huh-7 were maintained in the culture media DMEM/F12 (Dulbecco's Modified Eagle Medium) with 10% Fetal bovine serum (FBS), 100 □g/mL penicillin, 100 units/mL streptomycin, and 50 □g/mL normocin. THLE-2 and PH5CH were maintained in the culture media Brochial Epithelial Growth Media (BEGM) with 10% FBS, 100 □□g/mL penicillin, 100 units/mL streptomycin, with the following additives form the prepackaged kit: Bovine pituitary extract (BPE), insulin, hydrocortisone, retinoic acid, transferrin, triiodothyronine, supplemented with 5 ng/ml human epidermal growth factor and 70 ng/ml phosphoethanolamine (Lonza Walkersville Inc., Walkersville, Md.).

Testing of Substituted Aminothiazole Analogues

Huh7 cells were plated on 96-well plates at $2.0\times10^4$ cells per well to permit grow in the presence of compounds of the disclosure. Compounds of the disclosure were prediluted and transferred to cell plates by automated liquid handling. Cells were incubated with compounds of the disclosure for 72 hours, after which culture growth and viability were assessed by addition of 50 □g/mL 3-(4,5-Dimethyl-2-thiazolyl)-2,5-diphenyl-2H-tetrazolium bromide (MTT) incubation for 4 hours at 37° C. Solubilization buffer (0.01M HCl, 10% SDS) was added followed by incubation at 37° C. overnight. Absorbance was measured at 570 nm (reference 630 nm). Compound of the disclosure were tested in in Huh7, THLE-2 and PH5CH, over eight-point dilutions in half-log steps, testing 50.0, 16.6, 5.0, 1.66, 0.5, 0.166, 0.05, and 0.016 □M in 0.5% DMSO, with each concentration in duplicate wells. The mean value of the reduction of viability signal in the MTT assay over the duplicate wells was used to determine the concentration that is cytoxic to 50% of the cells ($CC_{50}$), as compared to DMSO-only control wells (n=8), using curve-fitting analysis with XLfit (IDBS, Surrey, UK). Each compound was tested from 2 to 7 times in separate assay trials.

Selectivity of toxicity in HCC-derived cells over normal liver-derived cells is important for the purposes of developing a therapy that specifically targets the cancer with low toxcity for the whole tumor. The Selective Index (SI) is the ratio of $CC_{50}$ in normal cells (THLE2 or PHSCH) over the $CC_{50}$ in the liver cancer derived cells; thus, the higher the number, the lower the potential toxicity at an efficacious dose.

TABLE 6

Exemplary cell viability screening results for compounds of the disclosure with Huh-7 cells, THLE2 cells and PH5CH cells.

| Entry | Structure | Cytotoxicity $CC_{50}$ (□M) | Selectivity |
|---|---|---|---|
| 1 | 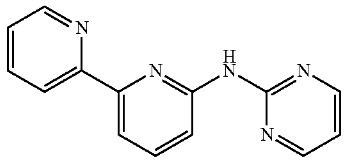 [SMILES: c1ccc(-c2cccc(Nc3ncccn3)n2)nc1] | <50.0 | >5.0 |
| 2 | 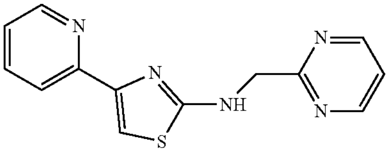 [SMILES: c1ccc(-c2csc(NCc3ncccn3)n2)nc1] | <50.0 | ≤5.0 |
| 3 | 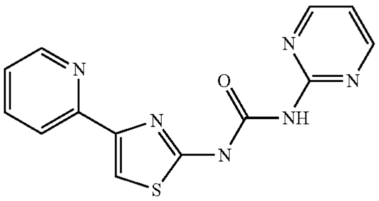 [SMILES: O=C(Nc1ncccn1)Nc1nc(-c2ccccn2)cs1] | ≥50.0 | ≤5.0 |

TABLE 6-continued
Exemplary cell viability screening results for compounds of the disclosure with Huh-7 cells, THLE2 cells and PH5CH cells.
| Entry | Structure | Cytotoxicity $CC_{50}$ (□M) | Selectivity |
|---|---|---|---|
| 4 | 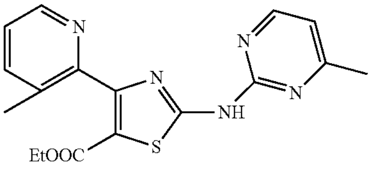 [SMILES: CCOC(=O)c1sc(Nc2nccc(C)n2)nc1-c1ncccc1C] | ≥50.0 | ≤5.0 |
| 5 | 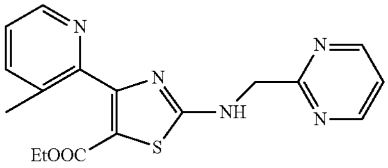 [SMILES: CCOC(=O)c1sc(NCc2ncccn2)nc1-c1ncccc1C] | ≥50.0 | ≤5.0 |
| 6 | 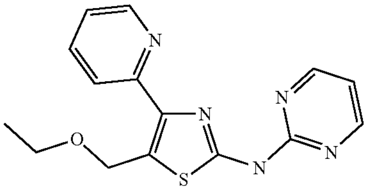 [SMILES: CCOCc1sc(Nc2ncccn2)nc1-c1ccccn1] | <50.0 | >5.0 |
| 7 | 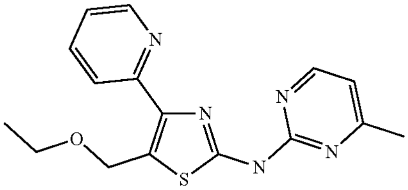 [SMILES: CCOCc1sc(Nc2nccc(C)n2)nc1-c1ccccn1] | <50.0 | ≤5.0 |
| 8 | 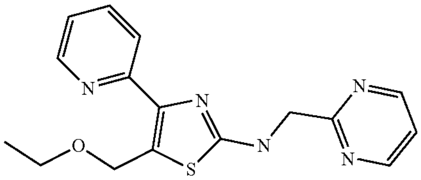 [SMILES: CCOCc1sc(NCc2ncccn2)nc1-c1ccccn1] | ≥50.0 | ≤5.0 |
| 9 | 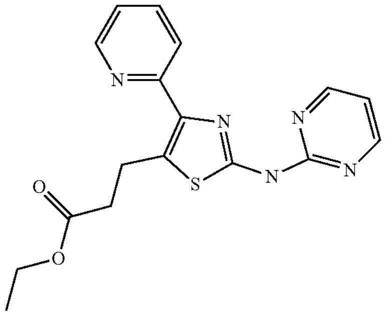 [SMILES: CCOC(=O)CCc1sc(Nc2ncccn2)nc1-c1ccccn1] | <50.0 | >5.0 |

TABLE 6-continued
Exemplary cell viability screening results for compounds of the disclosure with Huh-7 cells, THLE2 cells and PH5CH cells.
| Entry | Structure | Cytotoxicity $CC_{50}$ (□M) | Selectivity |
| --- | --- | --- | --- |
| 10 | 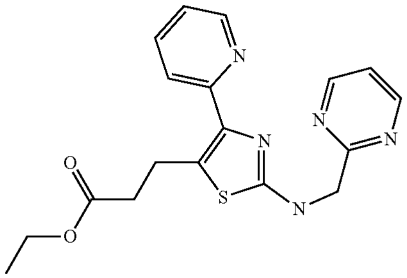 [SMILES: CCOC(=O)CCc1sc(NCc2ncccn2)nc1-c1ccccn1] | ≥50.0 | ≤5.0 |
| 11 | 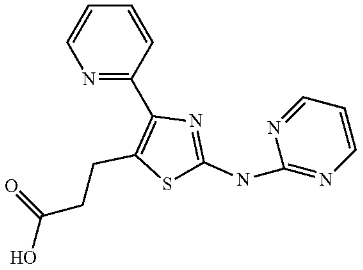 [SMILES: O=C(O)CCc1sc(Nc2ncccn2)nc1-c1ccccn1] | <50.0 | ≤5.0 |
| 12 | 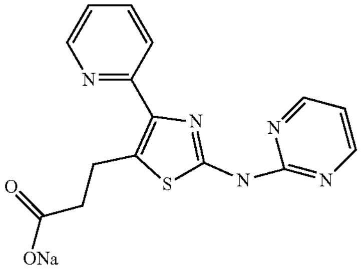 | <50.0 | ≤5.0 |
| 13 | 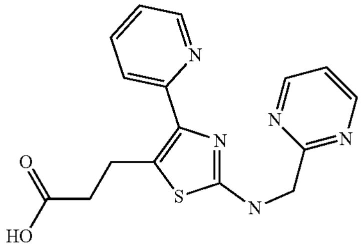 [SMILES: O=C(O)CCc1sc(NCc2ncccn2)nc1-c1ccccn1] | ≥50.0 | ≤5.0 |
| 14 | 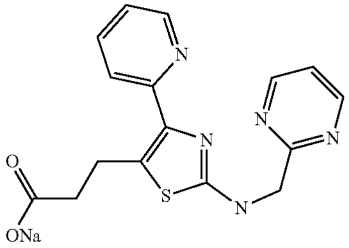 | ≥50.0 | ≤5.0 |

TABLE 6-continued
Exemplary cell viability screening results for compounds of the disclosure with Huh-7 cells, THLE2 cells and PH5CH cells.
| Entry | Structure | Cytotoxicity $CC_{50}$ (□M) | Selectivity |
|---|---|---|---|
| 15 | 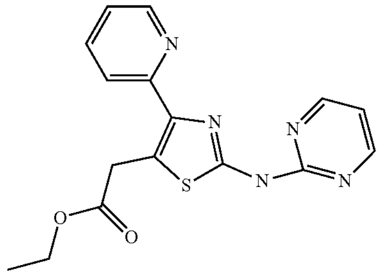 [SMILES: CCOC(=O)Cc1sc(Nc2ncccn2)nc1-c1ccccn1] | <50.0 | >5.0 |
| 16 | 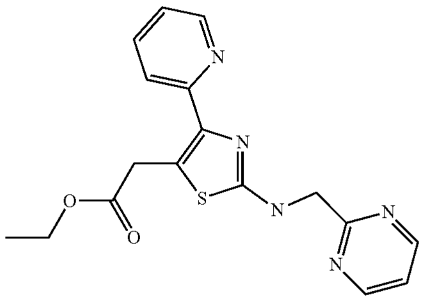 [SMILES: CCOC(=O)Cc1sc(NCc2ncccn2)nc1-c1ccccn1] | <50.0 | ≤5.0 |
| 17 | 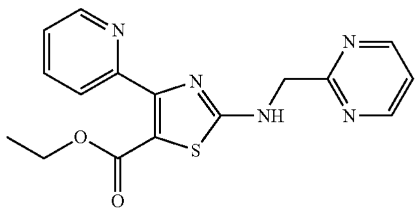 [SMILES: CCOC(=O)c1sc(NCc2ncccn2)nc1-c1ccccn1] | ≥50.0 | ≤5.0 |
| 18 | 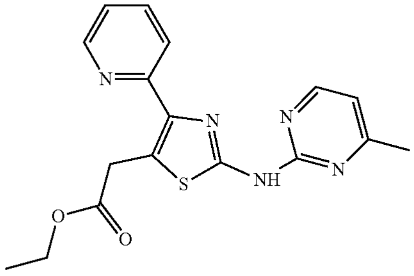 [SMILES: CCOC(=O)Cc1sc(Nc2nccc(C)n2)nc1-c1ccccn1] | <50.0 | ≤5.0 |
| 19 | 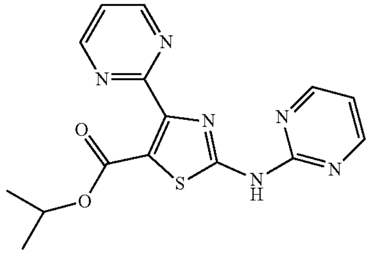 | <50.0 | >5.0 |

TABLE 6-continued
Exemplary cell viability screening results for compounds of the disclosure with Huh-7 cells, THLE2 cells and PH5CH cells.
| Entry | Structure | Cytotoxicity $CC_{50}$ (□M) | Selectivity |
| --- | --- | --- | --- |
| 20 | 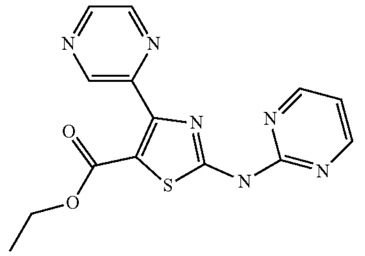 [SMILES: CCOC(=O)c1sc(Nc2ncccn2)nc1-c1cnccn1] | <50.0 | >5.0 |
| 21 | 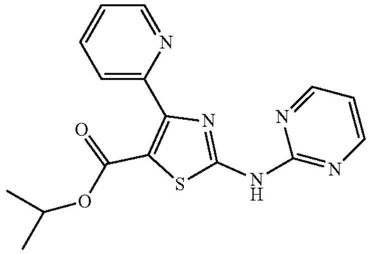 [SMILES: CC(C)OC(=O)c1sc(Nc2ncccn2)nc1-c1ccccn1] | <50.0 | >5.0 |
| 22 | 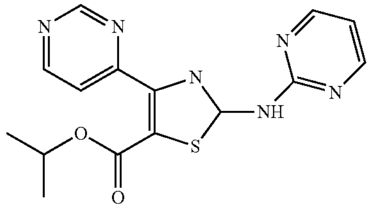 [SMILES: CC(C)OC(=O)C1=C(c2ccncn2)NC(Nc2ncccn2)S1] | <50.0 | >5.0 |
| 23 | 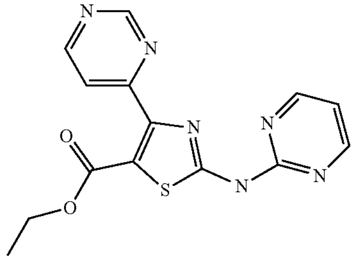 [SMILES: CCOC(=O)c1sc(Nc2ncccn2)nc1-c1ccncn1] | <50.0 | >5.0 |
| 24 | 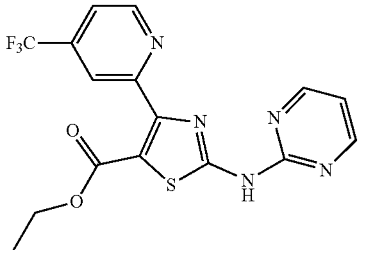 [SMILES: CCOC(=O)c1sc(Nc2ncccn2)nc1-c1cc(C(F)(F)F)ccn1] | <50.0 | >5.0 |
| 25 | 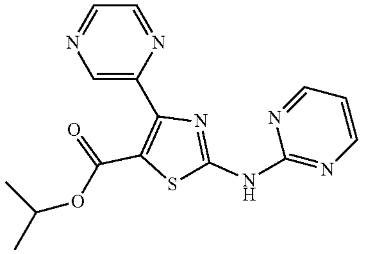 [SMILES: CC(C)OC(=O)c1sc(Nc2ncccn2)nc1-c1cnccn1] | <50.0 | >5.0 |

TABLE 6-continued
Exemplary cell viability screening results for compounds of the disclosure with Huh-7 cells, THLE2 cells and PH5CH cells.
| Entry | Structure | Cytotoxicity $CC_{50}$ (□M) | Selectivity |
|---|---|---|---|
| 26 | 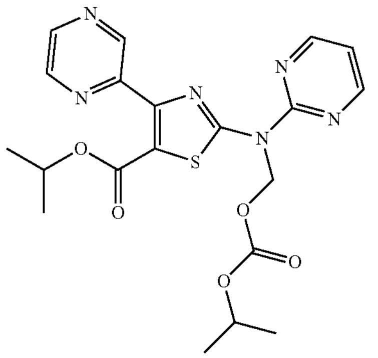 | <50.0 | >5.0 |
| 27 | 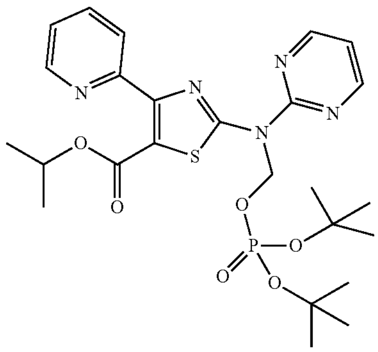 [SMILES: CC(C)OC(=O)c1sc(N(COP(=O)(OC(C)(C)C)OC(C)(C)C)c2ncccn2)nc1-c1ccccn1] | <50.0 | >5.0 |
| 28 | 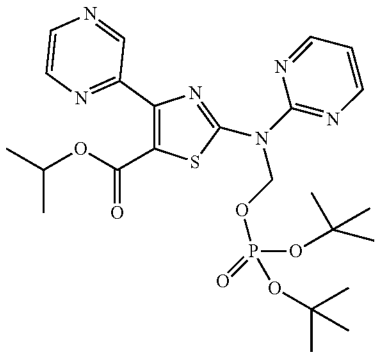 [SMILES: CC(C)OC(=O)c1sc(N(COP(=O)(OC(C)(C)C)OC(C)(C)C)c2ncccn2)nc1-c1cnccn1] | <50.0 | >5.0 |
| 29 | 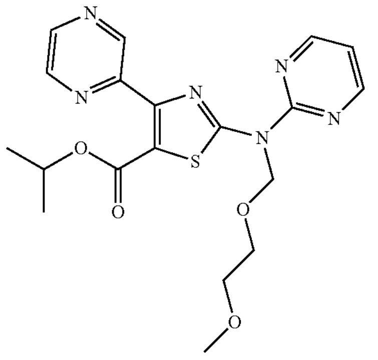 [SMILES: COCCOCN(c1ncccn1)c1nc(-c2cnccn2)c(C(=O)OC(C)C)s1] | ≥50.0 | ≤5.0 |

TABLE 6-continued

| Exemplary cell viability screening results for compounds of the disclosure with Huh-7 cells, THLE2 cells and PH5CH cells. | | | |
|---|---|---|---|
| Entry | Structure | Cytotoxicity $CC_{50}$ (□M) | Selectivity |
| 30 | 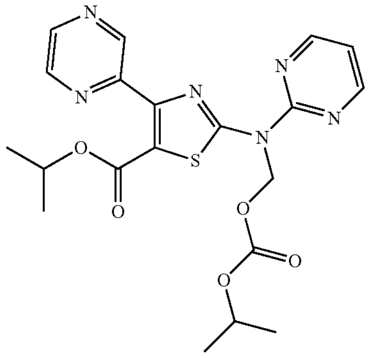 [SMILES: CC(C)OC(=O)OCN(c1ncccn1)c1nc(-c2cnccn2)c(C(=O)OC(C)C)s1] | <50.0 | >5.0 |

$CC_{50}$ in table 6 is defined as the concentration of compound that is reduces signal of viable cells by 50% in a treated culture.

Selectivity in table 6 is defined as the ratio of $CC_{50}$ between Huh7 and THLE2 and/or PH5CH (normal hepatocyte-derived) cell.

What is claimed is:

1. A compound having formula (I):

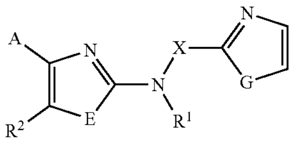

(I)

including enantiomers, diastereomers, hydrates, solvates, pharmaceutically acceptable salts, prodrugs and complexes thereof, wherein:

A is selected from the group consisting of

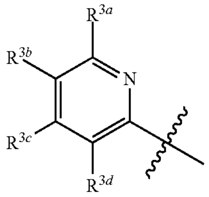 , 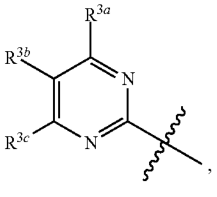 , 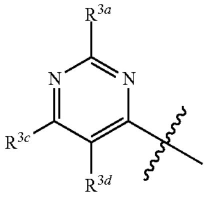 and 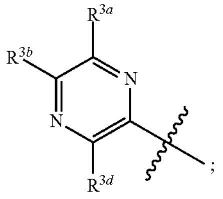 ;

E is selected from the group consisting of $CR^4{=}CR^5$ and sulfur;

G is NH;

X is selected from a group consisting of $(CH_2)_m$ and CONH—;

m=0, 1, 2, 3, or 4;

$R^1$ is selected from the group consisting of hydrogen,

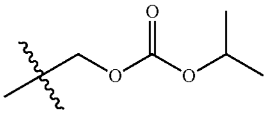 , 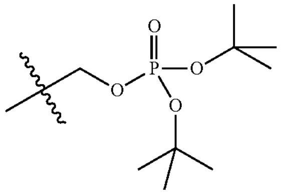 , 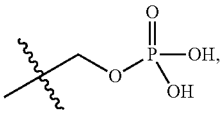 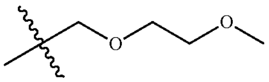 , 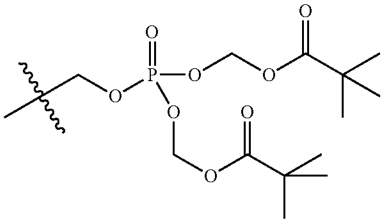 , and 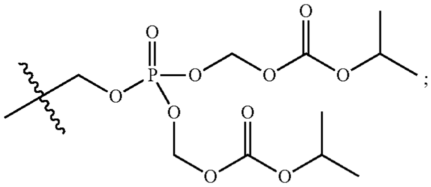 ;

$R^2$ is selected from the group consisting of hydrogen,

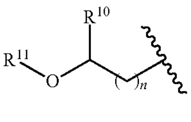 , 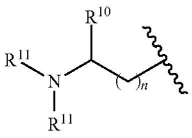 and

-continued

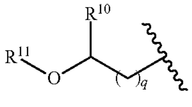

$R^{3a}$, $R^{3b}$, and $R^{3c}$ are at each occurrence independently selected from the group consisting of hydrogen, halogen, optionally substituted $C_{1-6}$ alkyl, and optionally substituted $C_{1-6}$ haloalkyl;

$R^{3d}$ is selected from the group consisting of hydrogen, halogen, optionally substituted $C_{1-6}$ alkyl, optionally substituted $C_{1-6}$ haloalkyl, optionally substituted $C_{1-6}$ alkenyl, $CO_2R^7$, $CONHR^8$, and $OR^9$;

n=0 or 1;

q=0, 1 or 2;

$R^4$ is at each occurrence independently selected from the group consisting of hydrogen, halogen, optionally substituted $C_{1-6}$ alkyl, optionally substituted $C_{1-6}$ haloalkyl, optionally substituted $C_{1-6}$ alkenyl, $CO_2R^7$, $CONHR^8$, and $OR^9$;

$R^5$ is at each occurrence independently selected from the group consisting of hydrogen, halogen, optionally substituted $C_{1-6}$ alkyl, optionally substituted $C_{1-6}$ haloalkyl, optionally substituted $C_{1-6}$ alkenyl, $CO_2R^7$, $CONHR^8$, and $OR^9$;

$R^6$ is at each occurrence independently selected from the group consisting of hydrogen, halogen, optionally substituted $C_{1-6}$ alkyl, optionally substituted $C_{1-6}$ haloalkyl, optionally substituted $C_{1-6}$ alkenyl, $CO_2R^7$, $CONHR^8$, and $OR^9$;

$R^7$ is at each occurrence independently selected from the group consisting of hydrogen and optionally substituted $C_{1-6}$ alkyl;

$R^8$ is at each occurrence independently selected from the group consisting of hydrogen and optionally substituted $C_{1-6}$ alkyl;

$R^9$ is at each occurrence independently selected from the group consisting of hydrogen, halogen, and optionally substituted $C_{1-6}$ alkyl;

$R^{10}$ is at each occurrence independently selected from the group consisting of hydrogen, cyclopropyl,

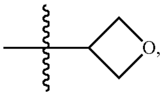 [SMILES: *C1COC1]

$CF_3$, and $CHF_2$; and $R^{11}$ is at each occurrence independently selected from the group consisting of hydrogen and optionally substituted $C_{1-6}$ alkyl.

2. The compound according to claim 1, wherein A is selected from:

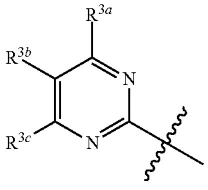

,

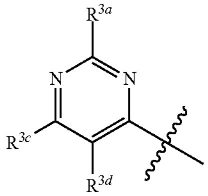

and

-continued

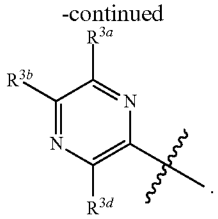

3. The compound according to claim 1, wherein A is selected from:

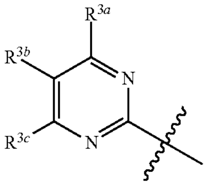

and

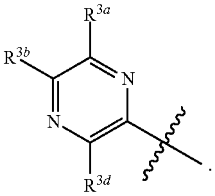

4. The compound according to claim 1, wherein $R^1$ is selected from hydrogen;

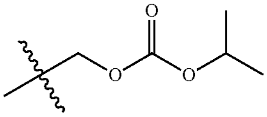

;

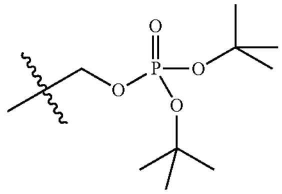

;

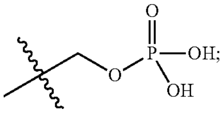

;

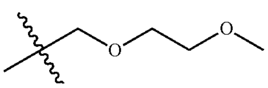

; and

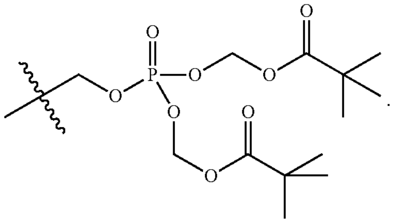

5. The compound according to claim 1, wherein $R^1$ is selected from hydrogen;

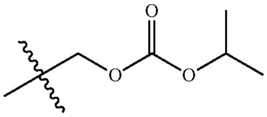

;

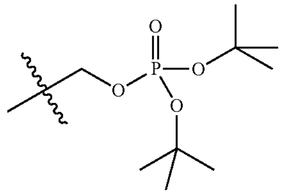

;

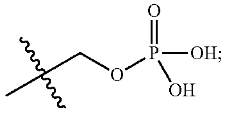

; and

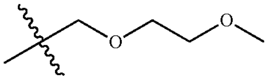

6. The compound according to claim 1, wherein $R^1$ is selected from hydrogen;

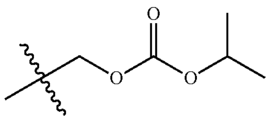
;

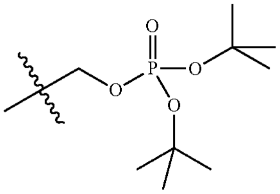
; and
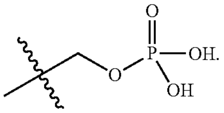

7. The compound according to claim 1, wherein $R^1$ is selected from hydrogen;

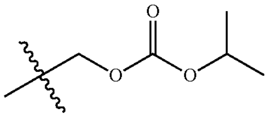
; and

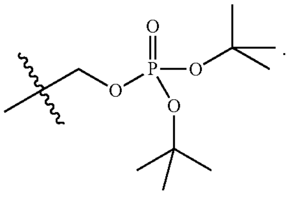

8. The compound according to claim 1, wherein $R^2$ is selected from hydrogen;

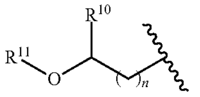
and
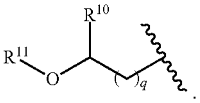

9. The compound according to claim 1, wherein X is $(CH_2)_m$.

10. The compound according to claim 1, wherein m=0, 1, 2 or 3.

11. The compound according to claim 1, wherein E is sulfur.

12. A compound having the structural formula:

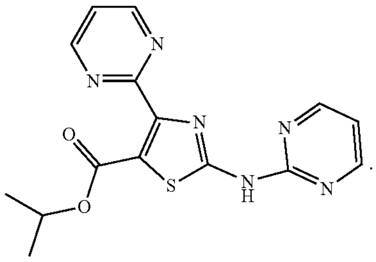 [SMILES: CC(C)OC(=O)c1sc(Nc2ncccn2)nc1-c1ncccn1]

13. A compound having the structural formula:

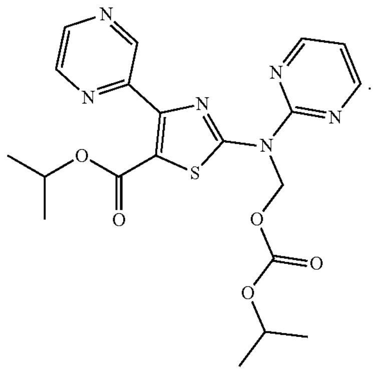 [SMILES: CC(C)OC(=O)OCN(c1ncccn1)c1nc(-c2cnccn2)c(C(=O)OC(C)C)s1]

14. A composition comprising a compound according to claim 1, and a pharmaceutically acceptable carrier.

15. A method of treating or preventing a disease that involves unregulated cell growth, said method comprising administering to a subject in need thereof, an effective amount of a compound according to claim 1.

16. The method according to claim 15, wherein the disease that involves unregulated cell growth is selected from primary liver cancer, hepatocellular carcinoma, hepatoblastoma, cholangiocarcinoma breast cancer, ovarian cancer, lung cancer, leukemia, and metastatic disease.

17. A method of treating or preventing a disease or condition associated with a hepatitis virus, said method comprising administering to a subject in need thereof, an effective amount of a compound according to claim 1.

18. The method according to claim 17, wherein the hepatitis virus is selected from hepatitis A virus, hepatitis B virus, hepatitis C virus, hepatitis D virus, and hepatitis E virus.

* * * * *